US008623821B2

(12) United States Patent
Landgraf et al.

(10) Patent No.: US 8,623,821 B2
(45) Date of Patent: Jan. 7, 2014

(54) ZYMOGEN ACTIVATORS

(71) Applicant: Genentech, Inc., South San Francisco, CA (US)

(72) Inventors: Kyle E. Landgraf, Alameda, CA (US); Robert A. Lazarus, Millbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/650,958

(22) Filed: Oct. 12, 2012

(65) Prior Publication Data

US 2013/0096072 A1 Apr. 18, 2013

Related U.S. Application Data

(60) Provisional application No. 61/547,628, filed on Oct. 14, 2011, provisional application No. 61/648,470, filed on May 17, 2012, provisional application No. 61/661,180, filed on Jun. 18, 2012.

(51) Int. Cl.
*A61K 38/26* (2006.01)
*A61P 3/10* (2006.01)
*A61P 7/12* (2006.01)
*C07K 14/605* (2006.01)

(52) U.S. Cl.
USPC ...................................................... 514/11.7

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 5,223,409 A | 6/1993 | Ladner et al. | |
| 5,624,821 A | 4/1997 | Winter et al. | |
| 5,648,260 A | 7/1997 | Winter et al. | |
| 5,750,373 A | 5/1998 | Garrard et al. | |
| 6,270,964 B1 | 8/2001 | Michnick et al. | |
| 6,294,330 B1 | 9/2001 | Michnick et al. | |
| 2005/0260186 A1 | 11/2005 | Bookbinder et al. | |
| 2006/0104968 A1 | 5/2006 | Bookbinder et al. | |
| 2009/0047210 A1* | 2/2009 | Ruggles et al. .............. | 424/1.11 |

FOREIGN PATENT DOCUMENTS

| | | |
|---|---|---|
| EP | 0596524 A2 * | 5/1994 |
| WO | 94/29351 A2 | 12/1994 |
| WO | 99/51642 A1 | 10/1999 |
| WO | 00/06717 A2 | 2/2000 |
| WO | WO 2012031115 A2 * | 3/2012 |

OTHER PUBLICATIONS

Landgraf et al "Allosteric Peptide Activators of Pro-Hepatocyte Growth Factor Stimulate Met Signaling" J Biol Chem 285:40362-40372. Published online Oct. 11, 2010.*

Adams et al., "PHENIX: a comprehensive Python-based system for macromolecular structure solution" Acta Cryst. D66:213-21 (2010).
Arakaki et al., "Evidence for the presence of an inactive precursor of human hepatocyte growth factor in plasma and sera of patients with liver diseases" Hepatology 22(6):1728-34 (1995).
Bevan et al., "Diverse and potent activities of HGF/SF in skin wound repair" J Pathol. 203(3):831-8 (2004).
Bode et al., "The transition of bovine trypsinogen to a trypsin-like state upon strong ligand binding. The refined crystal structures of the bovine trypsinogen-pancreatic trypsin inhibitor complex and of its ternary complex with Ile-Val at 1.9 A resolution" J Mol Biol. 118(1):99-112 (1978).
Bussolino et al., "Hepatocyte Growth Factor is a Potent Angiogenic Factor Which Stimulates Endothelial Cell Motility and Growth" J Cell Biol 119(3):629-641 (Nov. 1992).
Carell et al., "A Solution-Phase Screening Procedure for the Isolation of Active Compounds from a Library of Molecules" Angewandte Chemie International Edition 33:2061-64 (1994).
Carell et al., "A Solution-Phase Screening Procedure for the Isolation of Active Compounds from a Library of Molecules" Angewandte Chemie International Edition 33:2059-2061 (1994).
Chevray and Nathans, "Protein interaction cloning in yeast: Identification of Mammalian Proteins that react with leucine zipper of Jun" P Natl Acad Sci USA 89:5789-5793 (1991).
Chien et al., "The Two-Hybrid System: A Method to Identify and Clone Genes for Proteins that Interact with a Protein of Interest" P Natl Acad Sci USA 88:9578-9582 (Nov. 1991).
Cho et al., "An Unnatural BioPolymer" Science 261:1303-1305 (1993).
Cull et al., "Screening for receptor ligands using large libraries of peptides linked to the C terminus of the lac repressor" Proc Natl Acad Sci U S A. 89(5):1865-9 (1992).
Cwirla et al., "Peptides on phage: a vast library of peptides for identifying ligands" P Natl Acad Sci USA 87:6378-6382 (Aug. 1990).
Derman et al., "HGF-mediated chemotaxis and tubulogenesis require activation of the phosphatidylinositol 3-kinase" Am J Physiol. 268:F1211-7 (1995).
Devlin et al., "Random peptide libraries: a source of specific protein binding molecules" Science 249:404-406 (1990).
DeWitt et al., "'Diversomers': an approach to nonpeptide, nonoligomeric chemical diversity" Proc Natl Acad Sci U S A. 90(15):6909-13 (1993).
Donate et al., "Molecular evolution and domain structure of plasminogen-related growth factors (HGF/SF and HGFI/MSP)" Protein Sci 3:2378-2394 (1994).
Duncan and Winter, "The binding site for Clq on IgG" Nature 322:738-740 (1988).

(Continued)

*Primary Examiner* — Cecilia J Tsang
*Assistant Examiner* — Zachary J. Miknis
(74) *Attorney, Agent, or Firm* — Stephanie Yonker

(57) ABSTRACT

Provided herein are zymogen activating molecules such as zymogen activating peptides, and methods of identifying and using these zymogen activating molecules such as zymogen activating peptides.

19 Claims, 9 Drawing Sheets

(56) References Cited

OTHER PUBLICATIONS

Ellington and Szostak et al., "In vitro selection of RNA molecules that bind specific ligands" Nature 346(6287):818-822 (Aug 30, 1990).
Emsley et al., "Features and development of Coot" Acta crystallographica D66:486-501 (2010).
Faccio et al., "Characterization of a novel human serine protease that has extensive homology to bacterial heat shock endoprotease HtrA and is regulated by kidney ischemia" J Biol Chem 275(4):2581-2588 (Jan. 28, 2000).
Felici, "Selection of antibody ligands from a large library of oligopeptide expressed on a multivalent exposition vector" J Mol Biol 222:301-310 (1991).
Finn et al., "The Pfam protein families database" Nucleic Acids Res. 38:D211-22 (2010).
Fodor et al., "Multiplexed biochemical assays with biological chips" Nature 364:555-6 (1993).
Gallop et al. et al., "Applications of combinatorial technologies to drug discovery. 1. background and peptide combinatorial libraries" J Med Chem 37(9):1233-1251 (1994).
Grant et al., "Scatter Factor Induces Blood Vessel Formation In Vivo" P Natl Acad Sci USA 90:1937-1941 (1993).
Hartmann et al., "A Functional Domain in the Heavy Chain of Scatter Factor/Hepatocyte Growth Factor Binds the c-Met Receptor and Induces Cell Dissociation but Not Mitogenesis" P Natl Acad Sci USA 89(23):11574-11578 (Dec. 1, 1992).
Hedstrom, "Serine Protease Mechanism and Specificity" Chem Rev 102(12):4501-4523 (Dec. 2002).
Hodgson et al., "The synthesis of peptides and proteins containing non-natural amino acids" Chem Soc Rev. 33(7):422-30 (2004).
Houghten et al., "The use of synthetic peptide combinatorial libraries for the identification of bioactive peptides" Biotechniques 13(3):412-21 (Sep. 1992).
Jespers et al., "Surface Expression and Ligand-Based Selection of cDNAs Fused to Filamentous Phage Gene VI" Bio-Technol 13:378-382 (Apr. 1995).
Kaibori et al., "Impairment of activation of hepatocyte growth factor precursor into its mature form in rats with liver cirrhosis" J Surg Res. 106(1):108-14 (2002).
Khan et al., "Molecular mechanisms for the conversion of zymogens to active proteolytic enzymes" Protein Sci. 7(4):815-36 (1998).
Kirchhofer et al., "Structural and functional basis of the serine protease-like hepatocyte growth factor beta-chain in Met binding and signaling" J Biol Chem 279(38):39915-39924 (Sep 17, 2004).
Kirchhofer et al., "Utilizing the activation mechanism of serine proteases to engineer hepatocyte growth factor into a Met antagonist" Proc Natl Acad Sci U S A. 104(13):5306-11 (2007).
Lam et al., "A new type of synthetic peptide library for identifying ligand-binding activity" Nature 354:82-84 (1991).
Landgraf et al., "Allosteric Peptide Activators of Pro-Hepatocyte Growth Factor Stimulate Met Signaling" Journal of Biological Chemistry 285(51):40362-40372 (Dec. 2010).
Lee et al., "Activation of Hepatocyte Growth Factor and Urokinase/Plasmingoen Activator by Matriptase, an Epithelial Membrane Serine Protease" J Biol Chem 275:36720-36725 (2000).
Lokker et al., "Structure-Function Analysis of Hepatocyte Growth Factor: Identification of Variants that Lack Mitogenic Activity Yet Retain High Affinity Receptor Binding" EMBO J 11(7):2503-2510 (1992).
Lowman et al., "Molecular Mimics of Insulin-Like Growth Factor 1 (IGF-1) for Inhibiting IGF-1: IGF-Binding Protein Interactions" Biochemistry-US 37(25):8870-8878 (1998).
Lowman, "Bacteriophage display and discovery of peptide leads for drug development" Annu Rev Biophys Biomol Struct. 26:401-24 (1997).
Marchand-Adam et al., "Defect of pro-hepatocyte growth factor activation by fibroblasts in idiopathic pulmonary fibrosis" Am J Respir Crit Care Med. 174(1):58-66 (2006).

Martins et al., "Binding specificity and regulation of the serine protease and PDZ domains of HtrA2/Omi." J Biol Chem 278(49):49417-49427 (Dec. 5, 2003).
McCoy et al., "Phaser crystallographic software" J Appl Crystallogr. 40:658-674 (2007).
Murshudov et al., "Refinement of macromolecular structures by the maximum-likelihod method" Acta Cyst. D53:240-255 (1997).
Nakamura et al., "Hepatocyte growth factor twenty years on: Much more than a growth factor" J Gastroenterol Hepatol. 26( SUPPL 1):188-202 (2011).
Nakamura et al., "Molecular Cloning and Expression of Human Hepatocyte Growth Factor" Nature 342:440-443 (Nov. 23, 1989).
Naldini et al., "Extracellular Proteolytic Cleavage by Urokinase is Required for Activation of Hepatocyte Growth Factor/Scatter Factor" EMBO J 11(13):4825-4833 (Dec. 1992).
Peek et al., "Unusual Proteolytic Activation of Pro-hepatocyte Growth Factor by Plasma Kallikrein and Coagulation Factor XIa" J Biol Chem 277(49):47804-9 (Dec. 6, 2002).
Phin et al., "Imbalance in the pro-hepatocyte growth factor activation system in bleomycin-induced lung fibrosis in mice" Am J Respir Cell Mol Biol. 42(3):286-93 (2010).
Rawlings et al., "MEROPS: the peptidase database" Nucleic Acids Res. 38:D227-33 (2010).
Sandberg et al., "New chemical descriptors relevant for the design of biologically active peptides. A multivariate characterization of 87 amino acids" J Med Chem. 41(14):2481-91 (1998).
Scott et al., "Searching for peptide ligands with an epitope library" Science 249:386-390 (1990).
Shimomura et al., "Activation of hepatocyte growth factor by two homologous proteases, blood-coagulation factor XIIa and hepatocyte growth factor activator" Eur J Biochem 229(1):257-261 (Apr. 1, 1995).
Sidhu et al., "Phage Display for Selection of Novel Binding Peptides" Method Enzymol 328:333-363 (2000).
Siebenlist et al., "*E. coli* RNA polymerase interacts homologously with two different promoters" Cell 20:269-281 (Jun. 1980).
Stamos et al., "Crystal structure of the HGF beta-chain in complex with the Sema domain of the Met receptor" EMBO J 23(12):2325-2335 (Jun. 16, 2004).
Stoker et al., "Scatter Factor is a Fibroblast-Derived Modulator of Epithelial Cell Mobility" Nature 327 (6119):239-242 (May 21, 1987).
Tonikian et al., "Identifying specificity profiles for peptide recognition modules from phage-displayed peptide libraries" Nat Protoc. 2(6):1368-86 2007).
Tordai et al., "The PAN module: the N-terminus domains of plasminogen and hepatocyte growth factor are homologous with the apple domains of the prekallikrein family and with a novel domain found in numerous nematode proteins" FEBS LETT 461:63-67 (1999).
Tuerk and Gold, "Systematic evolution of ligands by exponential enrichment: RNA ligands to bacteriophage T4 DNA polymerase" Science 249(4968):505-510 (Aug. 3, 1990).
Watanabe et al., "Hepatocyte growth factor accelerates the wound repair of cultured gastric mucosal cells" Biochem Biophys Res Commun.(199):1453-60 (1994).
Xie et al., "Adding amino acids to the genetic repertoire" Curr Opin Chem Biol. 9(6):548-54 (2005).
Zuckermann et al., "Discovery of nanomolar ligands for 7-transmembrane G-protein-coupled receptors from a diverse N-(substituted)glycine peptoid library" J Med Chem. 37(17):2678-85 (1994).
Database accession No. AOG19059 (Kirchhofer) Feb. 21, 2008.
Database accession No. AUN66894 (Hood) Feb. 3, 2011.
International Search Report, PCT/US2012/059891, dated Jan. 28, 2013.
Ta et al., "Noncompetitive Inhibition of Hepatocyte Growth Factor-dependent Met Signaling by a Phage-derived Peptide" J. Mol. Biol. 385:79-90 ( 2009).

\* cited by examiner

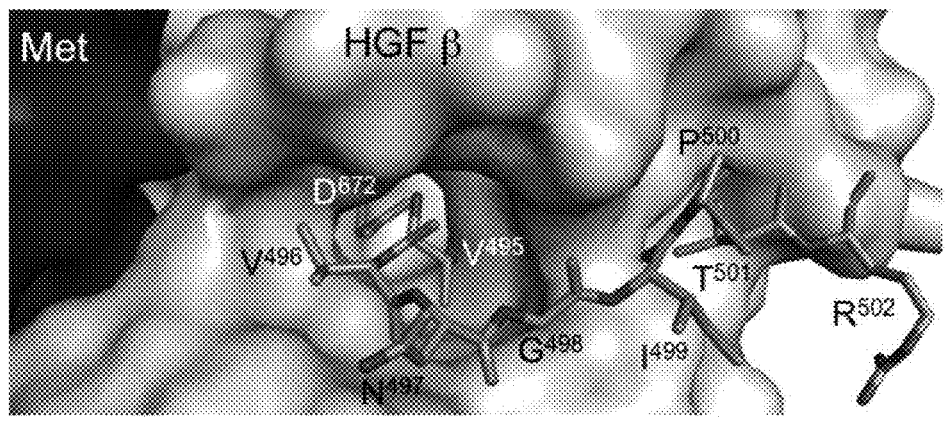
FIG. 3
I-V-G-G-($X_5$-$X_{11}$) - gene VIII
FIG. 4A
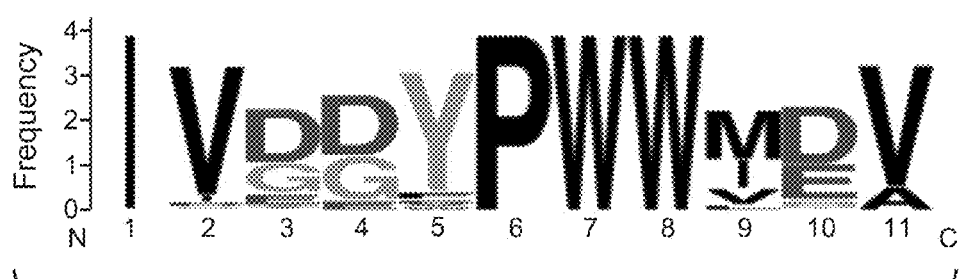
FIG. 4B
| $X_1$ | $X_2$ | $X_3$ | $X_4$ | $X_5$ | $X_6$ | $X_7$ | $X_8$ | $X_9$ | $X_{10}$ | $X_{11}$ |
|---|---|---|---|---|---|---|---|---|---|---|
| I | V/I | D/G | D/G | Y | P | W | W | M/I/V | D/E | V/A |
FIG. 4C

| $X_1$ | $X_2$ | $X_3$ | $X_4$ | $X_5$ | $X_6$ | $X_7$ | $X_8$ | $X_9$ | $X_{10}$ | $X_{11}$ |
|---|---|---|---|---|---|---|---|---|---|---|
| I | I | G | G | Y | P | W | W | M | D | V |
| V | V | N |   | F |   |   |   | I | E | A |
| L | L | D |   |   |   |   |   | V |   |   |
|   | Y | E |   |   |   |   |   |   |   |   |
|   | F |   |   |   |   |   |   |   |   |   |
FIG. 7
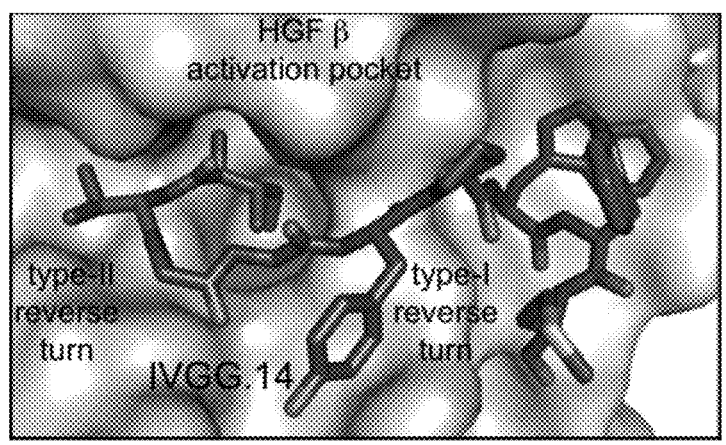
FIG. 8A
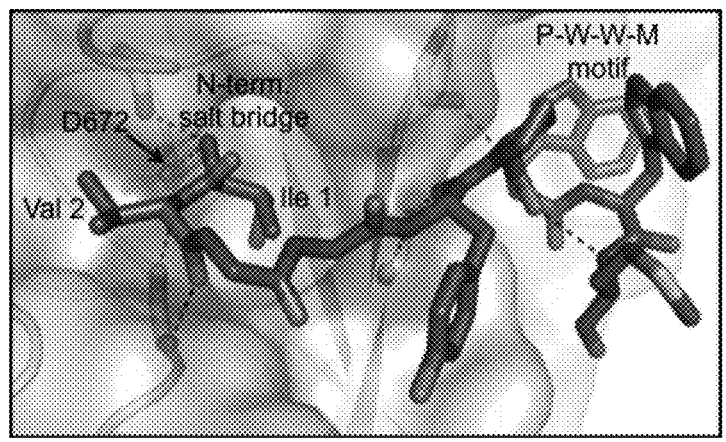
FIG. 8B

I-(NTT)-G-G-X-P-X-W(X₇) - gene VIII

Linear ZAPtides

ZAP.13  I  I  G  G  D  P  V  W  D  I  T  Y  T  Y  A
ZAP.04  I  I  G  G  D  P  Y  W  Y  P  H  P  G  T  V
ZAP.01  I  V  G  G  D  P  Y  W  V  P  H  P  G  D  A
ZAP.30  I  I  G  G  D  P  W  W  T  P  H  P  S  F  V
ZAP.86  I  V  G  G  D  P  W  W  V  D  H  M  Y  L  T

Cyclic ZAPtides

ZAP.11  I  V  G  G  C  P  Y  W  M  D  R  E  E  C  L
ZAP.03  I  I  G  G  C  P  Y  W  M  D  R  E  E  C  I

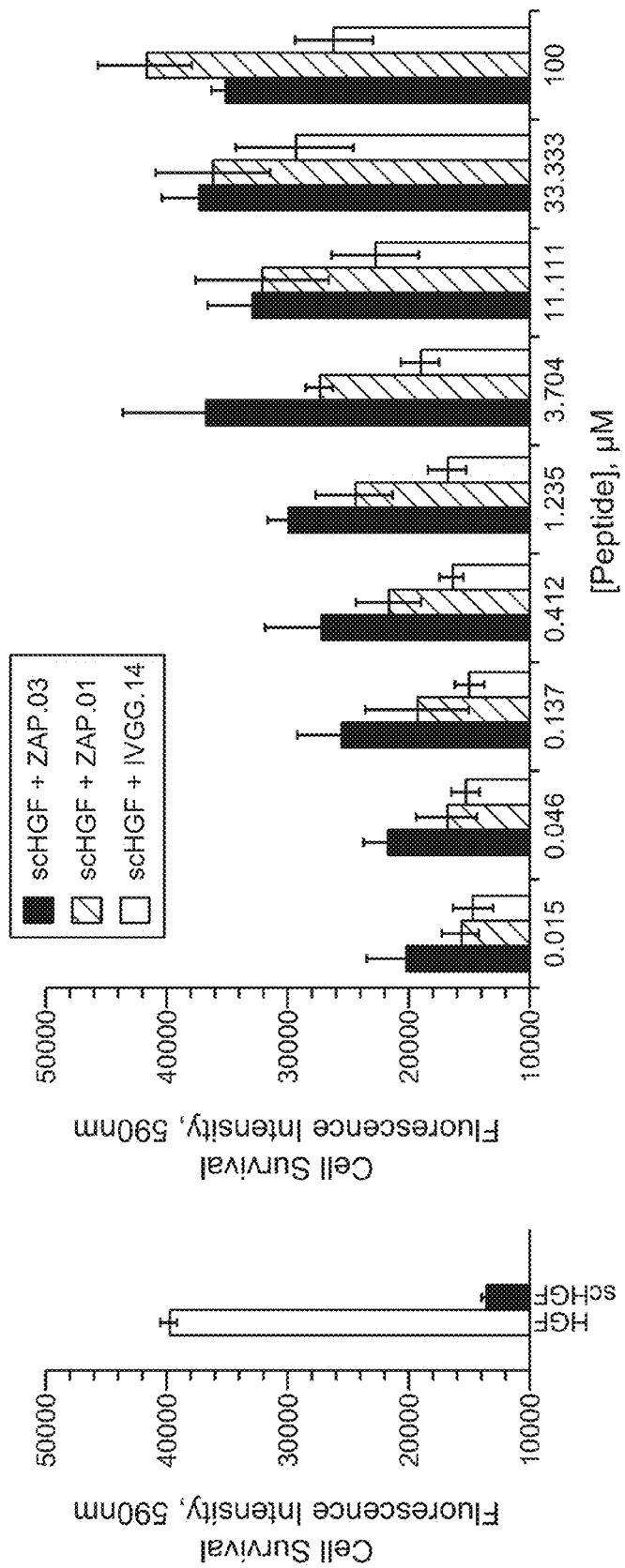

ZYMOGEN ACTIVATORS

RELATED APPLICATION

This application claims benefit under 35 U.S.C. §119 to provisional U.S. Application No. 61/547,628, filed Oct. 14, 2011, U.S. Application No. 61/648,470, filed May 17, 2012 and U.S. Application No. 61/661,180, filed Jun. 18, 2012, the contents of which are hereby incorporated by reference in their entirety.

TECHNICAL FIELD

Provided herein are zymogen activating molecules such as zymogen activating peptides, and methods of identifying and using these zymogen activating molecules (e.g., zymogen activating peptides).

SEQUENCE LISTING

The instant application contains a Sequence Listing submitted via EFS-Web and hereby incorporated by reference in its entirety. Said ASCII copy, created on Oct. 9, 2012, is named P4768R1U.txt, and is 66,169 bytes in size.

BACKGROUND

Hepatocyte growth factor (HGF), also known as scatter factor, is a member of the plasminogen-related growth factor family and is a key mediator of cell migration, proliferation, survival, motility and morphogenesis (Stoker, M. et al. (1987) *Nature* 327: 239-42; Nakamura, T. et al. (1989) *Nature* 342: 440-3; Bussolino, F. et al. (1992) *J Cell Biol* 119: 629-41). HGF is known to specifically activate the Met receptor tyrosine kinase, resulting in downstream activation of RAS and PI3-Kinase signaling pathways, and is critical for processes such as wound healing and tissue regeneration (Grant, D. S. et al. (1993) *Proc Natl Acad Sci USA* 90: 1937-41; Watanabe, S. et al. (1994) *Biochem Biophys Res Commun* 199: 1453-60; Derman, M. P. et al. (1995) *Am J Physiol* 268: F1211-7; Bevan, D. et al. (2004) *J Pathol* 203: 831-8; Nakamura, T. et al. (2011) *J Gastroenterol Hepatol* 26 Suppl 1: 188-202). As a result, uncovering novel mechanisms for HGF-dependent activation of the Met receptor may provide new strategies for stimulating tissue repair in chronic wounds and fibrotic disorders (Nakamura, T. et al. (2011) *J Gastroenterol Hepatol* 26 Suppl 1: 188-202).

HGF is a secreted extracellular protein that exists as an inactive single-chain ligand (pro-HGF) until proteolytic cleavage at the $Arg^{494}$-$Val^{495}$ peptide bond results in a two-chain form, consisting of a disulfide-linked α/β-heterodimer, capable of activating the Met receptor (Nakamura, T. et al. (1989) *Nature* 342: 440-3; Naldini, L. et al. (1992) *EMBO J* 11: 4825-33; Shimomura, T. et al. (1995) *Eur J Biochem* 229: 257-61; Lee, S. L. et al. (2000) *J Biol Chem* 275: 36720-5; Peek, M. et al. (2002) *J Biol Chem* 277: 47804-9). The domain architecture of HGF is analogous to plasminogen, where the α-chain comprises an N-terminal PAN domain followed by four Kringle domain repeats (K1-4) and the β-chain contains the C-terminal trypsin/chymotrypsin-like serine protease domain (FIG. 1) (Donate, L. E. et al. (1994) *Protein Sci* 3: 2378-94; Tordai, H. et al. (1999) *FEBS Lett* 461: 63-7). Notably, both two-chain HGF and single-chain pro-HGF are capable of high affinity binding to the Met receptor through specific interactions with the α-chain; however, receptor activation can only occur after cleavage of pro-HGF into the two-chain form (Hartmann, G. et al. (1992) *Proc Natl Acad Sci USA* 89: 11574-8; Lokker, N. A. et al. (1992) *EMBO J* 11: 2503-10; Naldini, L. et al. (1992) *EMBO J* 11: 4825-33). Studies have indicated that during certain cases of liver cirrhosis and pulmonary fibrosis, the normal tissue repair process is severely compromised due to a lack of proteolytic conversion of available pro-HGF into the active form; leading to reduced Met signaling (Arakaki, N. et al. (1995) *Hepatology* 22: 1728-34; Kaibori, M. et al. (2002) *J Surg Res* 106: 108-14; Marchand-Adam, S. et al. (2006) *Am J Respir Crit Care Med* 174: 58-66; Phin, S. et al. (2010) *Am J Respir Cell Mol Biol* 42: 286-93). Not only does this highlight the importance of the cleavage step in regulating HGF-dependent Met signaling, but also suggests that allosteric activators that reversibly convert available pro-HGF into an active form, capable of Met signaling, would potentially yield a novel therapeutic approach to stimulating tissue repair in these indications (FIG. 2). There are many other indications where activation of HGF has potential benefit; for a review and partial list of tissues and disease areas see (Nakamura, T. et al. (2011) *J Gastroenterol Hepatol* 26 Suppl 1: 188-202) and Table 3 therein.

Extensive structural and biochemical work has revealed that HGF utilizes a trypsin/chymotrypsin-like serine protease activation mechanism for Met signaling (Kirchhofer, D. et al. (2004) *J Biol Chem* 279: 39915-24; Stamos, J. et al. (2004) *EMBO J* 23: 2325-35; Kirchhofer, D. et al. (2007) *Proc Natl Acad Sci USA* 104: 5306-11). Upon cleavage of pro-HGF, the newly formed N-terminus ($Val^{495}$) in the serine protease-like β-chain, which corresponds to residue 16 in chymotrypsinogen numbering, inserts into a canonical 'activation pocket' (FIG. 3). Detailed work has shown that N-terminal insertion is critical for allosterically activating the β-chain, allowing for Met binding and subsequent activation of receptor signaling. Importantly, studies have shown that mutating the N-terminal $Val^{495}$ to Gly or $Asp^{672}$ to Asn within the β-chain prevents N-terminal insertion, thereby disrupting β-chain binding to Met and completely abolishing the signaling activity of two-chain HGF (Kirchhofer, D. et al. (2007) *Proc Natl Acad Sci USA* 104: 5306-11). Thus, the key mechanistic step for conversion of pro-HGF into a Met agonist is directly analogous to the activation of trypsin/chymotrypsin-like serine proteases (Khan, A. R. et al. (1998) *Protein Sci* 7: 815-36; Hedstrom, L. (2002) *Chem Rev* 102: 4501-24), despite the fact that the serine protease-like β-chain mediates protein-protein interactions rather than proteolytic activity.

Previously it has been shown that small peptides derived from the first 7-10 residues of the native N-terminus of HGF β target the serine protease-like activation pocket of a zymogen-like form of HGF β (scHGF β), allosterically activate Met binding, and subsequently activate a non-cleavable form of pro-HGF (scHGF) in cell-based Met signaling assays (Landgraf, K. E. et al. (2010) *J Biol Chem* 285: 40362-72). While this established the ability to allosterically regulate pro-HGF signaling activity by targeting the activation pocket of HGF β, the therapeutic potential of the approach was limited due to the very weak binding affinity of the activator peptides ($K_D$~2 mM) (Landgraf, K. E. et al. (2010) *J Biol Chem* 285: 40362-72). Therefore there remains a need for effective activators of HGF signaling.

SUMMARY

Provided herein are zymogen activating molecules (e.g., zymogen activating peptides (ZAPs)), and methods for identifying and using zymogen activating molecules (e.g., ZAPs), capable of modulating activation of a polypeptide comprising a serine protease domain or serine protease-like domain (e.g., HGF) and activates the polypeptide comprising the serine protease zymogen domain or serine protease-like zymogen domain (e.g., HGF). For example, provided herein are zymogen activating molecules (e.g., ZAPs), and methods for identifying and using zymogen activating molecules (e.g., ZAPs), capable of modulating activation of c-Met by HGF, in particular by interacting with the β-chain domain of pro-HGF.

HGF/c-Met signaling pathway has important biological roles, and its perturbation has been implicated in wound healing, tissue regeneration, and tissue repair. Provided herein are compositions, and methods of using these compositions, for modulating activity of the β-chain domain of the HGF protein, in particular pro-HGF. Because of the important functions associated with HGF, compositions and methods herein present significant clinical utilities.

As described herein, a collection of zymogen activating molecules (e.g., ZAPs), which interact with the β-chain domain of HGF, were identified using a phage-displayed N-terminal peptide library. Characterization of the ZAPs resulted in the identification of unique motifs that are believed to confer molecules with the ability to interact with HGF, in particular pro-HGF, and activate c-Met signaling. Exemplary zymogen activating molecules (e.g., ZAPs) as described herein are useful for screening for modulators (e.g., activators) of polypeptides comprising a trypsin/chymotrypsin-like serine protease domain and/or trypsin/chymotrypsin-like serine protease-like domain. Furthermore, such zymogen activating molecules (e.g., ZAPs) and their derivatives are themselves small molecule drug candidates for treating pathological diseases and/or disorders associated with dysregulation of signaling pathways modulated by a polypeptide comprising a trypsin/chymotrypsin-like serine protease domain and/or trypsin/chymotrypsin-like serine protease-like domain such as HGF.

Provided herein are isolated zymogen activating peptides (ZAPs), wherein the ZAP comprises the amino acid sequence $X_1$-$X_2$-$X_3$-$X_4$-$B_n$ (SEQ ID NO:2), wherein $X_1$ is a large hydrophobic amino acid, $X_2$ is a large hydrophobic amino acid or an aromatic amino acid, $X_3$ is G, D, E, N, Q, D-Gly, D-Asp, D-Glu, D-Asn, or D-Gln, $X_4$ is G or A, B is any amino acid, and n is a number between 0-46. Also provided herein are isolated zymogen activating peptides (ZAPs), wherein the ZAP consists of the amino acid sequence $X_1$-$X_2$-$X_3$-$X_4$-$B_n$ (SEQ ID NO:3), wherein $X_1$ is a large hydrophobic amino acid, $X_2$ is a large hydrophobic amino acid or an aromatic amino acid, $X_3$ is G, D, E, N, Q or D-amino acid, $X_4$ is G or A, B is any amino acid, and n is a number between 0-46.

In some embodiments of any of the isolated ZAPs, $X_1$ is M, L, I, V or NorLeucine (SEQ ID NO:4). In some embodiments, $X_1$ is L, I, or V (SEQ ID NO:5). In some embodiments, $X_1$ is I, or V (SEQ ID NO:6). In some embodiments, $X_1$ is I (SEQ ID NO:7). In some embodiments of any of the isolated ZAPs, $X_2$ is M, L, I, V, NorLeucine, F, or Y (SEQ ID NO:8). In some embodiments, $X_2$ is I, V, L or F (SEQ ID NO:9). In some embodiments, $X_2$ is I or V (SEQ ID NO:10). In some embodiments of any of the isolated ZAPs, $X_3$ is G, D, or N (SEQ ID NO:11). In some embodiments, $X_3$ is G (SEQ ID NO:12). In some embodiments of any of the isolated ZAPs, $X_4$ is G (SEQ ID NO:13).

In some embodiments of any of the isolated ZAPs, the $X_1$-$X_2$-$X_3$-$X_4$ (SEQ ID NO:14) is IVGG (SEQ ID NO:15), IVDG (SEQ ID NO:16), IVdG (SEQ ID NO:17), IIGG (SEQ ID NO:18), VVGG (SEQ ID NO:19), VVGG (SEQ ID NO:20), IVGG (SEQ ID NO:21), LIDG (SEQ ID NO:22), IVEG (SEQ ID NO:23), ITGG (SEQ ID NO:24), IVNG (SEQ ID NO:25), IFNG (SEQ ID NO:26), IYGG (SEQ ID NO:27), ILGG (SEQ ID NO:28), or IKGG (SEQ ID NO:29), and wherein d is D-aspartic acid.

In some embodiments of any of the isolated ZAPs, the ZAP specifically binds a polypeptide comprising a serine protease domain or serine protease-like domain and activates the polypeptide comprising the serine protease zymogen domain or serine protease-like zymogen domain. In some embodiments, the ZAP specifically binds to the β-chain domain of pro-HGF and activates HGF signaling through c-Met. In some embodiments, the ZAP specifically binds to the activation pocket of the β-chain domain of pro-HGF. In some embodiments, the ZAP binds prethrombin-2 and activates the amidolytic activity of prethrombin-2 or prothrombin. In some embodiments, the ZAP binds Protein C and activates the amidolytic activity of Protein C.

In some embodiments of any of the isolated ZAPs, the ZAP allosterically activates the polypeptide comprising the serine protease zymogen domain or serine protease-like zymogen domain.

Further provided herein are ZAP fusions comprising the ZAP described herein conjugated to a carrier. In some embodiments, the carrier is a biodegradable polymer (e.g., PEG, polylactide, polyglycolide, polycaprolactone, and co-polymers thereof, carbohydrates, starches, cellulose, chitins, and lignins or a polypeptide carrier (e.g., Fc and serum albumin)). In some embodiments, conjugation of the ZAP to the carrier increases the half-life and/or bioavailability of the ZAP compared to the ZAP unconjugated to the carrier.

Provided herein are methods of treating a disease or disorder in an individual comprising administering an effective amount of any one of the ZAP or the ZAP fusion described herein. In some embodiments, a symptom of the disease or disorder is fibrosis or liver cirrhosis.

Also provided herein are methods of promoting tissue regeneration and/or tissue repair in an individual comprising administering an effective amount of any one of the ZAP or the ZAP fusion described herein.

In another aspect, provided herein are methods of identifying a ZAP capable of specifically binding a polypeptide comprising a serine protease domain or serine protease-like domain and activating the polypeptide comprising the serine protease zymogen domain or serine protease-like zymogen domain, said method comprising (a) contacting a first sample comprising a polypeptide or fragment thereof comprising a serine protease zymogen domain or serine protease-like zymogen domain in a pro-form and a candidate ZAP, (b) contacting a second sample comprising a polypeptide or fragment thereof comprising a serine protease zymogen domain or serine protease-like zymogen domain in a mature-form and the candidate ZAP, (c) determining the amount of binding of the candidate ZAP in (a) and (b), wherein greater binding of the candidate ZAP in (a) compared to (b) indicates that the candidate ZAP is capable of specifically binding the polypeptide comprising the serine protease domain or serine protease-like domain and activating the polypeptide comprising the serine protease zymogen domain or serine protease-like zymogen domain.

In some embodiments, the method further comprises assaying the activity of the polypeptide or fragment thereof comprising the serine protease zymogen domain or serine protease-like zymogen domain in a pro-form in the presence of the candidate ZAP and target, wherein activity indicates that the candidate ZAP is capable of specifically binding the polypeptide comprising the serine protease domain or serine protease-like domain and activating the polypeptide comprising the serine protease zymogen domain or serine protease-like zymogen domain. In some embodiments, the target is c-Met. In some embodiments, the polypeptide comprising the serine protease zymogen domain or serine protease-like zymogen domain is HGF, polypeptide or fragment thereof comprising the serine protease zymogen domain or serine protease-like zymogen domain in the pro-form is pro-HGF, and the polypeptide or fragment thereof comprising the serine protease zymogen domain or serine protease-like zymogen domain in the mature-form is mature HGF. In some embodiments, the polypeptide comprising the serine protease zymogen domain or serine protease-like zymogen domain is prethrombin-2 or prothrombin. In some embodiments, the polypeptide comprising the serine protease zymogen domain or serine protease-like zymogen domain is Protein C. In some embodiments, the candidate ZAP is one or more ZAPs or ZAP fusions described herein.

DESCRIPTION OF FIGURES

FIG. 3. Surface representation of the structure of HGF β-chain in complex with Met ((Stamos, J. et al. (2004) *EMBO J* 23: 2325-35), PDB 1SHY). Shown in stick representation are the first 8 residues of the HGF β-chain N-terminus (VVN-GIPTR) (SEQ ID NO:30) inserted into the activation pocket with oxygen, nitrogen, and carbon atoms depicted. The N-terminus of $Val^{495}$ forms a salt bridge with the side chain of $Asp^{672}$ upon insertion into the activation pocket; these correspond to residues 16 and 194 in chymotrypsinogen numbering, respectively.

FIG. 4. Library design and consensus sequences for scHGF β allosteric activation (A) Gene-VIII peptide (SEQ ID NO:117) phage library design. (B) The consensus sequence profile derived after phaging scHGF β is summarized as a logo representation (http://weblogo.threeplusone.com/create.cgi). (C) Activator peptide sequence motif (SEQ ID NO:114) for scHGF β.

FIG. 6. BxPC-3 cell survival assay. (A) HGF (400 ng/ml) can potently stimulate cell survival whereas scHGF (400 ng/ml) has no activity. (B) Peptide titrations of scHGF show allosteric activation of scHGF and elicit cell survival for IVGG.14 (black), IVdG.14 (dark grey), and IVDG.14 (light grey). Both IVGG.14 and IVdG.14 can activate scHGF to similar levels as HGF in panel (A).

FIG. 7. Modified consensus motif (SEQ ID NO:118) for pro-HGF activator peptides. The first 4 positions have been expanded to include residues commonly found at the N-terminus of trypsin/chymotrypsin-like serine protease domains. Position 5 has been modified to include similar hydrophobic residues.

FIG. 8. Crystal structure of the IVGG.14 activator (dark grey) bound to the activation pocket of HGF β V495G (light grey). (A) The overall "S-shape" structure of IVGG.14 is created by two reverse turn motifs allowing for penetration of the activation pocket and binding to the surface of the protein. (B) The combined electrostatic (N-term. salt bridge), hydrophobic (Ile1 and Val2), hydrogen bonding (dashed black lines), and van der Waals (P-W-W-M motif) interactions contribute to specific binding and allosteric activation.

General Techniques

Figure 1:
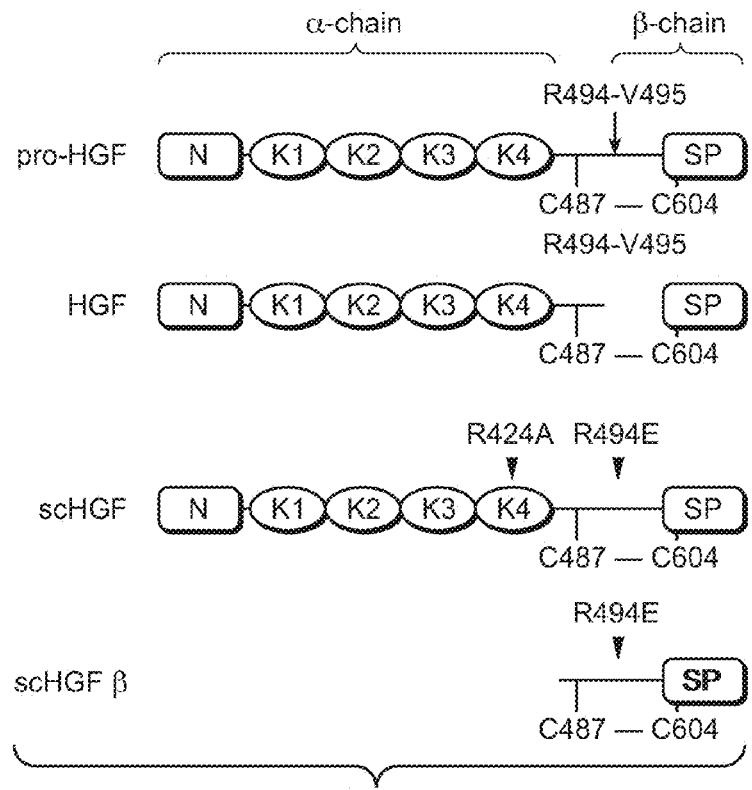
FIG. 1. HGF proteins. Schematic representation of HGF domain topology showing the N-terminal PAN domain (N), four Kringle domains (K1-K4) and the C-terminal trypsin/chymotrypsin-like serine protease domain (SP). Cleavage of the $Arg^{494}$-$Val^{495}$ peptide bond in pro-HGF (arrow) results in activated two-chain HGF. Recombinant proteins containing non-cleavable mutations are denoted by inverted black triangles.
Figure 2:
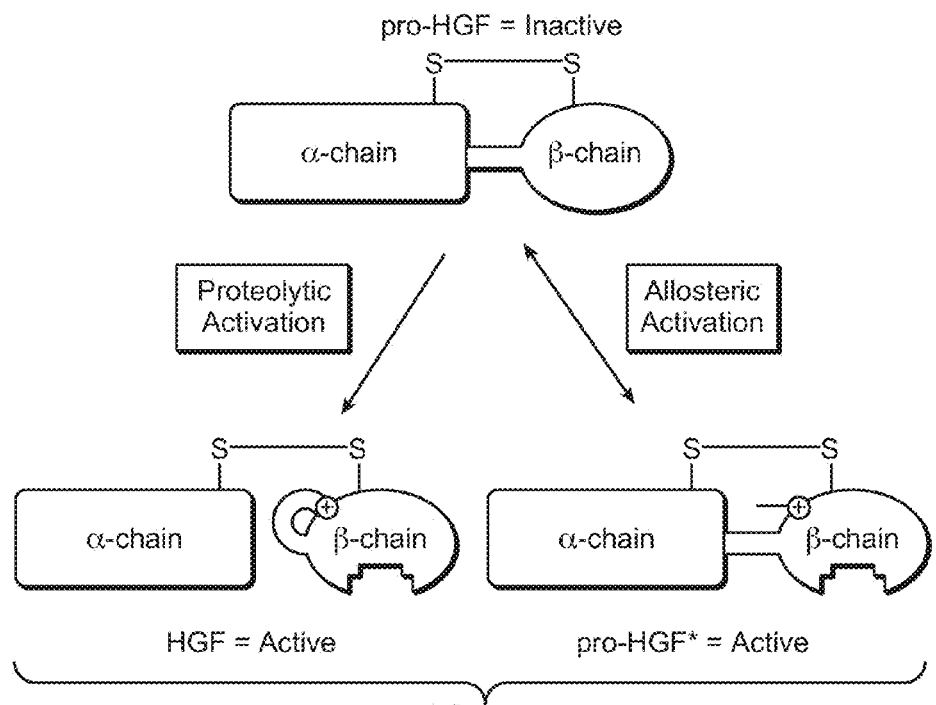
FIG. 2. Model for activation of pro-HGF. Under normal conditions pro-HGF undergoes proteolytic cleavage to the two-chain active form of HGF ("Proteolytic Activation" pathway). In diseases where normal proteolytic activation of HGF is impaired, molecules (stick and circle with "+") that bind pro-HGF that can allosterically induce an active-like form (pro-HGF*) may be useful therapeutics that provide reversible activation of pro-HGF ("Allosteric Activation" pathway).

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988).

Oligonucleotides, polynucleotides, peptides, polypeptides and small molecules employed or described in the present invention can be generated using standard techniques known in the art.

DEFINITIONS

"Isolated," when referred to a molecule, refers to a molecule that has been identified and separated and/or recovered from a component of its natural environment. Contaminant components of its natural environment are materials that interfere with diagnostic or therapeutic uses.

"Control sequences", as used herein, are DNA sequences that enable the expression of an operably-linked coding sequence in a particular host organism. Prokaryotic control sequences include promoters, operator sequences, and ribosome binding sites. Eukaryotic control sequences include promoters, polyadenylation signals, and enhancers.

Nucleic acid is "operably-linked" when it is placed into a functional relationship with another nucleic acid sequence. For example, a promoter or enhancer is operably-linked to a coding sequence if it affects the transcription of the sequence, or a ribosome-binding site is operably-linked to a coding sequence if positioned to facilitate translation. Generally, "operably-linked" means that the DNA sequences being linked are contiguous, and, in the case of a secretory leader, contiguous and in reading phase. However, enhancers do not have to be contiguous.

An "active" polypeptide, or fragments thereof, retains a biological activity of native or naturally-occurring counterpart of the active polypeptide. Biological activity refers to a function mediated by the native or naturally-occurring counterpart of the active polypeptide. For example, binding or protein-protein interaction constitutes a biological activity.

"Affinity" refers to the strength of the sum total of noncovalent interactions between a single binding site of a molecule (e.g., zymogen activating molecule (e.g., ZAP)) and its binding partner (e.g., a polypeptide comprising a serine protease domain or serine protease-like domain e.g., β chain domain of HGF). Unless indicated otherwise, as used herein, "binding affinity" refers to intrinsic binding affinity which reflects a 1:1 interaction between members of a binding pair (e.g., ZAP and β chain domain of HGF). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. In some embodiments, an antibody can be chimeric, human, humanized and/or affinity matured.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The light chains of antibodies from any vertebrate species can be assigned to one of two clearly distinct types, called kappa (κ) and lambda (λ), based on the amino acid sequences of their constant domains.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

An "affinity matured" antibody refers to an antibody with one or more alterations in one or more HVRs, compared to a parent antibody which does not possess such alterations, such alterations resulting in an improvement in the affinity of the antibody for antigen.

An "epitope tagged" polypeptide refers to a chimeric polypeptide fused to a "tag polypeptide". Such tags provide epitopes against which Abs can be made or are available, but do not substantially interfere with polypeptide activity. To reduce anti-tag antibody reactivity with endogenous epitopes, the tag polypeptide is usually unique. Suitable tag polypeptides generally have at least six amino acid residues, usually between about 8 and 50 amino acid residues, preferably between 8 and 20 amino acid residues. Examples of epitope tag sequences include HA from Influenza A virus, GD, and c-myc, poly-His and FLAG.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Zymogen activating molecule" when used herein refers to and includes any molecule which is capable of, directly or indirectly, substantially, fully or partially, inducing, promoting, or enhancing the biological activity of a polypeptide comprising a serine protease domain or serine protease-like domain (e.g., HGF) or activation of the target of the polypeptide comprising a serine protease domain or serine protease-like domain (e.g., c-Met).

"Zymogen activating peptide" or "ZAP" when used herein refers to and includes any peptide which is capable of, directly or indirectly, substantially, fully or partially, inducing, promoting, or enhancing the biological activity of a polypeptide comprising a serine protease domain or serine protease-like domain (e.g., HGF) or activation of the target of the polypeptide comprising a serine protease domain or serine protease-like domain (e.g., c-Met).

A "small molecule" refers to a composition that has a molecular weight of for example less than about 5 kD, less than about 4 kD, and less than 0.6 kD.

The term "peptide" generally refers to a contiguous and relatively short sequence of amino acids linked by peptidyl bonds. Typically, but not necessarily, a peptide has a length of about 2 to about 50 amino acids, about 4-40 amino acids, or about 10-30 amino acids. Although the term "polypeptide" generally refers to longer forms of a peptide, the two terms can be and are used interchangeably in some contexts herein.

The terms "amino acid" and "residue" are used interchangeably herein.

A "region" of a polypeptide is a contiguous sequence of 2 or more amino acids. In other embodiments, a region is at least about any of 3, 5, 10, 15 contiguous amino acids. The "C-terminal region" or variants thereof refers to a region of a polypeptide that includes the 1-5 residues located closest to the C-terminus of the polypeptide. The "N-terminal region" or variants thereof refers to a region of a polypeptide that includes the 1-5 residues located closest to the N-terminus of the polypeptide. An "internal" region of a polypeptide refers to a region of a polypeptide that is located neither at the N-terminus of the polypeptide nor at the C-terminus of the polypeptide.

The terms "hepatocyte growth factor," "scatter factor" and "HGF" refer herein to a native sequence HGF polypeptide, polypeptide variants and fragments of a native sequence polypeptide and polypeptide variants (which are further defined herein). The HGF polypeptide described herein may be that which is isolated from a variety of sources, such as from human tissue types or from another source, or prepared by recombinant or synthetic methods. A "native sequence HGF polypeptide" comprises a polypeptide having the same amino acid sequence as the corresponding HGF polypeptide derived from nature. In one embodiment, a native sequence HGF polypeptide comprises the amino acid sequence of SEQ ID NO:1. See also GenBank: AAA64239.1 and Uniprot: P14210. HGF generally refers herein to any form of HGF including pro-HGF and mature HGF.

93%, 94%, 95%, 96%, 97%, 98%, or 99% amino acid sequence identity, to a native sequence HGF polypeptide sequence as disclosed herein. Ordinarily, HGF variant polypeptides are at least about 10 amino acids in length, alternatively at least about 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600 amino acids in length, or more. Optionally, HGF variant polypeptides will have no more than one conservative amino acid substitution as compared to a native HGF polypeptide sequence, alternatively no more than 2, 3, 4, 5, 6, 7, 8, 9, or 10 conservative amino acid substitution as compared to the native HGF polypeptide sequence.

"Pro-HGF" or "single-chain HGF" refers herein to the secreted single-chain zymogen-like precursor form of HGF. Pro-HGF is capable of binding to c-Met, but cannot activate C-met is a known receptor for HGF through which HGF intracellular signaling is biologically effectuated. Pro-HGF comprises an α-chain domain and a β-chain domain. The term "α-chain domain of pro-HGF" refers to N-terminal residues 1 to 494 of pro-HGF. The α-chain domain of pro-HGF consists of an N-terminal domain (N-domain) followed by four Kringle domains (K1-K4). The N-domain contains a heparin-binding site and is homologous to the N-terminal preactivation peptide (PAP) of plasminogen. The term "β-chain domain of pro-HGF" refers to C-terminal residues 495-728 within pro-HGF The β-chain domain comprises a zymogen form of the serine protease-like region.

"Mature HGF" or "two-chain HGF" refers to the disulfide-linked α/β heterodimer which results from proteolytic conversion of pro-HGF between residue 494 and residue 495. The terms "α-chain of HGF," "HGF α," "HGF α-chain," or

```
                                                           SEQ ID NO: 1
MWVTKLLPALLLQHVLLHLLLLPIAIPYAEGQRKRRNTIHEFKKSAKTTLIKIDPALKIKTKKVN

TADQCANRCTRNKGLPFTCKAFVFDKARKQCLWFPFNSMSSGVKKEFGHEFDLYENKDYIRN

CIIGKGRSYKGTVSITKSGIKCQPWSSMIPHEHSFLPSSYRGKDLQENYCRNPRGEEGGPWCFTS

NPEVRYEVCDIPQCSEVECMTCNGESYRGLMDHTESGKICQRWDHQTPHRHKFLPERYPDKGF

DDNYCRNPDGQPRPWCYTLDPHTRWEYCAIKTCADNTMNDTDVPLETTECIQGQGEGYRGTV

NTIWNGIPCQRWDSQYPHEHDMTPENFKCKDLRENYCRNPDGSESPWCFTTDPNIRVGYCSQIP

NCDMSHGQDCYRGNGKNYMGNLSQTRSGLTCSMWDKNMEDLHRHIFWEPDASKLNENYCR

NPDDDAHGPWCYTGNPLIPWDYCPISRCEGDTTPTIVNLDHPVISCAKTKQLRVVNGIPTRTNIG

WMVSLRYRNKHICGGSLIKESWVLTARQCFPSRDLKDYEAWLGIHDVHGRGDEKCKQVLNVS

QLVYGPEGSDLVLMKLARPAVLDDFVSTIDLPNYGCTIPEKTSCSVYGWGYTGLINYDGLLRV

AHLYIMGNEKCSQHHRGKVTLNESEICAGAEKIGSGPCEGDYGGPLVCEQHKMRMVLGVIVPG

RGCAIPNRPGIFVRVAYYAKWIHKIILTYKVPQS
```

"HGF polypeptide variant", or variations thereof, means a HGF polypeptide, generally an active HGF polypeptide, as defined herein having at least about 80% amino acid sequence identity with any of the native sequence HGF polypeptide sequences as disclosed herein. Such HGF polypeptide variants include, for instance, HGF polypeptides wherein one or more amino acid residues are added, or deleted, at the N- or C-terminus of a native amino acid sequence. Ordinarily, a HGF polypeptide variant will have at least about 80% amino acid sequence identity, alternatively at least about 81%, 82%, 83%, 84%, 85%, 86%, 87%, 88%, 89%, 90%, 91%, 92%, "α-chain" refer to a fragment of HGF comprising C-terminal residues 1-494 of pro-HGF after proteolytic cleavage. The term "β-chain of HGF" refers to a fragment of HGF comprising N-terminal residues 495-728 of pro-HGF after proteolytic cleavage.

The terms "serine protease" or "serine protease-like" refer to polypeptides of the trypsin/chymotrypsin family. The trypsin/chymotrypsin family of serine proteases and protease-like proteins belong to Clan PA and is referred to as Family S1 (also called Family S01) and/or described in the MEROPS database (http://merops.sanger.ac.uk) (Rawlings, N. D. et al. (2010) *Nucleic Acids Res* 38: D227-33).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

A "fusion protein" refers to a polypeptide having two portions covalently linked together, where each of the portions is derived from different proteins. The two portions may be linked directly by a single peptide bond or through a peptide linker containing one or more amino acid residues. Generally, the two portions and the linker will be in reading frame with each other and are produced using recombinant techniques.

A "disorder" or "pathological condition" is any condition that would benefit from treatment with a substance/molecule or method of the invention. This includes chronic and acute disorders or diseases including those pathological conditions, which predispose the mammal to the disorder in question. Non-limiting examples of disorders to be treated herein include tissue regeneration, tissue repair, and wound healing, liver cirrhosis such as chronic liver cirrhosis, fibrosis such as pulmonary fibrosis.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, zymogen activating molecule (e.g., ZAP) are used to delay development of a disease or to slow the progression of a disease.

An "effective amount" of an agent, e.g., a pharmaceutical formulation, refers to an amount effective, at dosages and for periods of time necessary, to achieve the desired therapeutic or prophylactic result. A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "package insert" is used to refer to instructions customarily included in commercial packages of therapeutic products, that contain information about the indications, usage, dosage, administration, combination therapy, contraindications and/or warnings concerning the use of such therapeutic products.

As is understood by one skilled in the art, reference to "about" a value or parameter herein includes (and describes) embodiments that are directed to that value or parameter per se. For example, description referring to "about X" includes description of "X".

It is understood that aspect and embodiments of the invention described herein include "consisting" and/or "consisting essentially of" aspects and embodiments. As used herein, the singular form "a", "an", and "the" includes plural references unless indicated otherwise.

Modulators of Serine Protease Domain or Serine Protease-Like Domain Activation and Signaling Provided herein are zymogen activating molecules (e.g., ZAPs), and methods for identifying and using zymogen activating molecules (e.g., ZAPs), capable of binding a polypeptide comprising a serine protease domain or serine protease-like domain (e.g., HGF) and activates the polypeptide comprising the serine protease zymogen domain or serine protease-like zymogen domain (e.g., HGF). For example, provided herein are zymogen activating molecules (e.g., ZAPs), and methods for identifying and using zymogen activating molecules (e.g., ZAPs), capable of modulating activation of c-Met by HGF, in particular by interacting with the β-chain domain of pro-HGF. One way to modulate the interaction between a polypeptide comprising a serine protease domain or serine protease-like domain (e.g., HGF) and its target (e.g., c-Met) is to activate the polypeptide comprising the serine protease domain or serine protease-like domain (e.g., HGF). Any molecule that activates the polypeptide comprising the serine protease domain or serine protease-like domain (e.g., HGF) can be a candidate zymogen activating molecule. Screening techniques well known to those skilled in the art can identify these molecules. Examples of zymogen activating molecules include: (1) small organic and inorganic compounds, (2) small peptides, (3) antibodies and derivatives, (4) peptides closely related to the polypeptide comprising the serine protease domain or serine protease-like domain (e.g., HGF) (5) nucleic acid aptamers.

In some embodiments of any of the zymogen activating molecules (e.g., ZAPs), and methods for identifying and using zymogen activating molecules (e.g., ZAPs), the polypeptide comprising the serine protease domain or serine protease-like domain is the zymogen or zymogen-like form of any of HGF, Macrophage-Stimulating Protein (MSP), FVII, FIX, FX, FXI, FXII, Glu-Plasminogen, Lys-Plasminogen, Protein C, Prothrombin, Plasma Kallikrein, Prostasin, Enterokinase, Trypsin 2, Trypsin 1, Chymotrypsin B, Hepsin, HGFA, Matriptase, Testisin, Tryptase alpha 1, Tryptase beta 1, Tryptase beta 2, Tryptase gamma, Neurotrypsin, Apolipoprotein A, MASP 1, MASP 2, PSA KLK3, Haptoglobin, Complement C1r, Complement C1s, Urokinase uPA, tPA, or Complement Factor D. In some embodiments, the polypeptide comprising the serine protease domain or serine protease-like domain is HGF, MSP, Hepsin, HGFA, or Matriptase. In some embodiments, the polypeptide comprising the serine protease domain or serine protease-like domain is HGF. In some embodiments, the polypeptide comprising the serine protease zymogen domain or serine protease-like zymogen domain is prethrombin-2 or prothrombin. In some embodiments, the polypeptide comprising the serine protease zymogen domain or serine protease-like zymogen domain is Protein C.

Small Molecule Zymogen Activating Molecules

In some embodiments, the zymogen activating molecule is a small molecule. Small molecules can be useful modulators of a polypeptide comprising a serine protease domain or serine protease-like domain (e.g., HGF) by binding and activating the polypeptide comprising the serine protease zymogen domain or serine protease-like zymogen domain (e.g., HGF). For example, provided herein are small molecules capable of modulating activation of c-Met by HGF, in particular by interacting with the β-chain domain of pro-HGF. Examples of small molecule modulators include small peptides, peptide-like molecules, soluble, and synthetic, non-peptidyl organic or inorganic compounds. Small molecules can be nucleic acids, peptides, polypeptides, peptidomimetics, carbohydrates, lipids or other organic or inorganic molecules. In some embodiments, the small molecule is a ZAP. Libraries of chemical and/or biological mixtures, such as fungal, bacterial, or algal extracts, are known in the art and can be screened with any of the assays. Examples of methods for the synthesis of molecular libraries have been described (Carell et al., *Angewandte Chemie International Edition.* 33:2059-2061 (1994); Carell et al., *Angewandte Chemie International Edition.* 33:2061-2064 (1994); Cho et al., *Science.* 261:1303-5 (1993); DeWitt et al., *Proc Natl Acad Sci USA.* 90:6909-13 (1993); Gallop et al., *J Med Chem.* 37:1233-51 (1994); Zuckermann et al., *J Med Chem.* 37:2678-85 (1994).

Libraries of compounds may be presented in solution (Houghten et al., *Biotechniques.* 13:412-21 (1992)) or on beads (Lam et al., *Nature.* 354:82-84 (1991)), on chips (Fodor et al., *Nature.* 364:555-6 (1993)), bacteria, spores (Ladner et al., U.S. Pat. No. 5,223,409, 1993), plasmids (Cull et al., *Proc Natl Acad Sci USA.* 89:1865-9 (1992)) or on phage (Cwirla et al., *Proc Natl Acad Sci USA.* 87:6378-82 (1990); Devlin et al., *Science.* 249:404-6 (1990); Felici et al., *J Mol Biol.* 222:301-10 (1991); Ladner et al., U.S. Pat. No. 5,223,409, 1993; Scott and Smith, *Science.* 249:386-90 (1990)). A cell-free assay comprises contacting the polypeptide comprising the serine protease zymogen domain or serine protease-like zymogen domain (e.g., HGF) with a known zymogen activating molecule (such as one or more of the ZAPs described herein) to form an assay mixture, contacting the assay mixture with a candidate zymogen activating molecules (e.g., ZAPs), and determining the ability of the candidate compound to interact with the polypeptide comprising the serine protease zymogen domain or serine protease-like zymogen domain (e.g., HGF) or the zymogen activating molecule (such as one or more of the ZAPs described herein), where determining the ability of the test compound to interact with the polypeptide comprising the serine protease zymogen domain or serine protease-like zymogen domain (e.g., HGF) or the zymogen activating molecule (such as one or more of the ZAPs described herein) comprises determining whether a detectable characteristic of the polypeptide comprising the serine protease zymogen domain or serine protease-like zymogen domain (e.g., HGF)/the zymogen activating molecule (such as one or more of the ZAPs described herein) complex is modulated. In some embodiments, the ability of the zymogen activating molecules (e.g., ZAPs) to activate the polypeptide comprising the serine protease zymogen domain or serine protease-like zymogen domain (e.g., HGF) is further assayed. For example, the binding interaction of the polypeptide comprising the serine protease zymogen domain or serine protease-like zymogen domain (e.g., HGF) and the zymogen activating molecule (such as one or more of the ZAPs described herein), as determined by the amount of complex that is formed, can be indicative of whether the test compound is able to modulate the interaction between the polypeptide comprising the serine protease zymogen domain or serine protease-like zymogen domain (e.g., HGF) and the zymogen activating molecule (such as one or more of the ZAPs described herein). Amount of complex can be assessed by methods known in the art, some of which are described herein, for example ELISA (including competitive binding ELISA), yeast two-hybrid and proximity (e.g., fluorescent resonance energy transfer, enzyme-substrate) assays. In some embodiments, the ability of the zymogen activating molecules (e.g., ZAPs) to activate the polypeptide comprising the serine protease zymogen domain or serine protease-like zymogen domain (e.g., HGF) is further assayed as described in Example 3

Zymogen Activating Peptides (ZAPs), Polypeptides, and Antibody Zymogen Activating Molecules In some embodiments, the zymogen activating molecule is a ZAP, polypeptide, or antibody that modulate the biological activity between a polypeptide comprising a serine protease zymogen domain or serine protease-like zymogen domain (e.g., HGF) and its cellular and/or physiological target (e.g., c-Met).

In one aspect, provided herein are ZAPs, wherein the ZAP comprises the amino acid sequence $X_1$-$X_2$-$X_3$-$X_4$-$B_n$ (SEQ ID NO:2), wherein $X_1$ is a large hydrophobic amino acid, $X_2$ is a large hydrophobic amino acid or an aromatic amino acid, $X_3$ is G, D, E, N, D-Gly, D-Asp, D-Glu, D-Asn, or D-Gln Q, $X_4$ is G or A, B is any amino acid, and n is a number between 0-46. Also provided herein are ZAPs, wherein the ZAP consists of or consists essential of the amino acid sequence $X_1$-$X_2$-$X_3$-$X_4$-$B_n$ (SEQ ID NO:31), wherein $X_1$ is a large hydrophobic amino acid, $X_2$ is a large hydrophobic amino acid or an aromatic amino acid, $X_3$ is G, D, E, N, or Q, $X_4$ is G or A, B is any amino acid, and n is a number between 0-46. In some embodiments of any of the ZAPs, wherein $X_1$ is V, $X_3$ is not N (i.e., $X_3$ is G, D, E, or Q) (SEQ ID NO:32).

In some embodiments of any of the ZAPs, $X_1$ is M, L, I, V or NorLeucine (SEQ ID NO:4). In some embodiments, $X_1$ is L, I, or V (SEQ ID NO:5). In some embodiments, $X_1$ is I or V (SEQ ID NO:6). In some embodiments, $X_1$ is I (SEQ ID NO:7).

In some embodiments of any of the ZAPs, $X_2$ is M, L, I, V, NorLeucine, F, or Y (SEQ ID NO:8). In some embodiments, $X_2$ is I, V, L or F (SEQ ID NO:9). In some embodiments, $X_2$ is I or V (SEQ ID NO:10).

In some embodiments of any of the ZAPs, $X_3$ is G, D, or N (SEQ ID NO:11). In some embodiments, $X_3$ is G (SEQ ID NO:12).

In some embodiments of any of the ZAPs, $X_4$ is G (SEQ ID NO:13).

For example, provided herein are ZAPs, wherein the ZAP comprises the amino acid sequence $X_1$-$X_2$-$X_3$-$X_4$-$B_n$ (SEQ ID NO:33), wherein $X_1$ is M, L, I, V or NorLeucine, $X_2$ is M, L, I, V, NorLeucine, F, or Y, $X_3$ is G, D, E, N or Q, $X_4$ is G or A, B is any amino acid, and n is a number between 0-46. Also provided herein are ZAPs, wherein the ZAP consists of or consists essentially of the amino acid sequence $X_1$-$X_2$-$X_3$-$X_4$-$B_n$ (SEQ ID NO:33), wherein $X_1$ is M, L, I, V or NorLeucine, $X_2$ is M, L, I, V, NorLeucine, F, or Y, $X_3$ is G, D, E, N or Q, $X_4$ is G or A, B is any amino acid, and n is a number between 0-46. In some embodiments of any of the ZAPs, wherein $X_1$ is V, $X_3$ is not N (i.e., $X_3$ is G, D, E, or Q) (SEQ ID NO:32).

Provided herein ZAPs, wherein the ZAP comprises the amino acid sequence $X_1$-$X_2$-$X_3$-$X_4$-$B_n$ (SEQ ID NO:34), wherein $X_1$ is L, I, or V, $X_2$ is L, I, V, or F, $X_3$ is G, D, or N, $X_4$ is G or A, B is any amino acid, and n is a number between 0-46. Also provided herein are ZAPs, wherein the ZAP consists of or consists essentially of the amino acid sequence $X_1$-$X_2$-$X_3$-$X_4$-$B_n$ (SEQ ID NO:34), wherein $X_1$ is L, I, or V, $X_2$ is L, I, V, or F, $X_3$ is G, D, or N, $X_4$ is G or A, B is any amino acid, and n is a number between 0-46. In some embodiments of any of the ZAPs, wherein $X_1$ is V, $X_3$ is not N (i.e., $X_3$ is G, D, E, or Q) (SEQ ID NO:35).

Further provided herein ZAPs, wherein the ZAP comprises the amino acid sequence $X_1$-$X_2$-$X_3$-$X_4$-$B_n$ (SEQ ID NO:36), wherein $X_1$ is I, $X_2$ is I or V, $X_3$ is G, $X_4$ is G, B is any amino acid, and n is a number between 0-46. Provided herein are also ZAPs, wherein the ZAP consists of or consists essentially of the amino acid sequence $X_1$-$X_2$-$X_3$-$X_4$-$B_n$ (SEQ ID NO:36), wherein $X_1$ is I, $X_2$ is I or V, $X_3$ is G, $X_4$ is G, B is any amino acid, and n is a number between 0-46.

In some embodiments of any of the ZAPs, the ZAP comprises, consists of, or consists essentially of the amino acid sequence $X_1$-$X_2$-$X_3$-$X_4$-$B_n$ (SEQ ID NO:2), $X_1$-$X_2$-$X_3$-$X_4$ (SEQ ID NO:14) are IVGG (SEQ ID NO:15), IVDG (SEQ ID NO:16), IVdG, IVGG (SEQ ID NO:17), IIGG (SEQ ID NO:18), VVNG (SEQ ID NO:19), VVGG (SEQ ID NO:20), IVGG (SEQ ID NO:21), LIDG (SEQ ID NO:22), IVEG (SEQ ID NO:23), ITGG (SEQ ID NO:24), IVNG (SEQ ID NO:25), IFNG (SEQ ID NO:26), IYGG (SEQ ID NO:27), ILGG (SEQ ID NO:28), or IKGG (SEQ ID NO:29), wherein d is D-aspartic acid. In some embodiments of any of the ZAPs, wherein the ZAP comprises, consists of, or consists essentially of the amino acid sequence $X_1$-$X_2$-$X_3$-$X_4$-$B_n$ (SEQ ID NO:2), $X_1$-$X_2$-$X_3$-$X_4$ (SEQ ID NO:14) are IVGG (SEQ ID NO:15), IVDG (SEQ ID NO:16), IVdG, IVGG (SEQ ID NO:17), IIGG (SEQ ID NO:18), VVGG (SEQ ID NO:20), IVGG (SEQ ID NO:21), LIDG (SEQ ID NO:22), IVEG (SEQ ID NO:23), ITGG (SEQ ID NO:24), IVNG (SEQ ID NO:25), IFNG (SEQ ID NO:26), IYGG (SEQ ID NO:27), ILGG (SEQ ID NO:28), or IKGG (SEQ ID NO:29), wherein d is D-aspartic acid. In some embodiments of any of the ZAPs, wherein the ZAP comprises, consists of, or consists essentially of the amino acid sequence $X_1$-$X_2$-$X_3$-$X_4$-$B_n$ (SEQ ID NO:2), $X_1$-$X_2$-$X_3$-$X_4$ (SEQ ID NO:14) are IVGG (SEQ ID NO:15), IVDG (SEQ ID NO:16), IVdG, IVGG (SEQ ID NO:17), or IIGG (SEQ ID NO:18), wherein d is D-aspartic acid. In some embodiments of any of the ZAPs, the ZAP does not comprise, consist, or consist essentially of VVNG (SEQ ID NO:19).

In some embodiments of any of the ZAPs, the ZAP further comprises, consists of, or consists essentially of the amino acid sequence $X_5$-$X_6$-$X_7$-$X_8$-$X_9$-$X_{10}$-$X_{11}$, (SEQ ID NO:37), wherein $X_5$ is Y or F, $X_6$ is P, $X_7$ is W, $X_8$ is W, $X_9$ is M, I, or V, $X_{10}$ is D or E, $X_{11}$ is V or A. In some embodiments of any of the ZAPs, the ZAP further comprises, consists of, or consists essentially of the amino acid sequence $X_5$-$X_6$-$X_7$-$X_8$-$X_9$-$X_{10}$-$X_{11}$ (SEQ ID NO:119), wherein $X_5$ is Y, C, D, or F, $X_6$ is Y or P, $X_7$ is W or Y, $X_8$ is W or D, $X_9$ is M, I, or V, $X_{10}$ is D, P, or E, $X_{11}$ is V, H, R, I or A. In some embodiments of any of the ZAPs, the ZAP further comprises, consists of, or consists essentially of the amino acid sequence $X_5$-$X_6$-$X_7$-$X_8$-$X_9$-$X_{10}$-$X_{11}$-$X_{12}$-$X_{13}$-$X_{14}$-$X_{15}$ (SEQ ID NO:120), wherein $X_5$ is Y, C, D, or S, $X_6$ is P, $X_7$ is W or Y, $X_8$ is W, $X_9$ is M, I, or V, $X_{10}$ is P, D or E, $X_{11}$ is H, R, V or A, $X_{12}$ is absent, P, or E, $X_{13}$ is G or E, $X_{14}$ is D, C, or S, and $X_{15}$ is A or I. In some embodiments of any of the ZAPs, the ZAP further comprises, consists of, or consists essentially of the amino acid sequence $X_5$-$X_6$-$X_7$-$X_8$-$X_9$-$X_{10}$-$X_{11}$ (SEQ ID NO:121), $X_{12}$-$X_{13}$-$X_{14}$-$X_{15}$ (SEQ ID NO:122), wherein $X_5$ is any amino acid, $X_6$ is P, $X_7$ is any amino acid, $X_8$ is W, $X_9$-$X_{15}$ is any amino acid. In some embodiments, $X_5$ is C. In some embodiments, $X_{14}$ is C.

In some embodiments of any of the ZAPs, n is a number greater than about any of 1, 2, 3, 4, 5, 6, 7, 8, 9, 10, 11, 15, 20, 25, or 30. In some embodiments of any of the ZAPs, n is a number less than about any of 5, 6, 7, 8, 9, 10, 11, 12, 13, 14, 15, 20, 25, or 30. In some embodiments of any of the ZAPs, n is about 1, 2, 3, 4, 5, 6, 7, 8, 9, 10, 11, 12, 13, 14, or 15. In some embodiments, n is about 5, 6, 7, or 8. In some embodiments of any of the ZAPs, n is between about any of 3-15, 3-7, 3-10, 3-12, 5-12, or 5-10.

In some embodiments of any of the ZAPs, wherein the ZAP comprises, consists of, or consists essentially of the amino acid sequence IVGGYPWWMDV (SEQ ID NO:38), IVDGYPWWMDV (SEQ ID NO:39), IVdGYPWWMDV, IVGGYhyPWWMDV (SEQ ID NO:40), IIGGYhyPWWMDV (SEQ ID NO:41), VVNGIPTRTNI (SEQ ID NO:42), VVGGHPGNSPW (SEQ ID NO:43), IVGGKVCPKGE (SEQ ID NO:44), VVGGEDAKPGQ (SEQ ID NO:45), IVGGQECKDGE (SEQ ID NO:46), IVGGTASVRGE (SEQ ID NO:47), VVGGLVALRGA (SEQ ID NO:48), VVGGCVAHPHS (SEQ ID NO:49), VVGGCVAHPHS (SEQ ID NO:50), LIDGKMTRRGD (SEQ ID NO:51), IVEGSDAEIGM (SEQ ID NO:52), IVGGTNSSWGE (SEQ ID NO:53), ITGGSSAVAGQ (SEQ ID NO:54), IVGGSNAKEGA (SEQ ID NO:55), IVGGYICEENS (SEQ ID NO:56), IVGGYNCEENS (SEQ ID NO:57), IVNGEDAVPGS (SEQ ID NO:58), IVGGRDTSLGR (SEQ ID NO:59), IIGGSSSLPGS (SEQ ID NO:60), VVGGTDADEGE (SEQ ID NO:61), IVGGEDAELGR (SEQ ID NO:62), IVGGQEAPRSK (SEQ ID NO:63), IVGGQEAPRSK (SEQ ID NO:64), IVGGQEAPRSK (SEQ ID NO:65), IVGGHAAPAGA (SEQ ID NO:66), IIGGKNSLRGG (SEQ ID NO:67), IVGGCVAHPHS (SEQ ID NO:68), IFNGRPAQKGT (SEQ ID NO:69), IYGGQKAKPGD (SEQ ID NO:70), IVGGWECEKHS (SEQ ID NO:71), ILGGHLDAKGS (SEQ ID NO:72), IIGGQKAKMGN (SEQ ID NO:73), IIGGSDADIKN (SEQ ID NO:74), IIGGEFTTIEN (SEQ ID NO:75), IKGGLFADIAS (SEQ ID NO:76), and/or ILGGREAEAHA (SEQ ID NO:77), wherein d is D-aspartic acid and hyP is hydroxyproline. In some embodiments of any of the ZAPs, wherein the ZAP comprises, consists of, or consists essentially of the amino acid sequence IVGGYPWWMDV (SEQ ID NO:38), IVDGYPWWMDV (SEQ ID NO:39), IVdGYPWWMDV, IVGGYhyPWWMDV (SEQ ID NO:40), IIGGYhyPWWMDV (SEQ ID NO:41), VVGGHPGNSPW (SEQ ID NO:43), IVGGKVCPKGE (SEQ ID NO:44), VVGGEDAKPGQ (SEQ ID NO:45), IVGGQECKDGE (SEQ ID NO:46), IVGGTASVRGE (SEQ ID NO:47), VVGGLVALRGA (SEQ ID NO:48), VVGGCVAHPHS (SEQ ID NO:49), VVGGCVAHPHS (SEQ ID NO:50), LIDGKMTRRGD (SEQ ID NO:51), IVEGSDAEIGM (SEQ ID NO:52), IVGGTNSSWGE (SEQ ID NO:53), ITGGSSAVAGQ (SEQ ID NO:54), IVGGSNAKEGA (SEQ ID NO:55), IVGGYICEENS (SEQ ID NO:56), IVGGYNCEENS (SEQ ID NO:57), IVNGEDAVPGS (SEQ ID NO:58), IVGGRDTSLGR (SEQ ID NO:59), IIGGSSSLPGS (SEQ ID NO:60), VVGGTDADEGE (SEQ ID NO:61), IVGGEDAELGR (SEQ ID NO:62), IVGGQEAPRSK (SEQ ID NO:63), IVGGQEAPRSK (SEQ ID NO:64), IVGGQEAPRSK (SEQ ID NO:65), IVGGHAAPAGA (SEQ ID NO:66), IIGGKNSLRGG (SEQ ID NO:67), IVGGCVAHPHS (SEQ ID NO:68), IFNGRPAQKGT (SEQ ID NO:69), IYGGQKAKPGD (SEQ ID NO:70), IVGGWECEKHS (SEQ ID NO:71), ILGGHLDAKGS (SEQ ID NO:72), IIGGQKAKMGN (SEQ ID NO:73), IIGGSDADIKN (SEQ ID NO:74), IIGGEFTTIEN (SEQ ID NO:75), IKGGLFADIAS (SEQ ID NO:76), and/or ILGGREAEAHA (SEQ ID NO:77), wherein d is D-aspartic acid and hyP is hydroxyproline. In some embodiments of any of the ZAPs, wherein the ZAP comprises, consists of, or consists essentially of the amino acid sequence IVGGYPWWMDV (SEQ ID NO:38), IVDGYPWWMDV (SEQ ID NO:39), IVdGYPWWMDV, IVGGYhyPWWMDV (SEQ ID NO:40), and/or IIGGYhyPWWMDV (SEQ ID NO:41), wherein d is D-aspartic acid and hyP is hydroxyproline. In some embodiments of any of the ZAPs, the ZAP does not comprise, consist of, or consist essentially of VVNGIPTRTNI (SEQ ID NO:42). In some embodiments of any of the ZAPs, wherein the ZAP comprises, consists of, or consists essentially of the amino acid sequence IIGGDPYWVPHPGDA (SEQ ID NO:123). In some embodiments of any of the ZAPs, wherein the ZAP comprises, consists of, or consists essentially of the amino acid sequence IIGGCPYWMDREECI (SEQ ID NO:124). In some embodiments of any of the ZAPs, wherein the ZAP comprises, consists of, or consists essentially of the amino acid sequence IIGGSPYWMDREESI (SEQ ID NO:125). In some embodiments of any of the ZAPs, wherein the ZAP comprises, consists of, or consists essentially of the amino acid sequence IVGGCYWWVPI (SEQ ID NO:126). In some embodiments of any of the ZAPs, wherein the ZAP comprises, consists of, or consists essentially of the amino acid sequence IVGGDPYWVPHPGDA (SEQ ID NO:127).

In some embodiments of any of the ZAPs, wherein the ZAP comprises, consists of, or consists essentially of the amino acid sequence IVGGDYWWVPI (SEQ ID NO:128), IVGGDFYSSYW (SEQ ID NO:129), IVGGDGMPWWI (SEQ ID NO:130), IVGGYPWWMDV (SEQ ID NO:38), IVGGDPVYVLY (SEQ ID NO:131), IVGGYPWWITG (SEQ ID NO:132), IVGGYPWWVDV (SEQ ID NO:133), IVGGYPAWMEY (SEQ ID NO:134), IVGGSDFPWWV (SEQ ID NO:135), IVGGLWEMWVT (SEQ ID NO:136), IVGGEPAYWYW (SEQ ID NO:137), IVGGHPMSPFS (SEQ ID NO:138), IVGGDPWWFVS (SEQ ID NO:139), IVGGPHKAFLL (SEQ ID NO:140), IVGGEPVWYVW (SEQ ID NO:141), IVGGYPVYFLN (SEQ ID NO:142), IVGGEPVYYVT (SEQ ID NO:143), IVGGCKRSYWE (SEQ ID NO:144), IVGGTRCNDWI (SEQ ID NO:145), IVGGSACLIAM (SEQ ID NO:146), IVGGVRCWVSN (SEQ ID NO:147), IVGGLDVEYEL (SEQ ID NO:148), IVGGMRLCGYI (SEQ ID NO:149), IVGGNKIWSVS (SEQ ID NO:150), IVGGDYYWVVQ (SEQ ID NO:151), IVGGKWQRKRV (SEQ ID NO:152), and/or IVGGFVFWCDQ (SEQ ID NO:153).

In some embodiments of any of the ZAPs, wherein the ZAP comprises, consists of, or consists essentially of the amino acid sequence IIGGDPVWDITYTYA (SEQ ID NO:174), IIGGDPYWYPHPGTV (SEQ ID NO:154), IVGGDPYWVPHPGDA (SEQ ID NO:127), IIGGEPAWVWYEDCM (SEQ ID NO:155), IIGGDPWWTPHPSFV (SEQ ID NO:156), IVGGDPWWVDHMYLT (SEQ ID NO:157), IVGGEPVWVPWCVYD (SEQ ID NO:158), IIGGDPVWVLSTECG (SEQ ID NO:159), IIGGEPWWVDFVEDY (SEQ ID NO:160), IIGGCPYWMDREECI (SEQ ID NO:124), and/or IVGGCPYWMDREECL (SEQ ID NO:161).

In some embodiments of any of the ZAPs, wherein the ZAP comprises, consists of, or consists essentially of the amino acid sequence IIGGCPTYCMSTGCA (SEQ ID NO:162), IIGGCPLDDGVARCL (SEQ ID NO:163), IIGGCPIDGRVWACG (SEQ ID NO:164), IIGGCPAAVSNSVCY (SEQ ID NO:165), IIGGCPAGSELAVCT (SEQ ID NO:166), and/or IIGGCPLYCMITGCA (SEQ ID NO:167).

In some embodiments of any of the ZAPs, wherein the ZAP is linear. In some embodiments of any of the ZAPs, wherein the ZAP is cyclic. In some embodiments, the ZAP comprises a disulfide bond. In some embodiments, the ZAP comprises an intramolecular disulfide bond. In some embodiments, the ZAP comprises an intramolecular disulfide bond between Cys-5 and Cys-14.

In some embodiments of any of the ZAPs, the ZAP specifically binds a polypeptide comprising a serine protease domain or serine protease-like domain and activates the polypeptide comprising the serine protease zymogen domain or serine protease-like zymogen domain. In some embodiments, the polypeptide comprising the serine protease domain or serine protease-like domain is the zymogen or zymogen-like form of any of HGF, MSP, FVII, FIX, FX, FXI, FXII, Glu-Plasminogen, Lys-Plasminogen, Protein C, Prothrombin, Plasma Kallikrein, Prostasin, Enterokinase, Trypsin 2, Trypsin 1, Chymotrypsin B, Hepsin, HGFA, Matriptase, Testisin, Tryptase alpha 1, Tryptase beta 1, Tryptase beta 2, Tryptase gamma, Neurotrypsin, Apolipoprotein A, MASP 1, MASP 2, PSA KLK3, Haptoglobin, Complement C1r, Complement C1s, Urokinase uPA, tPA, or Complement Factor D. In some embodiments, the polypeptide comprising the serine protease domain or serine protease-like domain is HGF, MSP, Hepsin, HGFA, or Matriptase. In some embodiments, the polypeptide comprising the serine protease zymogen domain or serine protease-like zymogen domain is prethrombin-2 or prothrombin. In some embodiments, the polypeptide comprising the serine protease zymogen domain or serine protease-like zymogen domain is Protein C. In some embodiments, the polypeptide comprising the serine protease zymogen domain or serine protease-like zymogen domain is MSP. In some embodiments, the ZAP allosterically activates the polypeptide comprising the serine protease zymogen domain or serine protease-like zymogen domain.

In some embodiments of any of the ZAPs, the polypeptide comprising the serine protease domain or serine protease-like domain is HGF. In some embodiments, the ZAP specifically binds to the β-chain domain of pro-HGF and activates HGF signaling through c-Met. In some embodiments, the ZAP specifically binds to the activation pocket of the β-chain domain of pro-HGF. In some embodiments, the ZAP allosterically activates HGF.

In some embodiments of any of the ZAPs, the ZAP has a binding affinity as determined by a Kd to the polypeptide comprising the serine protease domain or serine protease-like domain of less than about any of 1.0 mM, 500 µM, 100 µM, 50 µM, 25 µM, 10 µM, 5 µM, or 1 µM. In some embodiments of any of the ZAPs, the ZAP has a binding affinity as determined by a Kd to HGF of less than about any of 1.0 mM, 500 µM, 100 µM, 50 µM, 25 µM, 10 µM, 5 µM, or 1 µM. In some embodiments of any of the ZAPs, the ZAP has a binding affinity as determined by a Kd to β-chain domain of pro-HGF of less than about any of 1.0 mM, 500 µM, 100 µM, 50 µM, 25 µM, 10 µM, 5 µM, or 1 µM. In some embodiments, the binding affinity as determined by a Kd is determined by any method known in the art, in particular the method described in Example 2.

In some embodiments of any of the ZAPs, the ZAP may be isolated. In some embodiments of any of the ZAPs, the ZAP is a synthetic ZAP, a polypeptide chain created through chemical synthesis.

In some embodiments, the zymogen activating molecules (such as ZAPs) can be isolated from cells or tissue sources by an appropriate purification scheme using standard protein purification techniques. In another embodiment, the zymogen activating molecules (such as ZAPs) are produced by recombinant DNA techniques. Alternative to recombinant expression, zymogen activating molecules (such as ZAPs) can be synthesized chemically using standard peptide synthesis techniques.

Also provided are a mutant or variant zymogen activating molecules (such as ZAPs) any of which residues may be changed from the corresponding residues of these zymogen activating molecules (such as ZAPs), while still encoding a peptide that maintains modulatory activity. In one embodiment, a variant of a zymogen activating molecules (such as ZAPs)/polypeptide comprising the serine protease domain or serine protease-like domain (e.g., HGF)/target (e.g., c-Met) has at least 50%, 60%, 70%, 80%, 90%, 95%, 98%, 99% amino acid sequence identity with the sequence of a reference binder peptide/polypeptide/ligand. In general, the variant exhibits substantially the same or greater binding affinity than the reference zymogen activating molecules (such as ZAPS)/polypeptide comprising the serine protease domain or serine protease-like domain (e.g., HGF)/target (e.g., c-Met), e.g., at least 0.75×, 0.8×, 0.9×, 1.0×, 1.25× or 1.5× the binding affinity of the reference zymogen activating molecules (such as ZAPS)/polypeptide comprising the serine protease domain or serine protease-like domain (e.g., HGF)/target (e.g., c-Met), based on an art-accepted binding assay quantitation unit/metric.

In general, variants herein include variants in which residues at a particular position in the sequence have been substituted by other amino acids, and further includes the possibility of inserting an additional residue or residues between two residues of the parent protein/peptide as well as the possibility of deleting one or more residues from the parent sequence or adding one or more residues to the parent sequence. Any amino acid substitution, insertion, or deletion is encompassed by the invention. In favorable circumstances, the substitution is a conservative substitution as described herein.

In some embodiments, the zymogen activating molecules (e.g., ZAP) is an isolated polypeptide. Contaminant components include materials that would typically interfere with diagnostic or therapeutic uses for the polypeptide, and may include enzymes, hormones, and other proteinaceous or non-proteinaceous materials. Preparations having preferably less than about 30% by dry weight of non-desired contaminating material (contaminants), preferably less than about 20%, about 10%, and preferably less than about 5% contaminants are considered to be substantially isolated. An isolated, recombinantly-produced peptide/polypeptide or biologically active portion thereof is preferably substantially free of culture medium, i.e., culture medium represents preferably less than about 20%, preferably less than about 10%, and preferably less than about 5% of the volume of a peptide/polypeptide preparation. Examples of contaminants include cell debris, culture media, and substances used and produced during in vitro synthesis of the peptide/polypeptide.

Conservative substitutions of peptides/polypeptides are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the peptide/polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Non-conservative substitutions will entail exchanging a member of one of these classes for another class. Amino acids may be grouped according to common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe;
 (7) large hydrophobic: Norleucine, Met, Val, Leu, Ile;

In further embodiments, peptides or polypeptides of the invention may comprise one or more non-naturally occurring or modified amino acids. A "non-naturally occurring amino acid residue" refers to a residue, other than those naturally occurring amino acid residues listed above, which is able to covalently bind adjacent amino acid residues(s) in a polypeptide chain. Non-natural amino acids include, but are not limited to homo-lysine, homo-arginine, homo-serine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, citrulline, pentylglycine, pipecolic acid and thioproline. Modified amino acids include natural and non-natural amino acids which are chemically blocked, reversibly or irreversibly, or modified on their N-terminal amino group or their side chain groups, as for example, N-methylated D and L amino acids, side chain functional groups that are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide and a modified amino acid of alanine. Additional non-natural and modified amino acids, and methods of incorporating them into proteins and peptides, are known in the art (see, e.g., Sandberg et al., (1998) *J. Med. Chem.* 41: 2481-91; Xie and Schultz (2005) *Curr. Opin. Chem. Biol.* 9: 548-554; Hodgson and Sanderson (2004) *Chem. Soc. Rev.* 33: 422-430.

Variants of antibody and/or ZAP modulators of the polypeptide comprising the serine protease domain or serine protease-like domain (e.g., HGF) can also be made based on information known in the art, without substantially affecting the activity of antibody and/or ZAP. For example, antibody variants and/or ZAP variants can have at least one amino acid residue in the antibody molecule and/or ZAP replaced by a different residue. For antibodies, the sites of greatest interest for substitutional mutagenesis generally include the hypervariable regions, but framework region (FR) alterations are also contemplated.

For antibodies, one type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody and/or ZAP are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody and/or ZAP.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In one embodiment, the Fc region variant may display altered neonatal Fc receptor (FcRn) binding affinity. Such variant Fc regions may comprise an amino acid modification at any one or more of amino acid positions 238, 252, 253, 254, 255, 256, 265, 272, 286, 288, 303, 305, 307, 309, 311, 312, 317, 340, 356, 360, 362, 376, 378, 380, 382, 386, 388, 400, 413, 415, 424, 433, 434, 435, 436, 439 or 447 of the Fc region, wherein the numbering of the residues in the Fc region is that of the EU index as in Kabat. Fc region variants with reduced binding to an FcRn may comprise an amino acid modification at any one or more of amino acid positions 252, 253, 254, 255, 288, 309, 386, 388, 400, 415, 433, 435, 436, 439 or 447 of the Fc region, wherein the numbering of the residues in the Fc region is that of the EU index as in Kabat. The above-mentioned Fc region variants may, alternatively, display increased binding to FcRn and comprise an amino acid modification at any one or more of amino acid positions 238, 256, 265, 272, 286, 303, 305, 307, 311, 312, 317, 340, 356, 360, 362, 376, 378, 380, 382, 413, 424 or 434 of the Fc region, wherein the numbering of the residues in the Fc region is that of the EU index as in Kabat.

The Fc region variant with reduced binding to an Fc(R may comprise an amino acid modification at any one or more of amino acid positions 238, 239, 248, 249, 252, 254, 265, 268, 269, 270, 272, 278, 289, 292, 293, 294, 295, 296, 298, 301, 303, 322, 324, 327, 329, 333, 335, 338, 340, 373, 376, 382, 388, 389, 414, 416, 419, 434, 435, 437, 438 or 439 of the Fc region, wherein the numbering of the residues in the Fc region is that of the EU index as in Kabat.

For example, the Fc region variant may display reduced binding to an Fc(RI and comprise an amino acid modification at any one or more of amino acid positions 238, 265, 269, 270, 327 or 329 of the Fc region, wherein the numbering of the residues in the Fc region is that of the EU index as in Kabat.

The Fc region variant may display reduced binding to an Fc(RII and comprise an amino acid modification at any one or more of amino acid positions 238, 265, 269, 270, 292, 294, 295, 298, 303, 324, 327, 329, 333, 335, 338, 373, 376, 414, 416, 419, 435, 438 or 439 of the Fc region, wherein the numbering of the residues in the Fc region is that of the EU index as in Kabat.

The Fc region variant of interest may display reduced binding to an Fc(RIII and comprise an amino acid modification at one or more of amino acid positions 238, 239, 248, 249, 252, 254, 265, 268, 269, 270, 272, 278, 289, 293, 294, 295, 296, 301, 303, 322, 327, 329, 338, 340, 373, 376, 382, 388, 389, 416, 434, 435 or 437 of the Fc region, wherein the numbering of the residues in the Fc region is that of the EU index as in Kabat.

Fc region variants with altered (i.e. improved or diminished) C1q binding and/or Complement Dependent Cytotoxicity (CDC) are described in WO99/51642. Such variants may comprise an amino acid substitution at one or more of amino acid positions 270, 322, 326, 327, 329, 331, 333 or 334 of the Fc region. See, also, Duncan & Winter Nature 322:738-40 (1988); U.S. Pat. No. 5,648,260; U.S. Pat. No. 5,624,821; and WO94/29351 concerning Fc region variants.

Zymogen Activating Peptide Fusions

Further provided herein are zymogen activating fusions comprising any of the zymogen activating molecules (e.g., ZAPs) described herein conjugated to a carrier. For example, in some embodiments, the ZAP of any of the zymogen activating fusions comprises the amino acid sequence $X_1$-$X_2$-$X_3$-$X_4$-$B_n$ (SEQ ID NO:2), wherein $X_1$ is a large hydrophobic amino acid, $X_2$ is a large hydrophobic amino acid or an aromatic amino acid, $X_3$ is G, D, E, N, Q, D-Gly, D-Asp, D-Glu, D-Asn, or D-Gln, $X_4$ is G or A, B is any amino acid, and n is a number between 0-46. In some embodiments, the ZAP of any of the zymogen activating fusions consists of the amino acid sequence $X_1$-$X_2$-$X_3$-$X_4$-$B_n$ (SEQ ID NO:31), wherein $X_1$ is a large hydrophobic amino acid, $X_2$ is a large hydrophobic amino acid or an aromatic amino acid, $X_3$ is G, D, E, N or Q, $X_4$ is G or A, B is any amino acid, and n is a number between 0-46. In some embodiments of any of the ZAPs, wherein $X_1$ is V, $X_3$ is not N ($X_3$ is G, D, E, or Q) (SEQ ID NO:32). In some embodiments, $X_1$ is M, L, I, V or NorLeucine (SEQ ID NO:4). In some embodiments, $X_1$ is L, I, or V (SEQ ID NO:5). In some embodiments, $X_1$ is I (SEQ ID NO:7). In some embodiments, $X_2$ is M, L, I, V, NorLeucine, F, or Y (SEQ ID NO:8). In some embodiments, $X_2$ is I, V, L or F (SEQ ID NO:9). In some embodiments, $X_2$ is I or V (SEQ ID NO:10). In some embodiments, $X_3$ is G, D, or N (SEQ ID NO:11). In some embodiments, $X_3$ is G (SEQ ID NO:12). In some embodiments, $X_4$ is G (SEQ ID NO:13). In some embodiments, the ZAP binds the β-chain domain of pro-HGF and activates c-Met signaling. In some embodiments, the ZAP has a binding affinity as determined by a Kd of less than about 100 μM (for example less than about 25 μM).

In some embodiments of any of the zymogen activating fusions, the carrier to which the zymogen activating molecules (e.g., ZAPs) is conjugated is a biodegradable polymer. Biodegradable or biocompatible polymers can be used, such as ethylene vinyl acetate, polyanhydrides, polyglycolic acid, polyorthoesters, polylactic acid, PEG, polylactide, polyglycolide, polycaprolactone, carbohydrates, polypeptides, collagen, starches, cellulose, chitins, lignins, and co-polymers thereof. Such materials can be obtained commercially from ALZA Corporation (Mountain View, Calif.) and NOVA Pharmaceuticals, Inc. (Lake Elsinore, Calif.), or prepared by one of skill in the art. Liposomal suspensions can also be used as pharmaceutically acceptable carriers. These can be prepared according to methods known to those skilled in the art, such as in (Eppstein et al., U.S. Pat. No. 4,522,811, 1985). In some embodiments, the carrier is a polypeptide. In some embodiment, the polypeptide is albumin. In some embodiments, the polypeptide is an Fc. In some embodiments, the carrier is PEG.

In some embodiments, the carrier improves improve stability and half-life. In some embodiments, the carrier is a protein. In some embodiments, the protein carrier is serum albumin, and the antibody constant region (Fc). In some embodiments, the protein carrier is linked (e.g., recombinantly fused) to the C-terminus of the zymogen activating peptide sequence. In some embodiments, the carrier is chemically conjugated. In some embodiments, the carrier is polyethylene glycol (PEG) compound, pegylated peptides, and proteins are well known to have longer a half-life in vivo. In addition, small modular proteins, such as an Ig-like protein fold, may also be fused to the C-terminus of the ZAP to provide an additional protein surface for binding affinity enhancements.

In some embodiments of any of the zymogen activating fusions, the carrier is conjugated to the C-terminus of the zymogen activating molecules (e.g., ZAPs). In some embodiments of any of the zymogen activating fusions, the carrier is not conjugated to the N-terminus of the zymogen activating molecules (e.g., ZAPs).

In some embodiments of any of the zymogen activating fusions, the carrier is covalently conjugated to the zymogen activating molecule (e.g., ZAP). In some embodiments of any of the zymogen activating fusions, the carrier is directly conjugated to the zymogen activating molecule (e.g., ZAP). In some embodiments of any of the zymogen activating fusions, the carrier is covalently conjugated to the zymogen activating molecule (e.g., ZAP) via a linker sequence. In some embodiments, the carrier is conjugated as a fusion protein with the zymogen activating molecule (e.g., ZAP).

In some embodiments of any of the zymogen activating fusions, the conjugation of the zymogen activating molecule (e.g., ZAP) to the carrier increases the half-life and/or bioavailability of the zymogen activating molecule (e.g., ZAP) compared to the zymogen activating molecule (e.g., ZAP) unconjugated to the carrier.

Vector Construction

Polynucleotide sequences encoding the antibody, peptide, and/or polypeptides described herein can be obtained using standard synthetic and/or recombinant techniques. Desired polynucleotide sequences may be isolated and sequenced from appropriate source cells. Source cells for antibodies, peptides, and/or polypeptides would include antibody, peptide, and/or polypeptide producing cells such as hybridoma cells. Alternatively, polynucleotides can be synthesized using nucleotide synthesizer or PCR techniques. Once obtained, sequences encoding the antibody, peptide, and/or polypeptide are inserted into a recombinant vector capable of replicating and expressing heterologous polynucleotides in a host cell. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication (in particular when the vector is inserted into a prokaryotic cell), a selection marker gene, a promoter, a ribosome binding site (RBS), a signal sequence, the heterologous nucleic acid insert and a transcription termination sequence.

In general, plasmid vectors containing replicon and control sequences which are derived from a species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

Either constitutive or inducible promoters can be used in the present invention, in accordance with the needs of a particular situation, which can be ascertained by one skilled in the art. A large number of promoters recognized by a variety of potential host cells are well known. The selected promoter can be operably linked to cistron DNA encoding a polypeptide described herein by removing the promoter from the source DNA via restriction enzyme digestion and inserting the isolated promoter sequence into the vector of choice. Both the native promoter sequence and many heterologous promoters may be used to direct amplification and/or expression of the target genes. However, heterologous promoters are preferred, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) *Cell* 20: 269) using linkers or adaptors to supply any required restriction sites.

In some embodiments, each cistron within a recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP.

Prokaryotic host cells suitable for expressing polypeptides include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. Preferably, gram-negative cells are used. Preferably the host cell should secrete minimal amounts of proteolytic enzymes, and additional protease inhibitors may desirably be incorporated in the cell culture.

Production of Zymogen Activating Molecules

Host cells are transformed or transfected with the above-described expression vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In preferred embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector, protein expression is induced under conditions suitable for the activation of the promoter. For example, if a PhoA promoter is used for controlling transcription, the transformed host cells may be cultured in a phosphate-limiting medium for induction. A variety of other inducers may be used, according to the vector construct employed, as is known in the art.

Polypeptides described herein expressed in a microorganism may be secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therefrom. Cells may be removed from the culture and the culture supernatant being filtered and concentrated for further purification of the proteins produced. The expressed polypeptides can be further isolated and identified using commonly known methods such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins, ligand affinity using a suitable antigen immobilized on a matrix and Western blot assay.

Besides prokaryotic host cells, eukaryotic host cell systems are also well established in the art. Suitable hosts include mammalian cell lines such as CHO, and insect cells such as those described below.

Polypeptide/Peptide Purification

Polypeptides/peptides that are produced may be purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

Identification and Characterization of Zymogen Activating Molecules (e.g., ZAPs)—General Approach Candidate zymogen activating molecules, e.g. ZAPs, can be identified by any number of methods known in the art. The modulatory characteristics of modulators can be assessed by determining the ability of the modulators to modulate the interaction between the polypeptide comprising the serine protease zymogen domain or serine protease-like zymogen domain (e.g., HGF) and target (e.g., c-Met) (such as the ZAPs described herein). One of the important characteristics is binding affinity. The binding characteristics of candidate modulators (e.g. peptides) of interest can be assessed in any of a number of ways known in the art.

An initial step in the process can include generating one or more candidate zymogen activating molecules (e.g., ZAPs) comprising sequences of interest, which are then displayed under conditions suitable to determine their polypeptide comprising the serine protease zymogen domain or serine protease-like zymogen domain (e.g., HGF in particular the β-chain domain of pro-HGF) binding characteristics. For example, candidate zymogen activating molecules (e.g., ZAPs) can be displayed as carboxyl-terminal (C-terminal) display libraries of peptides on the surface of a phage or phagemid, for example a filamentous phage(mid) using protein fusions with a coat protein such as p3 or p8. C-terminal display is known in the art. See, e.g., Jespers et al., Biotechnology (N Y). 13:378-82 and WO 00/06717. These methods may be used to prepare the fusion genes, fusion proteins, vectors, recombinant phage particles, host cells and libraries thereof described herein. As described herein, in some embodiments, it may be useful to display candidate zymogen activating molecules (e.g., ZAPs) as amino-terminal (N-terminal) display libraries of peptides on the surface of a phage or phagemid. Methods of N-terminal phage(mid) display include those described herein, and those that are well known in the art, e.g., as described in U.S. Pat. No. 5,750,373 (and references cited therein). Methods of characterizing binder molecules obtained by these methods are also known in the art, including those disclosed in the references cited above (Jespers et al., WO 00/06717 & U.S. Pat. No. 5,750,373) and as described herein.

(i) Isolation of Binding Phage

A phage display library with the displayed candidate zymogen activating molecules (e.g., ZAPs) is contacted with polypeptide comprising the serine protease zymogen domain or serine protease-like zymogen domain (e.g., HGF in particular the β-chain of pro-HGF) or fusion proteins in vitro to determine those members of the library that bind to a polypeptide comprising the serine protease zymogen domain or serine protease-like zymogen domain (e.g., HGF in particular the β-chain of pro-HGF). Any method known to the skilled artisan may be used to assay for in vitro protein binding. For example, 1, 2, 3 or 4 rounds or more of binding selection may be performed, after which individual phage are isolated and, optionally, analyzed in a phage ELISA. Binding affinities of peptide-displaying phage particles to immobilized polypeptide comprising the serine protease zymogen domain or serine protease-like zymogen domain (e.g., HGF in particular the β-chain domain of pro-HGF) may be determined using a phage ELISA (Barrett et al., *Anal Biochem.* 204:357-64 (1992)).

In a situation wherein the candidate is being assessed for the ability to compete with a known zymogen activating molecules (e.g., ZAPs) for binding to polypeptide comprising the serine protease zymogen domain or serine protease-like zymogen domain (e.g., HGF in particular the β-chain domain of pro-HGF), the appropriate binding competition conditions are provided. For example, in one embodiment, screening/selection/biopanning can be performed in the presence of one or more concentrations of the known zymogen activating molecules (e.g., ZAPs). In another embodiment, zymogen activating molecules (e.g., ZAPs) isolated from the library can be subsequently assessed in a competitive ELISA assay in the presence of the known zymogen activating molecules (e.g., ZAPs).

(ii) Preparation of Polypeptide Comprising the Serine Protease Zymogen Domain or Serine Protease-Like Zymogen Domain (e.g., HGF in Particular the β-Chain of pro-HGF)

The polypeptide comprising the serine protease zymogen domain or serine protease-like zymogen domain (e.g., HGF in particular the β-chain of pro-HGF) may be produced conveniently as protein fragments containing the domain or as fusion polypeptides using conventional synthetic or recombinant techniques. Fusion polypeptides are useful in phage (mid) display wherein the polypeptide comprising the serine protease zymogen domain or serine protease-like zymogen domain (e.g., HGF in particular the β-chain of pro-HGF) is the target, in expression studies, cell-localization, bioassays, ELISAs (including binding competition assays), etc. A "chimeric protein" or "fusion protein" comprises polypeptide comprising the serine protease zymogen domain or serine protease-like zymogen domain (e.g., HGF in particular the β-chain of pro-HGF) fused to a second polypeptide. The second polypeptide is not substantially homologous to the polypeptide comprising the serine protease zymogen domain or serine protease-like zymogen domain (e.g., HGF in particular the β-chain of pro-HGF). The fusion protein may include any portion to the entire serine protease zymogen domain or serine protease-like zymogen domain (e.g., HGF in particular the β-chain of pro-HGF), including any number of the biologically active portions. The fusion protein can then be purified according to known methods using affinity chromatography and a capture reagent that binds to the second polypeptide. The polypeptide comprising the serine protease zymogen domain or serine protease-like zymogen domain (e.g., HGF in particular the β-chain of pro-HGF) may be fused to an affinity sequence, e.g. the C-terminus of the GST (glutathione S-transferase) sequences. Such fusion proteins facilitate the purification of the recombinant polypeptide comprising the serine protease zymogen domain or serine protease-like zymogen domain (e.g., HGF in particular the β-chain of pro-HGF) using, e.g., glutathione bound to a solid support and/or attachment to solid support (e.g., a matrix for peptide screening/selection/biopanning). Additional exemplary fusions are presented in Table 2, including some common uses for such fusions.

Fusion proteins can be easily created using recombinant methods. A nucleic acid encoding the polypeptide comprising the serine protease zymogen domain or serine protease-like zymogen domain (e.g., HGF in particular the β-chain of pro-HGF) (or portion thereof) can be fused in-frame with a second domain encoding nucleic acid, at the N terminus, C-terminus or internally of the polypeptide comprising the serine protease zymogen domain or serine protease-like zymogen domain (e.g., HGF in particular the β-chain of pro-HGF). In some embodiments, the second domain is fused at the C-terminus of the polypeptide comprising the serine protease zymogen domain or serine protease-like zymogen domain (e.g., HGF in particular the β-chain of pro-HGF). Fusion genes may also be synthesized by conventional techniques, including automated DNA synthesizers. PCR amplification using anchor primers that give rise to complementary overhangs between two consecutive gene fragments that can subsequently be annealed and reamplified to generate a chimeric gene sequence is also useful. Many vectors are commercially available that facilitate sub-cloning the polypeptide comprising the serine protease zymogen domain or serine protease-like zymogen domain (e.g., HGF in particular the β-chain of pro-HGF) in-frame to a fusion protein.

TABLE 2

Useful Second Polypeptides For Fusion Proteins

| Fusion partner | in vitro | in vivo |
|---|---|---|
| Human growth hormone (hGH) | Radioimmuno-assay | none |
| β-glucuronidase (GUS) | Colorimetric, fluorescent, or chemi-luminescent | colorimetric (histo-chemical staining with X-gluc) |
| Green fluorescent protein (GFP) and related molecules (RFP, BFP, YFP domain, etc.) | Fluorescent | fluorescent |
| Luciferase (firefly) Chloramphenicoal acetyltransferase (CAT) | Bioluminsecent Chromatography, differential extraction, fluorescent, or immunoassay | Bioluminescent none |
| β-galactosidase | Colorimetric, fluorescence, chemi-luminscence | colorimetric (histochemical staining with X-gal), bio-luminescent in live cells |

TABLE 2-continued

Useful Second Polypeptides For Fusion Proteins

| Fusion partner | in vitro | in vivo |
|---|---|---|
| Secrete alkaline phosphatase (SEAP) | Colorimetric, bioluminescent, chemi-luminescent | none |
| Tat from HIV | Mediates delivery into cytoplasm and nuclei | Mediates delivery into cytoplasm and nuclei |

As an example of a fusion protein, GST-polypeptide comprising the serine protease zymogen domain or serine protease-like zymogen domain (e.g., HGF in particular the β-chain of pro-HGF) fusion may be prepared from a gene of interest in the following manner. With the full-length gene of interest as the template, the PCR is used to amplify DNA fragments encoding the polypeptide comprising the serine protease zymogen domain or serine protease-like zymogen domain (e.g., HGF in particular the β-chain of pro-HGF) using primers that introduce convenient restriction endonuclease sites to facilitate sub-cloning. Each amplified fragment is digested with the appropriate restriction enzymes and cloned into a similarly digested plasmid, such as pGEX6P-3 or pGEX-4T-3, that contains GST and is designed such that the sub-cloned fragments will be in-frame with the GST and operably linked to a promoter, resulting in plasmids encoding GST-polypeptide comprising the serine protease zymogen domain or serine protease-like zymogen domain (e.g., HGF in particular the β-chain of pro-HGF).

To produce the fusion protein, E. coli cultures harboring the appropriate expression plasmids are generally grown to mid-log phase ($A_{600}$=1.0) in LB broth, e.g. at about 37° C., and may be induced with IPTG. The bacteria are pelleted by centrifugation, resuspended in PBS and lysed by sonication. The suspension is centrifuged, and GST-polypeptide comprising the serine protease zymogen domain or serine protease-like zymogen domain (e.g., HGF in particular the β-chain of pro-HGF) are purified from the supernatant by affinity chromatography on 0.5 ml of glutathione-Sepharose.

It will be apparent to one of skill in the art that many variations will achieve the goal of isolated polypeptide comprising the serine protease zymogen domain or serine protease-like zymogen domain (e.g., HGF in particular the β-chain of pro-HGF) and may be used in this invention. For example, the polypeptide comprising the serine protease zymogen domain or serine protease-like zymogen domain (e.g., HGF in particular the β-chain of pro-HGF) fused to an epitope tag may be constructed as described above and the tags used to affinity purify the polypeptide comprising the serine protease zymogen domain or serine protease-like zymogen domain (e.g., HGF in particular the β-chain of pro-HGF). Polypeptide comprising the serine protease zymogen domain or serine protease-like zymogen domain (e.g., HGF in particular the β-chain of pro-HGF) may also be prepared without any fusions; in addition, instead of using the microbial vectors to produce the protein, in vitro chemical synthesis may instead be used. Other cells may be used to produce polypeptides comprising the serine protease zymogen domain or serine protease-like zymogen domain (e.g., HGF in particular the β-chain of pro-HGF), such as other bacteria, mammalian cells (such as COS), or baculoviral systems. A wide variety of polynucleotide vectors to produce a variety of fusions are also available. The final purification of a polypeptide comprising the serine protease zymogen domain or serine protease-like zymogen domain (e.g., HGF in particular the β-chain of pro-HGF) will generally depend on the fusion partner; for example, a poly-histidine tag fusion can be purified on nickel columns.

(iii) Determining the Sequence of the Displayed Peptide

Phage(mid) that bind to the polypeptide comprising the serine protease zymogen domain or serine protease-like zymogen domain (e.g., HGF in particular the β-chain of pro-HGF) with the desired characteristics (and optionally, does not bind to unrelated sequences), can be subjected to sequence analysis. The phage(mid) particles displaying the candidate zymogen activating molecules (e.g., ZAPs) are amplified in host cells, the DNA isolated, and the appropriate portion of the genome (encoding the candidate peptide) sequenced using any appropriate known sequencing technique.

Other Approaches for Identifying Modulators of the Polypeptide Comprising the Serine Protease Zymogen Domain or Serine Protease-Like Zymogen Domain (e.g., HGF in Particular the β-Chain of pro-HGF)—Ligand Interaction Another approach to identify zymogen activating molecules (e.g., ZAPs) is to incorporate rational drug design; that is, to understand and exploit the biology of the polypeptide comprising the serine protease zymogen domain or serine protease-like zymogen domain (e.g., HGF in particular the β-chain of pro-HGF). In this approach, the critical residues in a zymogen activating molecules (e.g., ZAPs) are determined, as is, optionally, the optimal peptide length. Then, small molecules are designed with this information in hand; for example, if a tyrosine is found to be a critical residue for binding to a serine protease zymogen domain or serine protease-like zymogen domain (e.g., HGF in particular the β-chain of pro-HGF), then small molecules that contain a tyrosine residue will be prepared and tested. Generally 2, 3, 4 or 5 amino acid residues will be determined to be critical for binding and candidate small molecule activators will be prepared containing these residues or the residue side chains. The test compounds are then screened for their ability to bind and/or activate the serine protease zymogen domain or serine protease-like zymogen domain (e.g., HGF in particular the β-chain of pro-HGF) using protocols well-known in the art, for example, as described in Examples 2 and 3.

1. Determining Critical Residues in a Zymogen Activating Molecules (e.g., ZAPs)

(a) Alanine Scanning

Alanine scanning a zymogen activating molecules (e.g., ZAPs) can be used to determine the relative contribution of each residue in the binding and/or activation of the polypeptide comprising the serine protease zymogen domain or serine protease-like zymogen domain (e.g., HGF). To determine the critical residues in a zymogen activating molecules (e.g., ZAPs), residues are substituted with a single amino acid, typically an alanine residue, and the effect on binding and/or activation of the polypeptide comprising the serine protease zymogen domain or serine protease-like zymogen domain (e.g., HGF) is assessed. See U.S. Pat. No. 5,580,723; U.S. Pat. No. 5,834,250; and the Examples.

(b) Truncations (Deletion Series)

Truncation of a zymogen activating molecules (e.g., ZAPs) can elucidate not only binding critical residues, but also determine the minimal length of peptide to achieve binding. In some cases, truncation will reveal a ligand that binds more tightly than the native ligand; such a peptide is useful to modulate the polypeptide comprising the serine protease zymogen domain or serine protease-like zymogen domain (e.g., HGF in particular the β-chain of pro-HGF).

Preferably, a series of zymogen activating molecules (e.g., ZAPs) truncations are prepared. In some embodiments, the truncations will begin at the carboxy terminus. As in the case for alanine scanning, the peptides may be synthesized in vitro or prepared by recombinant methods.

(c) Rational Modulator Design

Based on the information obtained from alanine scanning and truncation analysis, the skilled artisan can design and synthesize small molecules, or select small molecule libraries that are enriched in compounds that are likely to modulate binding. For example, based on the information as described in the Examples, a zymogen activating molecules (e.g., ZAPs) can be designed to include 2 appropriate-spaced hydrophobic moieties.

(d) Binding Assays

Forming a complex of a zymogen activating molecules (e.g., ZAPs) and the polypeptide comprising the serine protease zymogen domain or serine protease-like zymogen domain (e.g., HGF) facilitates separation of the complexed from the uncomplexed forms thereof and from impurities. Polypeptide comprising the serine protease zymogen domain or serine protease-like zymogen domain (e.g., HGF in particular the β-chain of pro-HGF):zymogen activating molecules (e.g., ZAPs) fusions can be formed in solution or where one of the binding partners is bound to an insoluble support. The complex can be separated from a solution, for example using column chromatography, and can be separated while bound to a solid support by filtration, centrifugation, etc. using well-known techniques. Binding the polypeptide comprising the serine protease zymogen domain or serine protease-like zymogen domain (e.g., HGF in particular the β-chain of pro-HGF) or the zymogen activating molecules (e.g., ZAPs) therefor to a solid support facilitates high throughput assays.

Test compounds can be screened for the ability to modulate (e.g., increase) the interaction and/or activity of a zymogen activating molecules (e.g., ZAPs) with polypeptide comprising the serine protease zymogen domain or serine protease-like zymogen domain (e.g., HGF in particular the β-chain of pro-HGF) in the presence and absence of a candidate binding compound, and screening can be accomplished in any suitable vessel, such as microtiter plates, test tubes, and microcentrifuge tubes. Fusion proteins can also be prepared to facilitate testing or separation, where the fusion protein contains an additional domain that allows one or both of the proteins to be bound to a matrix. For example, GST-zymogen activating molecules (e.g., ZAPs) fusion proteins or GST-polypeptide comprising the serine protease zymogen domain or serine protease-like zymogen domain (e.g., HGF in particular the β-chain of pro-HGF) fusion proteins can be adsorbed onto glutathione sepharose beads (SIGMA Chemical, St. Louis, Mo.) or glutathione derivatized microtiter plates that are then combined with the test compound or the test compound and either the nonadsorbed polypeptide comprising the serine protease zymogen domain or serine protease-like zymogen domain (e.g., HGF in particular the β-chain of pro-HGF) protein or zymogen activating molecules (e.g., ZAPs), and the mixture is incubated under conditions allowing complex formation (e.g., at physiological conditions of salt and pH). Following incubation, the beads or microtiter plate wells are washed to remove any unbound components, the matrix immobilized in the case of beads, and the complex determined either directly or indirectly. Alternatively, the fusions can be dissociated from the matrix, and the level of binding or activity determined using standard techniques.

Other fusion polypeptide techniques for immobilizing proteins on matrices can also be used in screening assays. Either a zymogen activating molecules (e.g., ZAPs) or polypeptide comprising the serine protease zymogen domain or serine protease-like zymogen domain (e.g., HGF in particular the β-chain of pro-HGF) can be immobilized using biotin-avidin or biotin-streptavidin systems. Biotinylation can be accomplished using many reagents, such as biotin-N-hydroxy-succinimide (NHS; PIERCE Chemicals, Rockford, Ill.), and immobilized in wells of streptavidin coated 96 well plates (PIERCE Chemical). Alternatively, antibodies reactive with the zymogen activating molecules (e.g., ZAPs) or the polypeptide comprising the serine protease zymogen domain or serine protease-like zymogen domain (e.g., HGF in particular the β-chain of pro-HGF) but do not interfere with binding of a binding peptide to its target molecule can be derivatized to the wells of the plate, and unbound polypeptide comprising the serine protease zymogen domain or serine protease-like zymogen domain (e.g., HGF in particular the β-chain of pro-HGF) or binder peptide trapped in the wells by antibody conjugation. Methods for detecting such fusions, in addition to those described for the GST-immobilized fusions, include immunodetection of fusions using antibodies reactive with the binder peptides or the polypeptide comprising the serine protease zymogen domain or serine protease-like zymogen domain (e.g., HGF in particular the β-chain of pro-HGF).

(e) Assay for Binding: ELISA

To assess the binding affinities of a zymogen activating molecules (e.g., ZAPs), competition binding assays may be used, where the ability of the zymogen activating molecules (e.g., ZAPs) to bind the polypeptide comprising the serine protease zymogen domain or serine protease-like zymogen domain (e.g., HGF in particular the β-chain of pro-HGF) (and the binding affinity, if desired) is assessed and compared to that of a compound known to bind the polypeptide comprising the serine protease zymogen domain or serine protease-like zymogen domain (e.g., HGF in particular the β-chain of pro-HGF), for example, a high-affinity binder peptide determined by phage display as described herein.

Many methods are known and can be used to identify the binding affinities of zymogen activating molecules (e.g., ZAPs) (e.g. peptides, proteins, small molecules, etc.); for example, binding affinities can be determined as a Kd values using ELISAs, for example as defined in Example 2. For example, in solid phase assays, assay plates may be prepared by coating microwell plates (preferably treated to efficiently adsorb protein) with neutravidin, avidin or streptavidin. Non-specific binding sites are then blocked through addition of a solution of bovine serum albumin (BSA) or other proteins (for example, nonfat milk) and then washed, preferably with a buffer containing a detergent, such as Tween-20. A biotinylated known zymogen activating molecules (e.g., ZAPs) (for example, the phage peptides as fusions with GST or other such molecule to facilitate purification and detection) is prepared and bound to the plate. Serial dilutions of the molecule to be tested with the polypeptide comprising the serine protease zymogen domain or serine protease-like zymogen domain (e.g., HGF in particular the β-chain of pro-HGF) are prepared and contacted with the bound zymogen activating molecules (e.g., ZAPs). The plate coated with the immobilized binder is washed before adding each binding reaction to the wells and briefly incubated. After further washing, the binding reactions are detected, often with an antibody recognizing the fusion partner and a labeled (such as horseradish peroxidase (HRP), alkaline phosphatase (AP), or a fluorescent tag such as fluorescein) secondary antibody recognizing the primary antibody. The plates are then developed with the appropriate substrate (depending on the label) and the signal quantified, such as using a spectrophotometric plate reader.

The absorption signal may be fit to a binding curve using a least squares fit. Thus the ability of the various molecules to bind the polypeptide comprising the serine protease zymogen domain or serine protease-like zymogen domain (e.g., HGF in particular the β-chain of pro-HGF) from binding a known zymogen activating molecules (e.g., ZAPs) can be measured.

Apparent to one of skill are the many variations of the above assay. For example, instead of avidin-biotin based systems, zymogen activating molecules (e.g., ZAPs) may be chemically-linked to a substrate, or simply adsorbed.

2. Zymogen Activating Molecules (e.g., ZAPs) Found During Phage Display

Zymogen activating molecules (e.g., ZAPs) are potential useful activators of the polypeptide comprising the serine protease zymogen domain or serine protease-like zymogen domain (e.g., HGF in particular the β-chain of pro-HGF), including those described in the Examples.

The ELISA is a useful means to determine the efficacy of each phage-displayed zymogen activating molecules (e.g., ZAPs) binding the polypeptide comprising the serine protease zymogen domain or serine protease-like zymogen domain (e.g., HGF in particular the β-chain of pro-HGF).

3. Aptamers

Aptamers include short oligonucleotide sequences and peptide sequence that can be used to recognize and specifically bind almost any molecule. The systematic evolution of ligands by exponential enrichment (SELEX) process (See, e.g., Ellington and Szostak, *Nature*. 346:818-22 (1990); Tuerk and Gold, *Science*. 249:505-10 (1990)) can be used to find such aptamers. Aptamers have many diagnostic and clinical uses; for almost any use in which an antibody has been used clinically or diagnostically, aptamers too may be used. In addition, aptamers are less expensive to manufacture once they have been identified and can be easily applied in a variety of formats, including administration in pharmaceutical compositions, bioassays and diagnostic tests (Jayasena, *Clin Chem*. 45:1628-50 (1999)).

In the competitive ELISA binding assay described above, the screen for candidate aptamers includes incorporating the aptamers into the assay and determining their ability to activate the polypeptide comprising the serine protease domain or serine protease-like domain (e.g., HGF in particular the β-chain of pro-HGF).

4. Antibodies (Abs)

Any antibody that modulates (e.g., activate) the polypeptide comprising the serine protease domain or serine protease-like domain (e.g., HGF in particular the β-chain of pro-HGF) can be a modulator (e.g., activator) of the polypeptide comprising the serine protease domain or serine protease-like domain (e.g., HGF) and target interaction (e.g., c-Met). Examples of suitable antibodies include polyclonal, monoclonal, single-chain, anti-idiotypic, chimeric Abs, or humanized versions of such antibodies or fragments thereof. Antibodies may be from any suitable source, including of synthetic origin and any species in which an immune response can be raised.

Screening Methods

This invention encompasses methods of screening compounds to identify those that modulate the polypeptide comprising the serine protease domain or serine protease-like domain (e.g., HGF). In one aspect, provided herein are methods of identifying a zymogen activating molecule (e.g., ZAP) capable of specifically binding a polypeptide comprising a serine protease domain or serine protease-like domain and activating the polypeptide comprising the serine protease zymogen domain or serine protease-like zymogen domain, said method comprising (a) contacting a first sample comprising a polypeptide or fragment thereof comprising a serine protease zymogen domain or serine protease-like zymogen domain in a pro-form and a candidate zymogen activating molecule (e.g., ZAP), (b) contacting a second sample comprising a polypeptide or fragment thereof comprising a serine protease zymogen domain or serine protease-like zymogen domain in a mature-form and the candidate zymogen activating molecule (e.g., ZAP), (c) determining the amount of binding of the candidate zymogen activating molecule (e.g., ZAP) in (a) and (b), wherein greater binding of the candidate zymogen activating molecule (e.g., ZAP) in (a) compared to (b) indicates that the candidate zymogen activating molecule (e.g., ZAP) is capable of specifically binding the polypeptide comprising the serine protease domain or serine protease-like domain and activating the polypeptide comprising the serine protease zymogen domain or serine protease-like zymogen domain.

In some embodiments, the method further comprises assaying the activity of the polypeptide or fragment thereof comprising the serine protease zymogen domain or serine protease-like zymogen domain in a pro-form in the presence of the candidate zymogen activating molecule (e.g., ZAP) and target, wherein activity indicates that the candidate zymogen activating molecule (e.g., ZAP) is capable of specifically binding the polypeptide comprising the serine protease domain or serine protease-like domain and activating the polypeptide comprising the serine protease zymogen domain or serine protease-like zymogen domain.

In some embodiments of any of the methods of screening, the zymogen activating molecules is a ZAP. In some embodiments of any of the methods of screening, the candidate ZAP is one or more ZAPs or ZAP fusions described herein.

In some embodiments of any of the methods of screening, the polypeptide comprising the serine protease domain or serine protease-like domain is HGF, MSP, FVII, FIX, FX, FXI, FXII, Glu-Plasminogen, Lys-Plasminogen, Protein C, Prothrombin, Plasma Kallikrein, Prostasin, Enterokinase, Trypsin 2, Trypsin 1, Chymotrypsin B, Hepsin, HGFA, Matriptase, Testisin, Tryptase alpha 1, Tryptase beta 1, Tryptase beta 2, Tryptase gamma, Neurotrypsin, Apolipoprotein A, MASP 1, MASP 2, PSA KLK3, Haptoglobin, Complement C1r, Complement C1s, Urokinase uPA, tPA, or Complement Factor D. In some embodiments, the polypeptide comprising the serine protease domain or serine protease-like domain is HGF, MSP, Hepsin, HGFA, or Matriptase. In some embodiments, the polypeptide comprising the serine protease zymogen domain or serine protease-like zymogen domain is prethrombin-2 or prothrombin. In some embodiments, the polypeptide comprising the serine protease zymogen domain or serine protease-like zymogen domain is Protein C.

In some embodiments of any of the methods of screening, the target is c-Met. In some embodiments of any of the methods of screening, the polypeptide comprising the serine protease zymogen domain or serine protease-like zymogen domain is HGF, polypeptide or fragment thereof comprising the serine protease zymogen domain or serine protease-like zymogen domain in the pro-form is pro-HGF, and the polypeptide or fragment thereof comprising the serine protease zymogen domain or serine protease-like zymogen domain in the mature-form is mature HGF.

Screening assays are designed to identify compounds that bind or complex with the polypeptide comprising the serine protease domain or serine protease-like domain (e.g., HGF), or otherwise activate the polypeptide comprising the serine protease domain or serine protease-like domain (e.g., HGF) and cellular factors. One approach to determining the ability of a candidate zymogen activating molecules (e.g., ZAPs) to be a modulator is to assess the activity of the candidate zymogen activating molecules (e.g., ZAPs) in a competitive assay in the presence of a known zymogen activating molecules (e.g., ZAPs), such as any of the zymogen activating molecules (e.g., ZAPs) (e.g., the high affinity binders described in the Examples) disclosed herein. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

In binding assays, the interaction between the zymogen activating molecules (e.g., ZAPs) and the polypeptide comprising the serine protease zymogen domain or serine protease-like zymogen domain (e.g., HGF) is binding and the complex formed can be isolated or detected in the reaction mixture. In a particular embodiment, a candidate substance or molecule is immobilized on a solid phase, e.g., on a microtiter plate, by covalent or non-covalent attachments. Non-covalent attachment generally is accomplished by coating the solid surface with a solution of the substance/molecule and drying. Alternatively, an immobilized affinity molecule, such as an antibody, e.g., a monoclonal antibody, specific for the substance/molecule to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with the polypeptide comprising the serine protease domain or serine protease-like domain (e.g., HGF), its interaction with the polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described. See, e.g., Chien et al., *Proc. Natl. Acad. Sci. USA*, 88:9578-9582 (1991)) as disclosed by Chevray and Nathans, *Proc. Natl. Acad. Sci. USA*, 89: 5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

In any of the screening processes above, it is often desirable to assess the modulatory capability of a candidate compound by determining its binding ability to the polypeptide comprising the serine protease domain or serine protease-like domain (e.g., HGF) and a known high affinity zymogen activating molecules (e.g., ZAPs) (such as one of those described herein).

Candidate compounds can be generated by combinatorial libraries and/or mutations of known zymogen activating molecules (e.g., ZAPs) based on information described herein, in particular information relating to contributions and importance to the polypeptide comprising the serine protease domain or serine protease-like domain (e.g., HGF) binding and activation interactions of individual residues and moieties within a ligand or the polypeptide comprising the serine protease domain or serine protease-like domain (e.g., HGF) sequence itself.

As described herein, a zymogen activating molecule can be a ZAP. Methods of obtaining such peptides are well known in the art, and include screening peptide libraries. Libraries of peptides are well known in the art, and can also be prepared according to art methods. See, e.g., Clark et al., U.S. Pat. No. 6,121,416. Libraries of peptides fused to a heterologous protein component, such as a phage coat protein, are well known in the art, e.g., as described in Clark et al., supra. In one embodiment, a ZAP having ability to bind and activate the polypeptide comprising the serine protease domain or serine protease-like domain (e.g., HGF) comprises the amino acid sequence of any of the ZAPs disclosed herein. In another embodiment, a ZAP having ability to bind and activate the polypeptide comprising the serine protease domain or serine protease-like domain (e.g., HGF) comprises the amino acid sequence of a ZAP obtained from a modulator screening assay as described above. In one embodiment, the ZAP has the ability to compete with one or more of the ZAPs disclosed herein for binding to the polypeptide comprising the serine protease domain or serine protease-like domain (e.g., HGF). Variants of a first ZAP can be generated by screening mutants of the peptide to obtain the characteristics of interest (e.g., enhancing target binding affinity, enhanced pharmacokinetics, reduced toxicity, improved therapeutic index, etc.). Mutagenesis techniques are well known in the art. Furthermore, scanning mutagenesis techniques (such as those based on alanine scanning) can be especially helpful to assess structural and/or functional importance of individual amino acid residues within a peptide.

Determination of the ability of a zymogen activating molecule, such as a ZAP disclosed herein, to modulate the polypeptide comprising the serine protease domain or serine protease-like domain (e.g., HGF) activity, can be performed by testing the modulatory capability of the substance/molecule in in vitro or in vivo assays, which are well established in the art, e.g., as described in Martins et al. (*J. Biol. Chem.* 278(49):49417-49427 (2003)) and Faccio et al. (*J. Biol. Chem.* 275(4):2581-2588 (2000)).

Examples of Uses

The identification and characterization of the zymogen activating molecules (e.g., ZAPs) as described herein provide valuable insights into the cellular functions of the polypeptide comprising the serine protease domain or serine protease-like domain (e.g., HGF), and provides compositions and methods for modulating the in vivo interactions between this important cellular protein and its binding partner(s). For example, these zymogen activating molecules (e.g., ZAPs) and their homologs can be utilized to enhance in vivo binding interactions and activation of the polypeptide comprising the serine protease domain or serine protease-like domain (e.g., HGF). Homologs can be generated conveniently based on their binding and/or functional characteristics relative to the well-characterized zymogen activating molecules (e.g., ZAPs) provided herein. These zymogen activating molecules (e.g., ZAPs) can further be utilized to elucidate cellular and physiological polypeptides that constitute the polypeptide comprising the serine protease domain or serine protease-like domain (e.g., HGF) in vivo complexes.

Well-characterized moderate to high affinity zymogen activating molecules (e.g., ZAPs) as described herein can be further used to elucidate important structural characteristics of the polypeptide comprising the serine protease domain or serine protease-like domain (e.g., HGF) itself. Knowledge of such provides for development of zymogen activating molecules (e.g., ZAPs) based on modification of the polypeptide comprising the serine protease domain or serine protease-like domain (e.g., HGF) itself. The invention provides the polypeptide comprising the serine protease domain or serine protease-like domain (e.g., HGF) variants as disclosed herein that have enhanced ability to bind and/or activate the polypeptide comprising the serine protease domain or serine protease-like domain (e.g., HGF) targets. Other variants can be similarly identified.

Zymogen activating molecules (e.g., ZAPs) developed based on the zymogen activating molecules (e.g., ZAPs) described herein can be used to achieve the modulatory effect of interest. For example, such manipulation may include activation of the association between the polypeptide comprising the serine protease domain or serine protease-like domain (e.g., HGF) and its cognate binding protein (e.g., c-Met). In another example, such manipulation may include agonistic effects through, for example, induction of cellular functions as a result of binding of the zymogen activating molecules (e.g., ZAPs) or through enhancement of association between the polypeptide comprising the serine protease domain or serine protease-like domain (e.g., HGF) and its cognate binding protein (e.g., c-Met) by the modulators.

Other uses of zymogen activating molecules (e.g., ZAPs) include diagnostic assays for diseases related to the polypeptide comprising the serine protease domain or serine protease-like domain (e.g., HGF) and its associating partners, the use of the polypeptide comprising the serine protease domain or serine protease-like domain (e.g., HGF) and partners in fusion proteins as purification handles and anchors to substrates.

Identification of zymogen activating molecules (e.g., ZAPs) capable of binding to the polypeptide comprising the serine protease domain or serine protease-like domain (e.g., HGF) at varying affinities, as described herein, provide useful avenues for modulating biologically important interactions in vivo. As is well-established in the art, the serine protease domain or serine protease-like domain (e.g., HGF) is implicated in important biological processes, including regulation of cell proliferation and cell migration. The polypeptide comprising the serine protease domain or serine protease-like domain (e.g., HGF), which is a domain reported to be essential in protein functions. Thus, identification of zymogen activating molecules (e.g., ZAPs) which are capable of modulating these interactions points to avenues of therapeutic and/or diagnostic applications and strategies that would not be possible in the absence of knowledge of such molecules and interactions. Zymogen activating molecules (e.g., ZAPs) can be delivered into live cells using appropriate routes of administration known in the art, e.g., via microinjection, antenapedia peptide or lipid transfection reagents, to serve as the polypeptide comprising the serine protease domain or serine protease-like domain (e.g., HGF)-specific zymogen activating molecules (e.g., ZAPs) in order to modulate, and in some instances validate the physiological importance of the polypeptide comprising the serine protease domain or serine protease-like domain (e.g., HGF) interaction in a particular tissue, cell, organ or pathological condition. Suitable assays exist to monitor the polypeptide comprising the serine protease domain or serine protease-like domain (e.g., HGF) interaction and the physiological effect of modulation of said interaction. This does not require that the physiological ligand for the polypeptide comprising the serine protease domain or serine protease-like domain (e.g., HGF) is discovered by phage display, only that the zymogen activating molecules (e.g., ZAPs) binds to the polypeptide comprising the serine protease domain or serine protease-like domain (e.g., HGF) and of sufficient affinity to facilitate the activation of said ligand with the polypeptide comprising the serine protease domain or serine protease-like domain (e.g., HGF). Finally, as with any protein linked with a disease process, one must establish how a drug should affect the protein to achieve therapeutic benefit. Zymogen activating molecules (e.g., ZAPs) may be delivered into live cells or animal models which are models for a disease (i.e. mimic certain properties of a disease) to determine if activation of the polypeptide comprising the serine protease domain or serine protease-like domain (e.g., HGF)-ligand interaction by the zymogen activating molecules (e.g., ZAPs) of interest provides an outcome consistent with expectations for therapeutic benefit.

Methods of detecting protein-protein (or peptide) interactions in vivo are known in the art. For example, the methods described by Michnick et al. in U.S. Pat. Nos. 6,270,964 B1 & 6,294,330 B1 can be used to analyze interactions and/or activity of the polypeptide comprising the serine protease domain or serine protease-like domain (e.g., HGF) (including any described herein) and a cognate ligand or synthetic ZAP (including any described herein). Furthermore, these methods can be used to assess the ability of a molecule, such as a synthetic ZAP, to modulate the binding interaction and/or activity of the polypeptide comprising the serine protease domain or serine protease-like domain (e.g., HGF) protein and its cognate ligand in vivo.

Pharmaceutical Formulations

Pharmaceutical formulations of a zymogen activating molecule (e.g., ZAP) as described herein are prepared by mixing such zymogen activating molecule (e.g., ZAP) having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

In some embodiments of any of the pharmaceutical formulations, the ZAP comprises the amino acid sequence $X_1$-$X_2$-$X_3$-$X_4$-$B_n$ (SEQ ID NO:2), wherein $X_1$ is a large hydrophobic amino acid, $X_2$ is a large hydrophobic amino acid or an aromatic amino acid, $X_3$ is G, D, E, N, Q, D-Gly, D-Asp, D-Glu, D-Asn, or D-Gln, $X_4$ is G or A, B is any amino acid, and n is a number between 0-46. In some embodiments, the ZAP consists of the amino acid sequence $X_1$-$X_2$-$X_3$-$X_4$-$B_n$ (SEQ ID NO:31), wherein $X_1$ is a large hydrophobic amino acid, $X_2$ is a large hydrophobic amino acid or an aromatic amino acid, $X_3$ is G, D, E, N or Q, $X_4$ is G or A, B is any amino acid, and n is a number between 0-46. In some embodiments of any of the ZAPs, wherein $X_1$ is V, $X_3$ is not N (i.e., $X_3$ is G, D, E, or Q) (SEQ ID NO:32). In some embodiments, $X_1$ is M, L, I, V or NorLeucine (SEQ ID NO:4). In some embodiments, $X_1$ is L, I, or V (SEQ ID NO:5). In some embodiments, $X_1$ is I (SEQ ID NO:7). In some embodiments, $X_2$ is M, L, I, V, NorLeucine, F, or Y (SEQ ID NO:8). In some embodiments, $X_2$ is I, V, L or F (SEQ ID NO:9). In some embodiments, $X_2$ is I or V (SEQ ID NO:10). In some embodiments, $X_3$ is G, D, or N (SEQ ID NO:11). In some embodiments, $X_3$ is G (SEQ ID NO:12). In some embodiments, $X_4$ is G (SEQ ID NO:13). In some embodiments, the ZAP binds the β-chain domain of pro-HGF and activates c-Met signaling. In some embodiments, the ZAP has a binding affinity as determined by a Kd of less than about 100 μM (for example less than about 25 μM).

The formulation herein may also contain more than one active ingredients as necessary for the particular indication being treated, preferably those with complementary activities that do not adversely affect each other. Such active ingredients are suitably present in combination in amounts that are effective for the purpose intended.

Zymogen activating molecules (e.g., ZAPs) may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the zymogen activating molecule (e.g., ZAP), which matrices are in the form of shaped articles, e.g. films, or microcapsules.

The formulations to be used for in vivo administration are generally sterile. Sterility may be readily accomplished, e.g., by filtration through sterile filtration membranes.

Therapeutic/Prophylactic Methods and/or Uses

Compounds that have the property of increasing the polypeptide comprising the serine protease domain or serine protease-like domain (e.g., HGF) activity are useful. This increase in activity may come about in a variety of ways, for example by administering to a subject in need thereof an effective amount of one or more of the zymogen activating molecule (e.g., ZAP) described herein.

Any of the zymogen activating molecule (e.g., ZAP) described herein may be used in therapeutic methods.

In one aspect, a zymogen activating molecule (e.g., ZAP) for use as a medicament is provided. In further aspects, a zymogen activating molecule (e.g., ZAP) for use in a method of promoting tissue repair and/or tissue regeneration is provided. In certain embodiments, the invention provides a zymogen activating molecule (e.g., ZAP) for use in a method of promoting tissue repair and/or tissue regeneration in an individual comprising administering to the individual an effective of the zymogen activating molecule (e.g., ZAP) to promote tissue repair and/or tissue regeneration. In certain embodiments, a zymogen activating molecule (e.g., ZAP) for use in a method of treatment is provided. In certain embodiments, provided are zymogen activating molecules (e.g., ZAPs) for use in a method of treating an individual having fibrosis and/or liver cirrhosis comprising administering to the individual an effective amount of the zymogen activating molecule (e.g., ZAP). In one such embodiment, the method further comprises administering to the individual an effective amount of at least one additional therapeutic agent, e.g., as described below. In further embodiments, the invention provides a zymogen activating molecule (e.g., ZAP) for use in promoting wound healing. In certain embodiments, the invention provides a zymogen activating molecule (e.g., ZAP) for use in a method of promoting wound healing in an individual comprising administering to the individual an effective of the zymogen activating molecule (e.g., ZAP) to promote wound healing. In further embodiments, the invention provides a zymogen activating molecule (e.g., ZAP) for use in promoting wound healing. In certain embodiments, the invention provides a zymogen activating molecule (e.g., ZAP) for use in a method of promoting cell proliferation and/or cell migration in an individual comprising administering to the individual an effective of the zymogen activating molecule (e.g., ZAP) to promote cell proliferation and/or cell migration. An "individual" according to any of the above embodiments is preferably a human.

In a further aspect, the invention provides for the use of a zymogen activating molecule (e.g., ZAP) in the manufacture or preparation of a medicament. In one embodiment, the medicament is for treatment of fibrosis and/or liver cirrhosis. In a further embodiment, the medicament is for use in a method of treating fibrosis and/or liver cirrhosis comprising administering to an individual having fibrosis and/or liver cirrhosis an effective amount of the medicament. In one such embodiment, the method further comprises administering to the individual an effective amount of at least one additional therapeutic agent, e.g., as described below. In a further embodiment, the medicament is for promoting tissue regeneration and/or tissue repair. In a further embodiment, the medicament is for use in a method of promoting tissue regeneration and/or tissue repair in an individual comprising administering to the individual an amount effective of the medicament to promote tissue regeneration and/or tissue repair. In a further embodiment, the medicament is for promoting wound healing. In a further embodiment, the medicament is for use in a method of promoting wound healing in an individual comprising administering to the individual an amount effective of the medicament to promote wound healing. In a further embodiment, the medicament is for promoting cell proliferation and/or cell migration. In a further embodiment, the medicament is for use in a method of promoting cell proliferation and/or cell migration in an individual comprising administering to the individual an amount effective of the medicament to promote cell proliferation and/or cell migration. An "individual" according to any of the above embodiments may be a human.

In a further aspect, the invention provides a method for treating a fibrosis and/or liver cirrhosis. In one embodiment, the method comprises administering to an individual having such fibrosis and/or liver cirrhosis an effective amount of a zymogen activating molecule (e.g., ZAP). In one such embodiment, the method further comprises administering to the individual an effective amount of at least one additional therapeutic agent, as described below. An "individual" according to any of the above embodiments may be a human.

In a further aspect, the invention provides a method for promoting tissue regeneration or tissue repair in an individual. In one embodiment, the method comprises administering to the individual an effective amount of a zymogen activating molecule (e.g., ZAP) to promote tissue regeneration or tissue repair. In a further aspect, the invention provides a method for promoting wound healing in an individual. In one embodiment, the method comprises administering to the individual an effective amount of a zymogen activating molecule (e.g., ZAP) to promote wound healing. In a further aspect, the invention provides a method for promoting cell migration and/or cell proliferation in an individual. In one embodiment, the method comprises administering to the individual an effective amount of a zymogen activating molecule (e.g., ZAP) to promote cell migration and/or cell proliferation. In one embodiment, an "individual" is a human.

In some embodiments of any of uses and/or methods herein, the ZAP comprises the amino acid sequence $X_1$-$X_2$-$X_3$-$X_4$-$B_n$ (SEQ ID NO:2), wherein $X_1$ is a large hydrophobic amino acid, $X_2$ is a large hydrophobic amino acid or an aromatic amino acid, $X_3$ is G, D, E, N, Q, D-Gly, D-Asp, D-Glu, D-Asn, or D-Gln, $X_4$ is G or A, B is any amino acid, and n is a number between 0-46. In some embodiments, the ZAP consists of the amino acid sequence $X_1$-$X_2$-$X_3$-$X_4$-$B_n$ (SEQ ID NO:31), wherein $X_1$ is a large hydrophobic amino acid, $X_2$ is a large hydrophobic amino acid or an aromatic amino acid, $X_3$ is G, D, E, N or Q, $X_4$ is G or A, B is any amino acid, and n is a number between 0-46. In some embodiments of any of the ZAPs, wherein $X_1$ is V, $X_3$ is not N (i.e., $X_3$ is G, D, E, or Q) (SEQ ID NO:32). In some embodiments, $X_1$ is M, L, I, V or NorLeucine (SEQ ID NO:4). In some embodiments, $X_1$ is L, I, or V (SEQ ID NO:5). In some embodiments, $X_1$ is I (SEQ ID NO:7). In some embodiments, $X_2$ is M, L, I, V, NorLeucine, F, or Y (SEQ ID NO:8). In some embodiments, $X_2$ is I, V, L or F (SEQ ID NO:9). In some embodiments, $X_2$ is I or V (SEQ ID NO:10). In some embodiments, $X_3$ is G, D, or N (SEQ ID NO:11). In some embodiments, $X_3$ is G (SEQ ID NO:12). In some embodiments, $X_4$ is G (SEQ ID NO:13). In some embodiments, the ZAP binds the β-chain domain of pro-HGF and activates c-Met signaling. In some embodiments, the ZAP has a binding affinity as determined by a Kd of less than about 100 μM (for example less than about 25 μM).

In a further aspect, provided herein are pharmaceutical formulations comprising any of the zymogen activating molecule (e.g., ZAP) described herein, e.g., for use in any of the above therapeutic methods. In one embodiment, a pharmaceutical formulation comprises any of the zymogen activating molecule (e.g., ZAP) provided herein and a pharmaceutically acceptable carrier. In another embodiment, a pharmaceutical formulation comprises any of the zymogen activating molecule (e.g., ZAP) provided herein and at least one additional therapeutic agent, e.g., as described below.

The zymogen activating molecule (e.g., ZAP) described herein can be used either alone or in combination with other agents in a therapy. For instance, a zymogen activating molecule (e.g., ZAP) of the invention may be co-administered with at least one additional therapeutic agent.

Such combination therapies noted above encompass combined administration (where two or more therapeutic agents are included in the same or separate formulations), and separate administration, in which case, administration of the zymogen activating molecule (e.g., ZAP) described herein can occur prior to, simultaneously, and/or following, administration of the additional therapeutic agent.

A zymogen activating molecule (e.g., ZAP) described herein (and any additional therapeutic agent) can be administered by any suitable means, including parenteral, intrapulmonary, and intranasal, and, if desired for local treatment, intralesional administration, topical administration, or intraocular administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Zymogen activating molecules (e.g., ZAPs) should be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The zymogen activating molecule (e.g., ZAP) need not be, but is optionally formulated with one or more agents currently used to prevent or treat the disorder in question. The effective amount of such other agents depends on the amount of the zymogen activating molecule (e.g., ZAP) present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of a zymogen activating molecule (e.g., ZAP) described herein (when used alone or in combination with one or more other additional therapeutic agents) will depend on the type of disease to be treated, the type of zymogen activating molecule (e.g., ZAP), the severity and course of the disease, whether the zymogen activating molecule (e.g., ZAP) is administered for preventive or therapeutic purposes, previous therapy, the patient's clinical history and response to the zymogen activating molecule (e.g., ZAP), and the discretion of the attending physician. The zymogen activating molecule (e.g., ZAP) is suitably administered to the patient at one time or over a series of treatments. Depending on the type and severity of the disease, about 10 ng/kg to up to about 100 mg/kg (e.g., 0.01 to about 500 mg/kg) of zymogen activating molecule (e.g., ZAP) can be an initial candidate dosage for administration to the patient, whether, for example, by one or more separate administrations, or by continuous infusion. Preferably, the dosage level will be about 0.1 to about 250 mg/kg per day; more preferably about 0.5 to about 100 mg/kg per day. A suitable dosage level may be about 0.01 to about 250 mg/kg per day, about 0.05 to about 100 mg/kg per day, or about 0.1 to about 50 mg/kg per day. Within this range the dosage may be about any of 0.05 to 0.5, 0.5 to 5 or 5 to 50 mg/kg per day. For oral administration, the compositions are preferably provided in the form of tablets containing about 1.0 to about 1000 milligrams of the active ingredient, particularly about any of 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day. Such doses may be administered intermittently, e.g. every week or every three weeks (e.g. such that the patient receives from about two to about twenty, or e.g. about six doses of the zymogen activating molecule (e.g., ZAP)). An initial higher loading dose, followed by one or more lower doses may be administered. However, other dosage regimens may be useful. The progress of this therapy is easily monitored by conventional techniques and assays.

Articles of Manufacture

In another, an article of manufacture containing materials useful for the treatment, prevention and/or diagnosis of the disease and/or disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disease and/or disorder and may have a sterile access port (for example the container may be an intravenous solution bag or a vial having a stopper pierceable by a hypodermic injection needle). At least one active agent in the composition is a zymogen activating molecule (e.g., ZAP) described herein. The label or package insert indicates that the composition is used for treating the disease and/or disorder of choice. Moreover, the article of manufacture may comprise (a) a first container with a composition contained therein, wherein the composition comprises a zymogen activating molecule (e.g., ZAP) described herein; and (b) a second container with a composition contained therein, wherein the composition comprises an additional therapeutic agent. The article of manufacture in this embodiment of the invention may further comprise a package insert indicating that the compositions can be used to treat a particular disease and/or disorder. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In some embodiments of any of the articles of manufacture, the ZAP comprises the amino acid sequence $X_1$-$X_2$-$X_3$-$X_4$-$B_n$ (SEQ ID NO:2), wherein $X_1$ is a large hydrophobic amino acid, $X_2$ is a large hydrophobic amino acid or an aromatic amino acid, $X_3$ is G, D, E, N, Q, D-Gly, D-Asp, D-Glu, D-Asn, or D-Gln, $X_4$ is G or A, B is any amino acid, and n is a number between 0-46. In some embodiments, the ZAP consists of the amino acid sequence $X_1$-$X_2$-$X_3$-$X_4$-$B_n$ (SEQ ID NO:3), wherein $X_1$ is a large hydrophobic amino acid, $X_2$ is a large hydrophobic amino acid or an aromatic amino acid, $X_3$ is G, D, E, N, Q, or D-amino acid, $X_4$ is G or A, B is any amino acid, and n is a number between 0-46. In some embodiments of any of the ZAPs, wherein $X_1$ is V, $X_3$ is not N (i.e., $X_3$ is G, D, E, or Q) (SEQ ID NO:32). In some embodiments, $X_1$ is M, L, I, V or NorLeucine (SEQ ID NO:4). In some embodiments, $X_1$ is L, I, or V (SEQ ID NO:5). In some embodiments, $X_1$ is I (SEQ ID NO:7). In some embodiments, $X_2$ is M, L, I, V, NorLeucine, F, or Y (SEQ ID NO:8). In some embodiments, $X_2$ is I, V, L or F (SEQ ID NO:9). In some embodiments, $X_2$ is I or V (SEQ ID NO:10). In some embodiments, $X_3$ is G, D, or N (SEQ ID NO:11). In some embodiments, $X_3$ is G (SEQ ID NO:12). In some embodiments, $X_4$ is G (SEQ ID NO:13). In some embodiments, the ZAP binds the β-chain domain of pro-HGF and activates c-Met signaling. In some embodiments, the ZAP has a binding affinity as determined by a Kd of less than about 100 μM (for example less than about 25 μM).

The following examples are included to demonstrate preferred embodiments of the present invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing form the spirit and scope of the invention.

EXAMPLES

Material and Methods for the Examples

Recombinant Protein Production and Peptide Synthesis

Full-length recombinant HGF proteins were expressed in 1-liter fermentation cultures of Chinese hamster ovary (CHO) cells and purified as described previously (Peek, M. et al. (2002) *J Biol Chem* 277: 47804-9). All mutations were introduced using QuikChange™ sited-directed mutagenesis (Stratagene) and verified by DNA sequencing. Proteins were purified using HiTrap-Sepharose SP cation exchange chromatography as described (Peek, M. et al. (2002) *J Biol Chem* 277: 47804-9). SDS-PAGE (4-20% gradient gel) analysis under reducing conditions revealed the proteins were >95% pure.

The HGF β-chain construct used (residues $Val^{495}$ to $Ser^{728}$) contains the C604S mutation and the scHGF β-chain (residues $Asn^{479}$ to $Ser^{728}$) contains the R494E mutation; both previously described (Stamos, J. et al. (2004) *EMBO J* 23: 2325-35). Proteins were expressed as C-terminal His-tag fusions from the pAcGP67 vector (BD Biosciences) in insect cells and purified as previously described (Stamos, J. et al. (2004) *EMBO J* 23: 2325-35). Peptides were synthesized as C-terminal amides and purified as previously described (Lowman, H. B. et al. (1998) *Biochemistry* 37: 8870-8).

Cloning, expression and purification of the AviTag Sema/PSI domain of Met from insect cells has been described (Stamos, J. et al. (2004) *EMBO J* 23: 2325-35; Landgraf, K. E. et al. (2010) *J Biol Chem* 285: 40362-72). The purified Sema/PSI fragment was biotinylated using the AviTag in vitro biotinylation kit (GeneCopoeia) according to the manufacturer's protocol.

Phage Library Construction and Panning

The pfam database (Finn, R. D. et al. (2010) *Nucleic Acids Res* 38: D211-22) was used to derive a consensus sequence for trypsin/chymotrypsin-like serine proteases and identify the N-terminal IVGG motif. Peptide libraries were synthesized as fusions to the gene VIII coat protein of M13 phage and panned against scHGF β as previously described (Tonikian, R. et al. (2007) *Nat Protoc* 2: 1368-86; Sidhu, S. S. et al. (2000) *Methods Enzymol.* 328:333-63). After 4 rounds of solution sorting, 5-fold enrichment of the phage titer was observed for scHGF β over background. Single phage clones were picked, grown overnight and a standard phage ELISA was used to verify target specific binding. Once the IVGG.14 sequence was identified, soft randomization on gene VIII was performed on positions $X_2$-$X_{11}$. After 4 rounds of panning a 340-fold enrichment was observed and the final motif was generated by alignment of 36 unique sequences (Table 3).

TABLE 3

Alignment of 36 unique sequences derived from soft randomization.

| | | | | | | | | | | |
|---|---|---|---|---|---|---|---|---|---|---|
| SEQ ID NO: 78 | I | V | D | D | Y | P | W | W | I | E | V |
| SEQ ID NO: 79 | I | V | D | G | Y | P | W | W | I | D | V |
| SEQ ID NO: 80 | I | V | G | D | Y | P | W | W | I | E | V |
| SEQ ID NO: 81 | I | V | D | G | Y | P | W | W | V | D | V |
| SEQ ID NO: 82 | I | V | Y | D | V | P | W | W | M | D | V |
| SEQ ID NO: 83 | I | V | E | D | Y | P | W | W | V | E | V |
| SEQ ID NO: 84 | I | V | D | G | Y | P | W | W | M | E | V |
| SEQ ID NO: 85 | I | V | D | D | Y | P | W | W | I | D | V |
| SEQ ID NO: 86 | I | V | G | D | Y | P | W | W | M | D | V |
| SEQ ID NO: 87 | I | V | G | E | Y | P | W | W | M | D | A |
| SEQ ID NO: 88 | I | V | D | G | Y | P | W | W | M | D | V |
| SEQ ID NO: 89 | I | V | A | D | Y | P | W | W | V | D | V |
| SEQ ID NO: 90 | I | V | G | D | Y | P | W | W | V | D | V |
| SEQ ID NO: 91 | I | V | E | D | F | P | W | W | M | E | A |
| SEQ ID NO: 92 | I | V | G | G | F | P | W | W | I | E | A |
| SEQ ID NO: 93 | I | V | E | D | Y | P | W | W | L | D | V |
| SEQ ID NO: 94 | I | V | D | D | Y | P | W | W | M | H | A |
| SEQ ID NO: 95 | I | V | D | D | Y | P | W | W | V | D | V |
| SEQ ID NO: 96 | I | P | G | D | Y | P | W | W | I | D | V |
| SEQ ID NO: 97 | I | V | G | E | Y | P | W | W | V | D | V |
| SEQ ID NO: 98 | I | S | D | G | Y | P | W | W | I | D | A |
| SEQ ID NO: 99 | I | V | D | D | Y | P | W | W | I | E | V |
| SEQ ID NO: 100 | I | V | D | G | Y | P | W | W | M | D | V |
| SEQ ID NO: 101 | I | I | G | G | E | P | W | W | M | D | V |
| SEQ ID NO: 102 | I | V | E | D | Y | P | W | W | M | Y | V |
| SEQ ID NO: 103 | I | V | D | G | Y | P | W | W | M | D | V |
| SEQ ID NO: 104 | I | V | D | E | Y | P | W | W | I | G | V |
| SEQ ID NO: 105 | I | V | D | D | W | P | W | W | M | E | V |
| SEQ ID NO: 106 | I | V | D | D | Y | P | W | W | M | D | V |
| SEQ ID NO: 107 | I | V | D | G | Y | P | W | W | L | E | V |
| SEQ ID NO: 108 | I | V | G | G | Y | P | W | W | M | E | V |
| SEQ ID NO: 109 | I | V | G | G | Y | P | W | W | M | E | A |
| SEQ ID NO: 110 | I | V | D | G | Y | P | W | W | I | D | V |
| SEQ ID NO: 111 | I | I | D | D | Y | P | W | W | M | E | V |
| SEQ ID NO: 112 | I | V | D | D | Y | P | W | W | M | N | V |
| SEQ ID NO: 113 | I | V | G | G | Y | P | W | W | M | D | V |

Where activity-based sorting was conducted, the phage library was incubated in solution with 0.5 μM scHGF β at 4° C. then the mixture was applied to a Maxi-Sorp plate coated with 5 μg/ml Met Sema-PSI ECD protein for capture of activated complex. To analyze phage clones from the activity-based sorting two ELISAs were carried out separately to analyze binding and activity. The first ELISA measured direct phage binding to wells coated with 5 μg/ml scHGF β relative to a BSA control. The second activity ELISA measured phage binding to wells coated with 5 μg/ml Met in the presence or absence (negative control) of 0.5 μM scHGF β in solution. The data from these two ELISAs were plotted with direct binding on the y-axis and Met capture (activity) on the x-axis.

scHGF β Activation/Met Binding Assay

Met binding assays were carried out utilizing the OctetRed™ biolayer interferometry instrument (ForteBio, Inc.) as reported previously (Landgraf, K. E. et al. (2010) *J Biol Chem* 285: 40362-72). Biotinylated Met ECD (Sema/PSI-AviTag) was captured on the surface of streptavidin optical sensor tips (SA biosensors, ForteBio, Inc.), and transferred into buffer containing 0.5 µM scHGF β-chain variants in the presence of increasing concentration of indicated peptides. Association and dissociation reactions were monitored to ensure reversible binding between scHGF β and Met. Binding was quantified using the steady-state levels of surface response from the association reaction. Equilibrium constants were derived by least squares fitting of the titration data to a single-site binding equation. Errors reported are ±stdev of n=3 independent experiments.

Cell Survival Assay

BxPC-3 cells were obtained from ATCC and maintained in cell culture medium (RPMI, 10% FBS (Sigma), 50 U/ml penicillin/50 µg/ml streptomycin, 2 mM glutamine). For the survival assay, cells were plated at 10,000 cells/well in 96 well tissue culture plates (Falcon 353072) in 50 µl assay diluent (RPMI, 0.1% BSA (Sigma) 50 U/ml penicillin/50 µg/ml streptomycin, 2 mM glutamine). Cells were allowed to attach for 1-2 h in a 37° C. $CO_2$ incubator. Human HGF proteins (HGF, scHGF or scHGF plus peptide titrations) were pre-incubated at room temperature in assay diluent. HGF/peptide mixtures were added to cells in microtiter plates in triplicate at 50 µl per well and plates were incubated at 37° C. in a $CO_2$ incubator. Final concentrations of HGF variants were 400 ng/ml and peptide concentrations were titrated accordingly. After 72 h, 25 µl alamar Blue (Serotec, BUF012B) was added to each well and incubate an additional 2 h at 37° C. in a $CO_2$ incubator. Plates were agitated vigorously for 10 min at room temperature, and fluorescence was read at 530-590 nm in a fluorescent plate reader.

Structure Determination

The HGF β V495G and Met Sema-PSI ECD proteins were purified as described previously (Stamos, J. et al. (2004) *EMBO J* 23: 2325-35). Pure IVGG.14 peptide at 100 mM in 100% DMSO was added to a 1:1 stoichiometric mixture of HGF β V495G and Met Sema-PSI ECD pre-concentrated to 10 mg/ml total protein in 10 mM Hepes, 150 mM NaCl, pH 7.2. Final peptide and DMSO concentration was 1 mM and 1%, respectively. Diffraction quality crystals grew in 3 days in 2 µL drops containing the above complex mixed with an equal volume of seed stock diluted in reservoir (0.1 M Tris pH 8.5, 10% P6000, 0.8 M NaCl, 0.4 M Trimethylammonium oxide). Crystals were dehydrated by sequentially transferring the crystals through an increasing concentration of PEG 400 added to the reservoir solution. The final concentration of the dehydration solution was 35% P400, this same solution was used as a cryoprotectant and the crystals were preserved by immersion in liquid nitrogen.

Diffraction data extending to 3 Å were collected by Shamrock Biostructures LLC in a primitive orthorhombic lattice at 110 K at beamline 21-IDF of the Advanced Photon Source (APS) (Table 6). The structure was solved by molecular replacement using PHASER (McCoy et al., 2007) in space group $P2_12_12_1$ using the β/Met complex in pdb entry 1SHY. The initial electron density maps indicated a large rigid-body shift of the Met PSI domain (residues 517-564) and significant changes in the N-terminal region of HGF β. After manual adjustment of the PSI domain and deletion of HGF β residues Val495-Trp507 and simulated-annealing refinement using phenix.refine (Adams et al., 2010), the difference electron density for the HGF β N-terminal region was unambiguously assigned as that of the peptide rather than of the mutant HGF β N-terminal segment. The Trp-Trp-Met tripeptide motif was especially clear. Additional changes using Coot (Emsley et al., 2010) and refinement using REFMAC5 (Murshudov et al., 1997) led to the final model characterized with statistics appearing in Table 6.

Zymogen Serine Protease Activity Assay

Zymogen serine proteases prethrombin-2 and Protein C were purchased from Haematologic Technologies, Inc. (Essex Junction, Vt.). Kinetic assays were carried out in 20 mM Hepes, 150 mM NaCl, 5 mM $CaCl_2$, 0.01% Triton X-100, pH 7.2. All reactions contained 100 nM of enzyme plus 2 mM Ile-Pro-Arg-pNA substrate. IVGG.147A was titrated and the initial rates of substrate hydrolysis were measured in clear bottom 96-well plates using 405 nm absorbance on a SpectraMax Plus (Molecular Devices, Inc.).

Example 1

Phaging Zymogen-Like scHGF β with an Activation Pocket-Specific Peptide Library Yields a Highly Conserved Sequence Motif In order to identify peptides that can specifically bind with high affinity to the activation pocket of the zymogen-like form of HGF β (scHGF β), phage peptide libraries were engineered based on structural and sequence homology found within the N-terminal residues of trypsin/chymotrypsin-like serine protease domains. Interestingly, there is high structural homology between the activation pockets of trypsin/chymotrypsin-like serine protease domains and that of HGF β (Kirchhofer, D. et al. (2004) *J Biol Chem* 279: 39915-24; Kirchhofer, D. et al. (2007) *Proc Natl Acad Sci USA* 104: 5306-11), clearly highlighting the functional conservation of the N-terminal insertion mechanism. In addition to the structural homology, a pfam (Finn, R. D. et al. (2010) *Nucleic Acids Res* 38: D211-22) consensus sequence profile of the N-terminal residues frequently found in trypsin/chymotrypsin-like serine protease domains revealed a conserved motif within the first 4 amino acids of the inserted N-terminus, I-V-G-G (SEQ ID NO:15), indicating these residues are likely critical for the function of a peptide that specifically targets the activation pocket and mediates a zymogen state-to-active state transition. Therefore, in the design of gene VIII-fused peptide libraries (FIG. 4A) the amino acid diversity of the first 4 residues ($X_1$-$X_4$) of the peptide library was restricted to I-V-G-G (SEQ ID NO:15), then followed by 7 random positions ($X_5$-$X_{11}$). This is accomplished by providing oligonucleotide sequences where the first four codons encode the sequence I-V-G-G (SEQ ID NO:15) and the following seven codons are each NNK and encode any of the 20 naturally occurring amino acids. Thus, every member of the library contained a conserved, free N-terminus with a high propensity to insert into the serine protease-like activation pocket, thereby enhancing the probability of finding activator peptides. These peptide libraries were termed Zymogen Activator Peptide (ZAP) libraries.

After 4 rounds of panning scHGF β with the ZAPtide library, peptides were found that were specific for the zymogen-like form compared to the protease-like form of HGF β (Table 4B). Subsequent affinity maturation was carried out on positions $X_2$-$X_{11}$ and a clear 11-mer consensus peptide sequence was revealed, I-(V/I)-(D/G)-(D/G)-Y-P-W-W-(M/I/V)-(D/E)-(V/A) (SEQ ID NO:114) (FIGS. 4B and 4C). Interestingly, the first 6 positions within the consensus sequence showed direct similarity or identity with the first 6 positions of native HGF β N-terminus (V-V-N-G-I-P) (SEQ ID NO:115). Specifically, the motif: I-(V/I)-(D/G)-(D/G)-Y-P shares three identical residues ($X_1$-V-$X_3$-G-$X_5$-P), and three similar residues (I-$X_2$-D-$X_4$-I-$X_6$). The remaining 5 residues within the peptide sequence: $X_7$-$X_{11}$ (W-W-(M/I/V)-(D/E)-(V/A)) show no conservation with the native HGF β sequence, yet are likely critical for the binding affinity given their high frequency in the phage peptide sequences.

Example 2

Synthetic Peptides Based on the Phage-Derived Consensus Motif Bind scHGF β with High Affinity and Activate scHGF β Binding to Met Based on the finding that the consensus ZAPs contain features consistent with binding and inserting into the activation pocket, several related peptides were synthesized and utilized in a previously established scHGF β activation assay to assess their affinities and ability to active Met binding (Landgraf, K. E. et al. (2010) *J Biol Chem* 285: 40362-72). Since scHGF β can only weakly interact with the Met Sema-PSI domain compared to the active HGF β form, biolayer interferometry was used in the activation assay to measure the ability of a peptide to directly enhance the binding affinity of scHGF β to a streptavidin sensor surface coated with biotinylated Met (Landgraf, K. E. et al. (2010) *J Biol Chem* 285: 40362-72). Thus, titration of an activator peptide should result in a significant increase in the surface response signal due to enhanced scHGF β binding to Met.

Figure 5A:
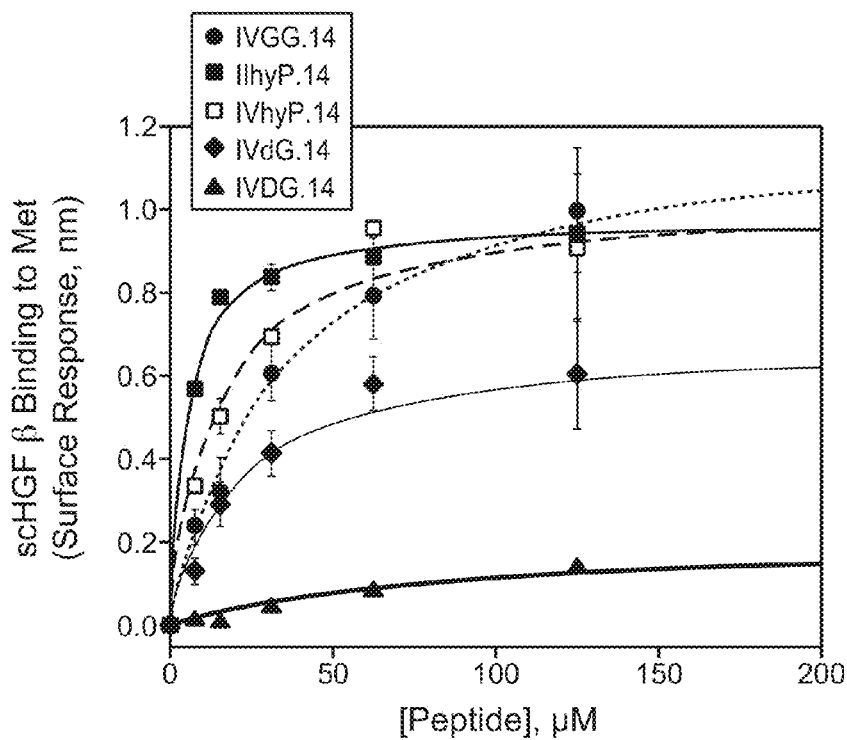
FIG. 5. Binding affinities for synthetic peptides that activate scHGF β binding to Met. (A) Titrations of peptides displaying allosteric activation of scHGF β. (B) Titrations of peptides that lack allosteric activation activity of scHGF β.
Figure 5B:
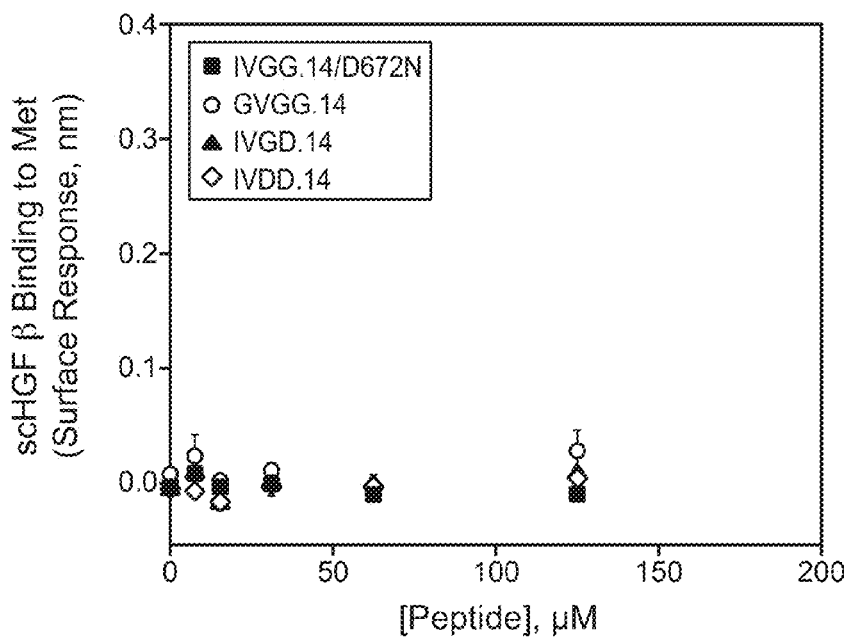

Using this assay, the IVGG.14 peptide had a $K_D$ of 34±3 μM (FIG. 5A, Table 4A) and its ability to activate Met binding was strictly dependent on the electrostatic and hydrophobic interactions made with the activation pocket. There was a lack of activity observed with the IVGG.14 peptide and the scHGF β D672N mutant (lack of electrostatic interactions). Further, there was a lack of activity observed with the GVGG.14 peptide and the scHGF β (lack of hydrophobic interactions) (FIG. 5B)). Importantly, the IVGG.14 peptide was ca. 60-fold more potent than the peptides derived from the native N-terminus of the β-chain of HGF (Landgraf, K. E. et al. (2010) *J Biol Chem* 285: 40362-72). Notably, the peptide variants containing aspartic acid residues in positions 3 and/or 4 displayed little to no activity. The IVDG.14 peptide variant had weak binding affinity ($K_D$ of 85±23 μM, Table 4A), while the IVGD.14 and IVDD.14 variants displayed no detectable binding (FIG. 5B). This result was likely based on the observation that an Asp in position 4 would undergo steric clash with the scHGF β protein, preventing N-terminal insertion, and rendering the peptide inactive (FIG. 1). However, the partial activity observed with Asp in position 3 was consistent with the fact that the native sequence contains a highly similar Asn residue, but the strained backbone conformation necessary to accommodate the Asp during N-terminal insertion would be energetically unfavorable. Based on this data, a non-natural D-aspartic acid was incorporated into position 3 hypothesizing that this may recover binding affinity and activity by relieving this unfavorable backbone and side chain configuration. The IVdG.14 peptide showed a clear recovery of activity and binding affinity resulting in a $K_D$ of 21±4 μM (FIG. 5A, Table 4A), 100-fold better than peptides previously described (Landgraf, K. E. et al. (2010) *J Biol Chem* 285: 40362-72). In addition, the solubility of this peptide variant is enhanced by the polar aspartic acid side chain while maintaining increased activity compared to the IVDG.14 variant.

TABLE 4A

Binding affinities for the peptides evaluated in the scHGF β activation/Met binding assay.

| Peptide | Sequence | SEQ ID NO: | $K_D$ (μM) |
|---|---|---|---|
| IVGG.14 | I V G G Y P W W M D V | 38 | 34 ± 3 |
| GVGG.14 | G V G G Y P W W M D V | 116 | N.D.[a] |
| IVGD.14 | I V G D Y P W W M D V | 86 | N.D.[a] |
| IVDD.14 | I V D D Y P W W M D V | 106 | N.D.[a] |
| IVDG.14 | I V D G Y P W W M D V | 39 | 85 ± 23 |
| IVdG.14[b] | I V d G Y P W W M D V | | 21 ± 4 |
| IVhyP.14[c] | I V G G Y hyP W W M D V | 40 | 14 ± 3 |
| IIhyP.14 | I I G G Y hyP W W M D V | 41 | 5 ± 1 |
| ZAP.01 | I I G G D P Y W V P H P G D A | 123 | 6 ± 1 |
| ZAP.03 | I I G G C P Y W M D R E E C I | 124 | 0.3 ± 0.1 |
| ZAP.03G | G I G G C P Y W M D R E E C I | 168 | N.D.[a] |
| ZAP.03S | I I G G S P Y W M D R E E S I | 125 | 59 ± 30 |

[a]N.D., not determined.

[b]d = D-aspartic acid.

[c]hyP = hydroxyproline

TABLE 4B

| ZAPtide Library | SEQ ID NO | I | V | G | G | X | X | X | X | X | X X | #[b] |
|---|---|---|---|---|---|---|---|---|---|---|---|---|
| ZAP.09 | 128 | I | V | G | G | D | Y | W | W | V | P I | 13 |
| ZAP.03 | 129 | I | V | G | G | D | F | Y | S | S | Y W | 12 |
| ZAP.06 | 130 | I | V | G | G | D | G | M | P | W | W I | 13 |
| IVGG.14 | 38 | I | V | G | G | Y | P | W | W | M | D V | 12 |
| ZAP.43 | 131 | I | V | G | G | D | P | V | Y | V | L Y | 3 |
| ZAP.13 | 132 | I | V | G | G | Y | P | W | W | I | T G | 3 |
| ZAP.53 | 133 | I | V | G | G | Y | P | W | W | V | D V | 2 |
| ZAP.30 | 134 | I | V | G | G | Y | P | A | W | M | E Y | 2 |
| ZAP.04 | 135 | I | V | G | G | S | D | F | P | W | W V | 2 |
| ZAP.52 | 136 | I | V | G | G | L | W | E | M | W | V T | 2 |
| ZAP.65 | 137 | I | V | G | G | E | P | A | Y | W | Y W | 1 |
| ZAP.11 | 138 | I | V | G | G | H | P | M | S | P | F S | 1 |
| ZAP.15 | 139 | I | V | G | G | D | P | W | W | F | V S | 1 |
| ZAP.67 | 140 | I | V | G | G | P | H | K | A | F | L L | 1 |
| ZAP.32 | 141 | I | V | G | G | E | P | V | W | Y | V W | 1 |
| ZAP.91 | 142 | I | V | G | G | Y | P | V | Y | F | L N | 1 |
| ZAP.51 | 143 | I | V | G | G | E | P | V | Y | V | V T | 1 |
| ZAP.24 | 144 | I | V | G | G | C | K | R | S | Y | W E | 1 |
| ZAP.29 | 145 | I | V | G | G | T | R | C | N | D | W I | 1 |
| ZAP.39 | 146 | I | V | G | G | S | A | C | L | I | A M | 1 |
| ZAP.01a | 147 | I | V | G | G | V | R | C | W | V | S N | 1 |
| ZAP.54 | 148 | I | V | G | G | L | D | V | E | Y | E L | 1 |
| ZAP.63 | 149 | I | V | G | G | M | R | L | C | G | Y I | 1 |
| ZAP.25 | 150 | I | V | G | G | N | K | I | W | S | V S | 1 |
| ZAP.50 | 151 | I | V | G | G | D | Y | Y | W | V | V Q | 1 |
| ZAP.45 | 152 | I | V | G | G | K | W | Q | R | K | R V | 1 |
| ZAP.18 | 153 | I | V | G | G | F | V | F | W | C | D Q | 1 |

[b]Number of copies recovered after sequencing 96 clones (consensus peptide in Table 4B disclosed as SEQ ID NO: 169).

Besides probing the nature of N-terminal insertion of the first 4 residues, enhancement of the binding affinity by altering two hydropohobic positions was evaluated. First, a substitution of the Pro at position 6 to hydroxyproline was made to help improve solubility and possibly gain additional H-bonding interactions. The IVhyP.14 variant displayed a $K_D$ of 14±3 µM, a small 2-fold enhancement relative to IVGG.14 peptide (Table 4A). In addition, since the hydrophobic properties of the first two residues of the β-chain of HGF are critical for N-terminal insertion (Kirchhofer, D. et al. (2007) Proc Natl Acad Sci USA 104: 5306-11), Val in position 2 was changed to an Ile in the context of the hydroxyproline substitution. The resulting variant, IIhyP.14, displayed a significant improvement in affinity (5±1 µM, Table 4A), 7-fold better than IVGG.14 and >400-fold better than the previously described peptide activators (Landgraf, K. E. et al. (2010) J Biol Chem 285: 40362-72).

Taken together these findings clearly demonstrate the phage-derived peptides described herein specifically bind to the activation pocket of zymogen scHGF β and allosterically activate Met binding. Mechanistically, this activity was shown to depend critically on the electrostatic and hydrophobic interactions between the N-terminal residues and the activation pocket, which is a hallmark of allosteric activation of the trypsin/chymotrypsin-like serine protease domain, as well as interactions with the conserved Pro in position 6. Furthermore, the novel activator peptide IVGG.14 and non-natural amino acid variants, IVhyP.14 and IIhyP.14, display dramatically improved binding affinities; thereby, validating the approach using the activation pocket-specific phage library to identify activator peptides.

Biolayer interferometry was utilized to measure peptide-dependent activation of zHGF β binding to surface immobilized Met ECDTitrations revealed ZAP.09 had an apparent activation constant (AC50) of 42 µM, while IVGG.14 had an AC50 of 21 µM, representing >90-fold improvement over previous activators. Notably, the ZAP.14-zHGF β complex bound to Met with an affinity of 690 nM, nearly identical to that of HGF β itself. The mechanism of activation for IVGG.14 was further validated by either mutating the critical Asp672 within the activation pocket of zHGF β to Asn (D672N) or substituting Ile1 of IVGG.14 with Gly (GVGG.14) and showed these perturbations completely abolished activity, strongly suggesting that IVGG.14 binds to the activation pocket and stabilizes zHGF β in an active conformation.

Example 3

Synthetic Peptides Activate Pro-HGF and Stimulate Cell Survival

To test whether these novel, more potent peptide activators could also activate the full-length form of pro-HGF and stimulate Met signaling, the peptides were screened for activity in a cell survival assay. A non-cleavable form of pro-HGF (scHGF), which is inactive as a Met ligand, has been shown to not stimulate cell survival under serum-starved media conditions; however, activator peptides in combination with scHGF could to signal through Met and dramatically enhance cell survival similar to that of the proteolytically activated HGF ligand (Landgraf, K. E. et al. (2010) J Biol Chem 285: 40362-72). Using Bx-PC3 cells, peptide titrations in the presence of scHGF were performed and observed robust activation was seen of scHGF signaling through Met, which reached levels equivalent HGF-induced signaling.

Figures 6A, 6B:
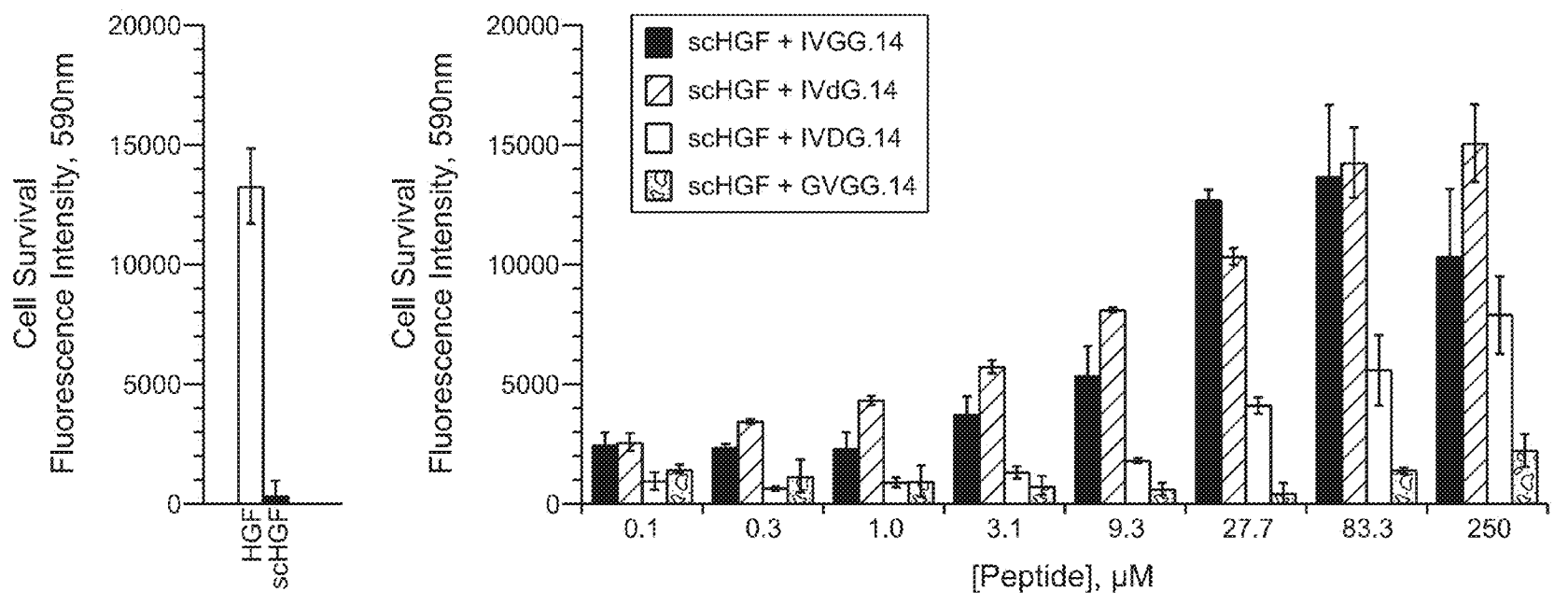

The IVGG.14 and IVdG.14 peptides displayed dose-dependent activation of scHGF with an $EC_{50}$ of ~20 µM peptide (FIG. 6B), in excellent agreement with the biochemical binding data ($K_D$ of 34±3 µM and 21±4 µM, respectively). In contrast, the GVGG.14 variant had no detectable activity, highlighting the important role for the hydrophobic N-terminal residue. Furthermore, titration of IVDG.14 resulted in partial scHGF signaling activity, in accord with data from the binding assays. Taken together, these data support the model where activator peptides bind to the activation pocket of the single chain zymogen-like form of HGF (either scHGF or pro-HGF), inducing a direct allosteric activation to a form of HGF that is essentially functionally equivalent to the two-chain form of HGF and thus capable of signaling through Met. Importantly, the peptide activated scHGF ligand displayed the same cell survival activity as the normal, activated form of the HGF ligand (FIG. 6A) suggesting that allosteric activation of pro-HGF can result in the same physiological effects as two-chain HGF and thus may have the same therapeutic applications.

Example 4

Structural Characterization of the IVGG.14 Activator Peptide

Given the ZAP analogues generated using natural and non-natural amino acid substitutions (above) showed only modest improvements in binding affinities relative to the IVGG.14 peptide the structure of the activator bound complex was determined in order to guide efforts toward engineering enhanced potency. To do this, excess IVGG.14 peptide was added to a stoichiometric mixture of a zymogen-like form of HGF β (HGF β V495G) and Met Sema-PSI ECD and screened for crystallization. The V495G mutant was used in place of scHGF β since V495G has similar properties to scHGF β (i.e., not an activator), but its size is smaller than zymogen scHGFP and essentially the same as the HGF β previously used to generate a structure of the activated HGF β/Met complex (Stamos, J. et al. (2004) *EMBO J* 23: 2325-35). Diffraction quality crystals were isolated and a 3.0 Å structure was solved of IVGG.14 bound to HGF β V495G in complex with the Met, which reveals the molecular details of the allosteric activation mechanism.

Overall, the peptide-activated complex was virtually identical in its structural alignment to the HGF β/Met complex solved previously (0.9 Å RMSD over all common atoms, Stamos, J. et al. (2004) *EMBO J* 23: 2325-35). This was consistent with the biochemical data showing that allosteric activation of zymogen-like HGF β results in high-affinity Met binding similar to cleaved HGF β. However, the critical difference in this structure was the canonical trypsin-like activation pocket within the HGF β domain was completely occupied by IVGG.14 instead of the native N-terminus from HGF β V495G (FIG. 8A). Within the first 9-residues of the bound activator (the last 2 C-terminal residues were not observed) there were two turn motifs; (i) an N-terminal type-II reverse turn, and (ii) a C-terminal type-I reverse turn. This global "S-shaped" activator structure allowed for the N-terminus to penetrate the HGF β activation pocket while the C-terminal portion reached around to a shallow binding patch on the protein surface (FIG. 8A). The main molecular interactions that appeared to stabilize the bound state included: a buried salt bridge between the N-terminal amine of IVGG.14 and the β-chain D672 residue, N-terminal hydrophobic interactions provided by the Ile in position 1 and the Val in position 2 fill the activation pocket and solvent-protect the salt bridge, backbone-backbone hydrogen-bonding network between the activator and HGF β, and van der Waals interactions within the P-W-W-M (SEQ ID NO:170) (also YPWWM (SEQ ID NO:171)) motif that encompassed the reverse turn and support packing against the protein surface (FIG. 8B). All of these features contributed to binding the activation pocket and resulted in a molecular mimicry mechanism whereby IVGG.14 structurally and functionally recapitulates the previously observed native N-terminal insertion (FIG. 3, Stamos, J. et al. (2004) *EMBO J* 23: 2325-35).

Remarkably, the IVGG.14 backbone closely mimics the first 6 N-terminal residues of activated HGF β, as well as multiple activated serine protease structures, and is precisely positioned to satisfy the conserved network of backbone hydrogen bonds that stabilize N-terminal insertion within canonical trypsin-like activation pockets. Alanine scanning of the unique YPWWM (SEQ ID NO:171) turn motif showed that P6A and W8A substitutions resulted in a 25- and 10-fold loss in activity, respectively, consistent with their conservation in phage-derived sequences. These data reveal IVGG.14 employs an N-terminal mimicry mechanism and utilizes a XPXWX reverse turn motif for stabilizing activator binding, two key features we sought to retain during IVGG.14 optimization.

Example 5

Discovery of High-Affinity Cyclic Peptide Activators Using Activity-Based Sorting of Structure-Guided Libraries Using the structural and functional information, a new 15-mer second-generation ZAP library was designed that retained key elements of the activator motif while also introducing aggressive diversity into the library. In addition, a novel activity-based phage sorting strategy was employed that enabled simultaneous 2-parameter selection for binding plus activation of scHGF β. In order to carry out activity-based sorting the phage library was incubated with scHGF β in solution for pre-binding then subjected to a capture step using a Met-coated surface. This 2-parameter sort highly enriched for binders that are activators since the zymogen-like scHGF β molecules that have been properly activated by bound phage clones have a much greater affinity for Met than scHGF β alone, which binds Met very weakly. Specific functional pressure on the phage library was applied in order to direct the selection towards allosteric activators, while avoiding the pitfalls inherent to the more traditional approach of only sorting for direct binders that may not be activators. The overall combined approach of structure-guided library design and activity-based sorting resulted in the discovery of more potent ZAPs.

Figures 9A, 9B, 9C:
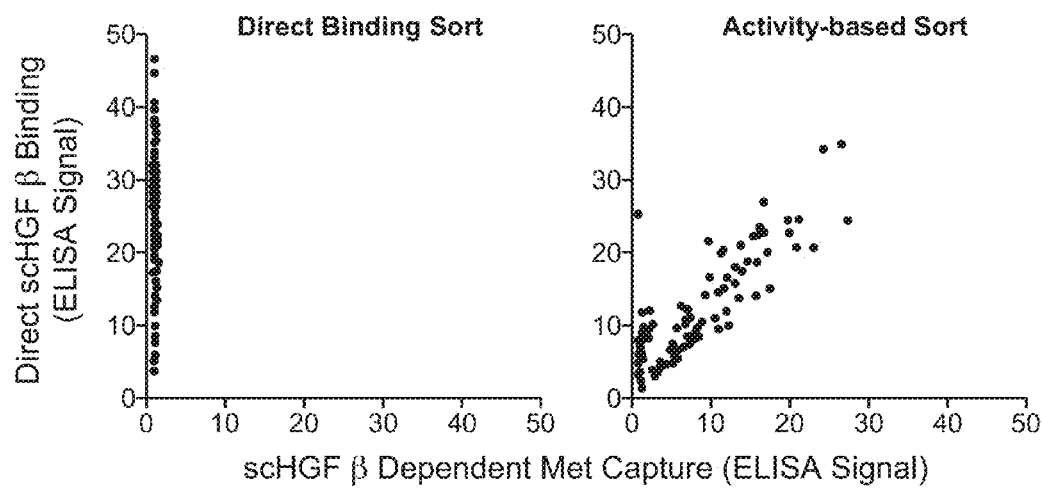
FIG. 9. Structure-guided library design and activity-based phage sorting. (A) Optimized 15-mer peptide library fused to the N-terminus of phage gene-VIII and designed based on structural information and selective randomization. (B) 2-dimensional ELISA results of 96 phage clones from control solution sorting (direct binding sort), or 96 clones from activity-based sorting (activity-based sort). ELISA signal from specific binding of phage to scHGF β is plotted along the y-axis, while ELISA signal from scHGF β-dependent Met capture is plotted along the x-axis. (C) Unique linear and cyclic sequences derived from activity-based sorting.

The new 15-mer ZAP-gene VIII phage library contained two main regions that were preferentially shielded from hard-randomization, the N-terminal motif which inserted into the activation pocket and a portion of the reverse turn motif that packs against the protein surface in the bound state (FIG. 8A). The resulting design contained restricted diversity within the 4-residue N-terminal motif (only position 2 could vary using a selective hydrophobic codon, NTT) and fixed proline and tryptophan residues at positions 6 and 8, respectively, while reintroducing hard-randomized positions throughout the remainder of the sequence (FIG. 9A). This library underwent 4 rounds of solution sorting against scHGF β, similar to the previous 11-mer ZAP library, then the library was split into two pools: one pool subjected to a 5th round solution sort as a control, while the other pool was subjected to 3 additional rounds of activity-based sorting (7 rounds total). Phage clones from the solution sort and activity-based sort were sequenced and subjected to a 2-dimensional ELISA analysis, where the clones were analyzed for (i) direct scHGF β binding and (ii) the ability of phage clones to be captured by Met only in the presence of scHGF β. Strikingly, when comparing the 2-dimensional ELISAs the clones that were only selected for direct interaction clearly bound specifically to scHGF β, but completely lacked the ability to activate scHGF β for Met capture, while the activity-based selection resulted in clones with significant binding and activity in the Met capture ELISA (FIG. 9B). The sequences of the activity-based clones showed a convergence on two types of activator peptides, a linear and cyclic version (FIG. 9C).

Functional characterization of representative linear and cyclic ZAPs (ZAP.01 and ZAP.03, Table 1) in both the scHGF β activation binding assay as well as cell survival assays demonstrate dramatic improvements in the overall potency of the activators. In the binding assays the cyclic ZAP.03 and linear ZAP.01 activators display affinities of 0.3±0.1 and 6±1 μM, respectively (FIG. 9, Table 1). This represents as much as a 100-fold improvement relative to our initial peptide activator IVGG.14 ($K_D$ of 34±3 μM, FIG. 5A, Table 4). Importantly, the single Ile-to-Gly substitution of the cyclic activator (ZAP.03G, FIG. 10, Table 4) significantly impairs its binding, which is consistent with N-terminal insertion into the scHGF β activation pocket and suggests a conserved mechanism of activity similar to IVGG.14. A new feature of the ZAP.03 activator is the intramolecular disulfide bond between Cys-5 and Cys-14, which cyclizes the peptide and appears to be critical for enhanced binding affinity since substitution of the cysteine residues to serine (ZAP.03S) results in a large reduction in affinity ($K_D$ of 59±30 μM, FIG. 10, Table 4). Additionally, in the Bx-PC3 cell survival assays the new ZAPs activate scHGF and stimulate cell survival to the same extent as cleaved HGF. Here, the activities are significantly more potent than IVGG.14 and dose-titrations of ZAP.03 and ZAP.01 activate scHGF with nanomolar and micromolar $EC_{50}$ values, respectively (FIG. 11A, B). Taken together, these results demonstrate the use of structure-guided library design and activity-based phage sorting to functionally interrogate new peptide sequence space and engineer ZAPs with dramatic enhancements in binding affinity and cell-based activity.

Figure 13A:
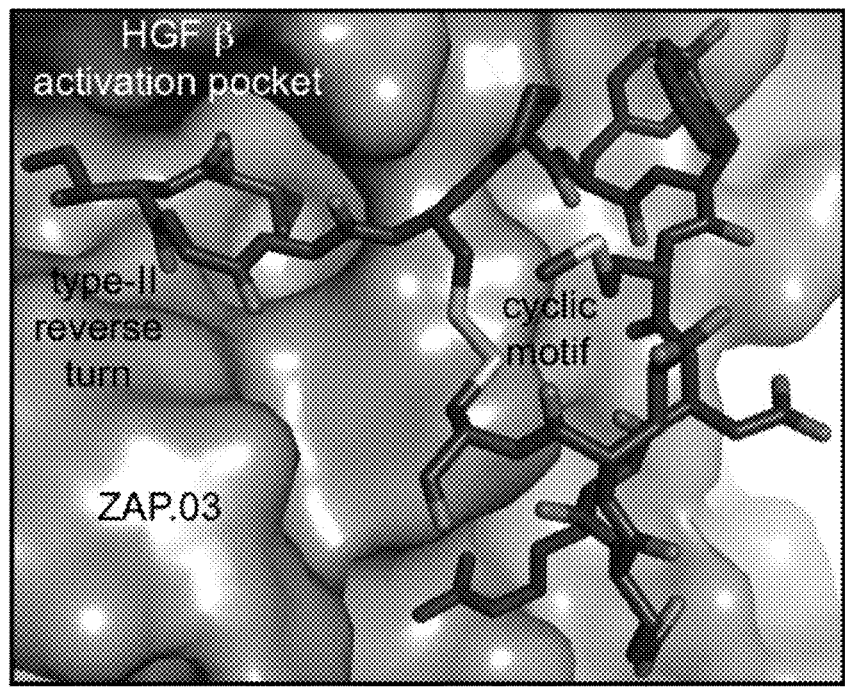
Figure 13B:
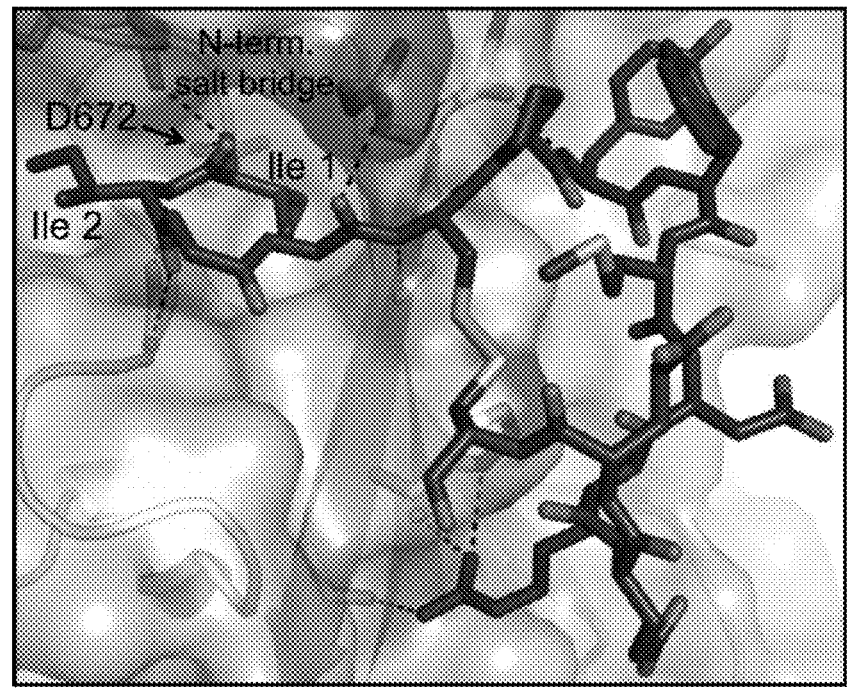

To understand the structural basis for the improved activity of ZAP.03 the 3.04 Å structure of the activator bound to HGF β V495G in complex with Met Sema PSI was solved as shown in FIG. 13A-B. The method of crystallization used is described above in Example 4, with minor differences. Diffraction quality crystals grew in 2 μL drops containing the activated complex mixed with an equal volume of seed stock diluted in reservoir (0.1 M Hepes pH 7, 8% P8000). Crystals were quickly transferred through an increasing concentration of glycerol (15-25%, 5% steps) in 0.1 M Hepes pH 7, 8% P8000 and cryopreserved. No crystal dehydration was used.

A crystal structure of ZAP.03 bound to HGF βV495G and Met Sema-PSI revealed the molecular details showing, the Cys5,14 disulfide bond that locks ZAP2.3 in position to satisfy the hydrogen bond network observed for IVGG.14 and also caps His633 of the HGF β-chain, using Arg11 to make new polar contacts with backbone carbonyls. An overlay of ZAPtide structures emphasizes how ZAP.03 retains IVGG.14 architecture while evolving a cyclic scaffold to accommodate additional polar interactions. Together, the two ZAPtide-activated ternary complexes validate the structure-guided phage display and sorting to hijack the canonical trypsin-like N-terminal insertion 'molecular sexuality' mechanism.

Cellular assays were used to address whether the optimized ZAPtides act as allosteric activators of pro-HGF and stimulate Met signaling in biologically relevant settings of cell survival and migration. Here, a noncleavable form of inactive pro-HGF containing a mutated cleavage site (scHGF) was used to avoid activation by endogenous serine proteases in cell culture. Notably, titrations of both IVGG.14 and ZAP.03 activated scHGF to induce cell survival during serum starvation of Met expressing BxPC3 cells, where ZAP2.3 displayed an EC50 of 0.4 μM and activated scHGF to the same extent as wild type two-chain HGF. Importantly, ZAPtides required the presence of scHGF as well as induced HeLa cell survival that was antagonized by an HGF-blocking anti-Met antibody, each confirming Met pathway selectivity. Additionally, in an in vitro wound closure assay, ZAP.-3 specifically activated HeLa cell migration only in the presence of scHGF and exhibited titratable control of the migration response with an EC50 of 0.06 μM. The striking correlation between the ZAP.03 zHGF β activation constant (0.3 μM) and its activity in both cell survival and migration assays (0.4 and 0.06 μM, respectively), combined with the observation that the single Ile1 to Gly mutation (ZAP.03G) dramatically hindered its activity, demonstrates that ZAPtides allosterically activate pro-HGF directly through the activation pocket of the serine protease-like β-chain and establishes a new pharmacological paradigm for controlling HGF-dependent Met signaling.

Example 6

Figure 12:
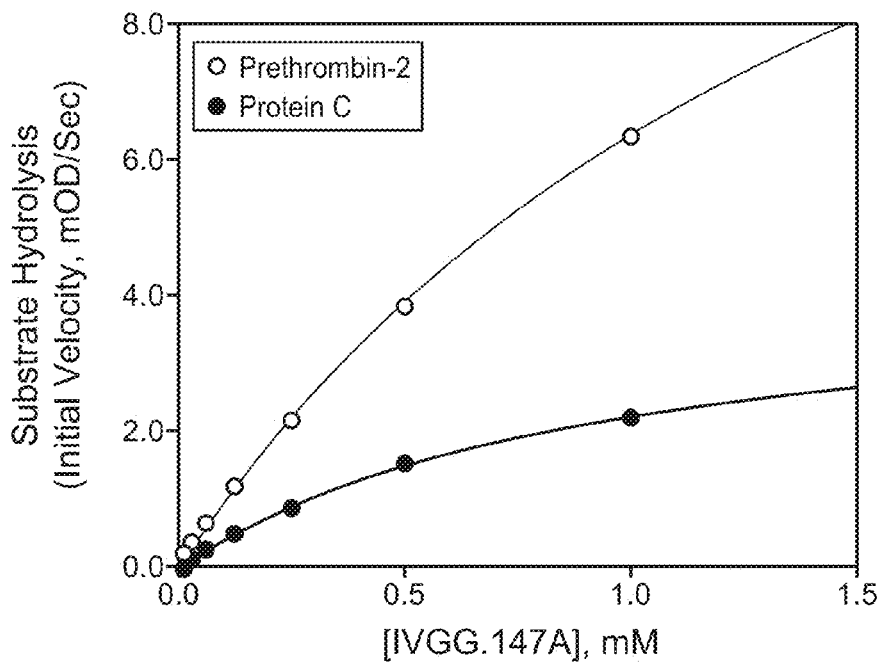

A ZAP Variant of IVGG.14 with Improved Solubility Activates Amidolytic Activity of Prethrombin-2 and Protein C Zymogen Serine Proteases The IVGG.14 peptide activator of pro-HGF took advantage of the canonical trypsin-like activation mechanism in order to allosterically activate binding of the serine protease-like domain within pro-HGF to Met. Given this activation mechanism is highly conserved among zymogens of the trypsin-like family of serine proteases and the fact that these proteins share a high degree of structural homology within the serine protease-like domains as well as the activation pockets, ZAPs for pro-HGF were analyzed for ability allosterically activate other zymogen serine proteases. One particular IVGG.14 variant, where an alanine substitution at position 7 was found to be exceptionally soluble (IVGG.147A, I V G G Y P A W M D V (SEQ ID NO:172)), was able to allosterically activate the amidolytic activity of zymogens prethrombin-2 and Protein C against the small tri-peptide substrate Ile-Pro-Arg-p-nitroaniline (IPR-pNA). The kinetic data showed that the initial rate of substrate hydrolysis ($V_i$) for both prethrombin-2 and Protein C zymogens significantly increased upon titration of IVGG.147A into the reaction (FIG. 12). Both prethrombin-2 and Protein C had extremely low or undetectable activity in the absence of activator, suggesting this ZAP variant was capable of allosterically activating these two serine protease zymogens. While the ZAP uncovered herein in this work appear to be orders of magnitude more specific for pro-HGF, the ZAP phaging approach may be used to engineer more potent and selective activators of zymogen serine proteases that work through the highly conserved trypsin-like N-terminal insertion mechanism.

The phage approach was also tested against pro-Macrophage Stimulating Protein (pro-MSP), another plasminogen-related growth factor, which, following proteolytic cleavage, signals through the RON receptor, having important roles in inflammation and cancer. Using a new cyclic library based on ZAP.03 (ZAPtide3 Library) and the described selection method a ZAPtide was discovered, ZAP3.2 that was specific for activating the zymogen-like pro-MSP β-chain (zMSP β) to bind RON with an AC50 of 134 μM. ZAPtides for both pro-HGF and pro-MSP are specific for activating their cognate serine protease-like domain targets, while avoiding activation of several serine protease zymogens tested, demonstrating the potential for selective activation of plasminogen-related growth factor pathways.

Discussion of Examples

To the best of our knowledge there is no precedence for engineering peptides with high affinity that specifically bind to the activation pocket of the serine protease-like zymogen domain of pro-HGF and act as allosteric activators to elicit Met signaling. The existence of the canonical trypsin/chymotrypsin-like activation pocket has been known and investigated previously for its role in allosteric activation of the serine protease fold (Bode, W. et al. (1978) *J Mol Biol* 118: 99-112; Khan, A. R. et al. (1998) *Protein Sci* 7: 815-36; Hedstrom, L. (2002) *Chem Rev* 102: 4501-24). In this work, novel phage peptide display libraries were developed based on the homology of N-terminal sequences found in trypsin/chymotrypsin-like serine protease domains, and utilized these libraries to site-specifically target the activation pocket of scHGF β. Typically, diverse phage peptide libraries are used to pan a target for high affinity peptide binders, yet the resulting binding site on the target is highly unpredictable (Lowman, H. B. (1997) *Annu Rev Biophys Biomol Struct* 26: 401-24; Sidhu, S. S. et al. (2000) *Methods Enzymol* 328: 333-63).

Structure-guided library design and activity-based phage sorting has been utilized to engineer high affinity ZAPs that bind the serine protease-like activation pocket of zymogen HGF β with nanomolar affinities and allosterically activate Met binding. Remarkably, a strong consensus peptide sequence was discovered and novel peptides related to this sequence are shown to be >400-fold more potent than our previously described peptides (Landgraf, K. E. et al. (2010) *J Biol Chem* 285: 40362-72). The 3.0 Å structure of a ZAP bound to a zymogen form of HGF β in complex with Met reveals a molecular mechanism whereby the ZAP binds to the activation pocket and closely mimics the native N-terminal insertion observed for active HGF β and other trypsin-like serine proteases. These structural details facilitated the design of a second phage peptide library, which was subjected to an activity-based sorting strategy that yielded new cyclic peptide activators with nanomolar binding affinity. ZAPs derived from phage libraries are up to 5000-fold more potent than peptides derived from the first 7-10 residues of the native HGF β N-terminus. Furthermore, these novel peptides not only have enhanced binding affinity, but retain the ability to allosterically activate scHGF β binding to Met and activate full length scHGF in cell survival assays. Remarkably, ZAPs activated pro-HGF displays similar signaling activity as proteolytically activated two-chain HGF in cell survival assays. These engineered ZAPs allosterically activate pro-HGF, bypassing the normal proteolytic activation step, and reveal a novel therapeutic strategy to elicit HGF-dependent Met signaling for chronic wound indications.

In addition to using these targeted peptide phage libraries against scHGF β, this method has general utility for discovering peptide activators of other serine protease zymogens and serine protease zymogen-like targets that comprise the trypsin/chymotrypsin superfamily. The trypsin/chymotrypsin family of serine proteases and protease-like proteins belong to Clan PA and is referred to as the Family S1 (also called S01) and described in the MEROPS database (http://merops.sanger.ac.uk) (Rawlings, N. D. et al. (2010) *Nucleic Acids Res* 38: D227-33). Data herein demonstrated that a highly soluble ZAP variant can activate the trypsin-like zymogen proteases prethrombin-2 and Protein C, suggesting this represents a novel strategy for directing peptide phage libraries towards the canonical activation pocket of a serine protease zymogen-like domain, and opens the door to discovering new ZAPs that allosterically regulate serine protease and protease-like zymogens.

These examples demonstrate an application of the serine protease-like activation mechanism of pro-HGF to the discovery of novel phage peptide libraries that site-specifically target pro-HGF and uncover unique peptide sequences and motifs that act as allosteric activators of pro-HGF. In addition to the peptide motif described in FIG. 4C, there are several sequence variations and synthetic (recombinant) modifications that may be used to enhance the activity of these molecules.

Given the extensive sequence information that exists for many trypsin/chymotrypsin-like serine proteases and the high degree of sequence similarity at the N-terminus of the serine protease or protease-like domain (Table 5), a more comprehensive consensus sequence is likely compatible with binding and allosteric activation of pro-HGF (FIG. 7). While I-V-G-G (SEQ ID NO:15) is a consensus sequence, it is clear that other sequences for $X_1$-$X_4$ are known that would also suffice to carry out the same activation pocket targeting strategy. For example, one could use the native N-terminal sequence for the β-chain of HGF itself (V-V-N-G) (SEQ ID NO:19) for $X_1$-$X_4$. Thus a peptide library where the first 4 residues ($X_1$-$X_4$) are restricted to V-V-N-G (SEQ ID NO:19) and the following 7 positions contain 7 random residues ($X_5$-$X_{11}$). Alternatively, a peptide library wherein the first 4 residues ($X_1$-$X_4$) are restricted to I-I-G-G (SEQ ID NO:18) and the following 7 positions contain 7 random residues ($X_5$-$X_{11}$) could be used. In fact, any combination of the residues that comprise the consensus motif described in FIG. 6 for positions $X_1$-$X_4$ could be used where the following 7 positions contain 7 random residues ($X_5$-$X_{11}$).

TABLE 5

Sequence homology of first 11 N-terminal residues found in selected human serine protease or serine protease-like domains compared to that found in human HGF. The first four N-terminal residues are in bold. Position 1 refers to position 16 using chymotrypsinogen numbering.

| Proteins containing serine protease or serine protease-like domains | SEQ ID NO: | Position |   |   |   |   |   |   |   |   |    |    |
|---|---|---|---|---|---|---|---|---|---|---|---|---|
|   |   | 1 | 2 | 3 | 4 | 5 | 6 | 7 | 8 | 9 | 10 | 11 |
| HGF | 42 | V | V | N | G | I | P | T | R | T | N | I |
| MSP | 43 | V | V | G | G | H | P | G | N | S | P | W |
| FVII | 44 | I | V | G | G | K | V | C | P | K | G | E |
| FIX | 45 | V | V | G | G | E | D | A | K | P | G | Q |
| FX | 46 | I | V | G | G | Q | E | C | K | D | G | E |

TABLE 5-continued

Sequence homology of first 11 N-terminal residues found in selected human serine protease or serine protease-like domains compared to that found in human HGF. The first four N-terminal residues are in bold. Position 1 refers to position 16 using chymotrypsinogen numbering.

| Proteins containing serine protease or serine protease-like domains | SEQ ID NO: | Position 1 2 3 4 5 6 7 8 9 10 11 |
|---|---|---|
| FXI | 47 | I V G G T A S V R G E |
| FXII | 48 | V V G G L V A L R G A |
| Glu-Plasminogen | 49 | V V G G C V A H P H S |
| Lys-Plasminogen | 50 | V V G G C V A H P H S |
| Protein C | 51 | L I D G K M T R R G D |
| Prothrombin | 52 | I V E G S D A E I G M |
| Plasma Kallikrein | 53 | I V G G T N S S W G E |
| Prostasin | 54 | I T G G S S A V A G Q |
| Enterokinase | 55 | I V G G S N A K E G A |
| Trypsin 2 | 56 | I V G G Y I C E E N S |
| Trypsin 1 | 57 | I V G G Y N C E E N S |
| Chymotrypsin B | 58 | I V N G E D A V P G S |
| Hepsin | 59 | I V G G R D T S L G R |
| HGFA | 60 | I I G G S S S L P G S |
| Matriptase | 61 | V V G G T D A D E G E |
| Testisin | 62 | I V G G E D A E L G R |
| Tryptase alpha 1 | 63 | I V G G Q E A P R S K |
| Tryptase beta 1 | 64 | I V G G Q E A P R S K |
| Tryptase beta 2 | 65 | I V G G Q E A P R S K |
| Tryptase gamma | 66 | I V G G H A A P A G A |
| Neurotrypsin | 67 | I I G G K N S L R G G |
| Apolipoprotein A | 68 | I V G G C V A H P H S |
| MASP 1 | 69 | I F N G R P A Q K G T |
| MASP 2 | 70 | I Y G G Q K A K P G D |
| PSA KLK3 | 71 | I V G G W E C E K H S |
| Haptoglobin | 72 | I L G G H L D A K G S |
| Complement C1r | 73 | I I G G Q K A K M G N |
| Complement C1s | 74 | I I G G S D A D I K N |
| Urokinase uPA | 75 | I I G G E F T T I E N |
| tPA | 76 | I K G G L F A D I A S |
| Complement Factor D | 77 | I L G G R E A E A H A |

Figure 10:
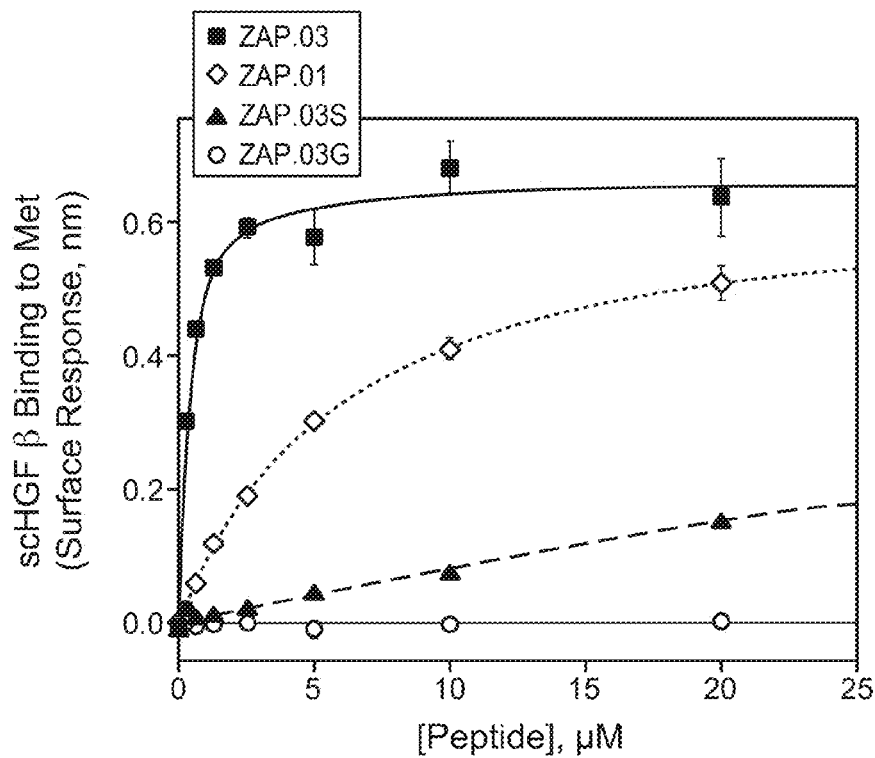
FIG. 10. Apparent binding affinities for optimized 15-mer linear (ZAP.01, diamonds) and cyclic (ZAP.03, squares) synthetic peptides that activate scHGF β binding to Met. The high-affinity binding of ZAP.03 is significantly impaired up capable of modulating activation of c-Met by HGF, in particular by interacting with the β-chain domain of pro-HGF. In one aspect, these zymogen activating molecules are generated by a combinatorial approach that results in the identification of zymogen activating molecules (e.g., ZAPs) capable of interacting with the β-chain domain of pro-HGF at various affinities and activating c-Met signaling. The identification of these zymogen activating molecules (e.g., ZAPs), and the structural dynamics of the binding interaction between the β-chain domain of pro-HGF and these zymogen activating molecules (e.g., ZAPs), as extensively described herein, further provide a means to identify other modulators capable of interacting with polypeptides comprising a trypsin/chymotrypsin-like serine protease domain and/or trypsin/chymotrypsin-like serine protease-like domain. In light of the importance of trypsin/chymotrypsin-like serine proteases and trypsin/chymotrypsin-like serine protease-like proteins such as HGF in various cellular and physiological processes, these modulators could be of significant utility, such as in prophylactic, therapeutic and/or diagnostic settings.

An optimization strategy was implemented that combined the use of structural information in specific phage library design, as well as activity-based phage sorting, to explore sequences beyond the 11-mer peptides and discover longer 15-mer activator peptides (FIG. 9C). The new sequences were either linear peptides that have additional residues on the C-terminus that likely contribute to binding affinity, or cyclic peptides containing an intramolecular disulfide bond important for binding affinity (FIG. 10, Table 4). In both cases for 15-mer activator peptides the positions $X_1$-$X_4$ may be consistent with the described consensus motif in FIG. 7, while the residues in positions $X_5$-$X_{15}$ may closely resemble those found in FIG. 9C since there was very little variability in those residues for the longer peptide activators. Peptides of 15 residues, or even longer, containing the conserved N-terminal motif in positions $X_1$-$X_4$ may have different arrangements of cysteine residues forming an intramolecular disulfide bond and still act as potent activators.

TABLE 6

X-ray Data Collection and Refinement for HGF β V495G/Met Sema-PSI/IVGG.14 peptide

| | HGF $β^{V495G}$/ Met SemaPSI/ IVGG.14 peptide | HGF $β^{V495G}$/ Met SemaPSI/ ZAP.03 peptide |
|---|---|---|
| Data collection | APS 21-IDF | SSRL 12-2 |
| space group | $P2_12_12_1$ | $P2_12_12$ |
| unit cell (Å, °) | a = 59.79, b = 121.5, c = 137.7 | a = 136.1, b = 139.6, c = 66.14 |
| $V_M$ (Å$^3$/Dalton) | 3.1 | 3.9 |
| Resolution (Å) | 50 – 2.99 (3.10 – 2.99) | 50 – 3.04 (3.05 – 3.04) |
| Rsym[a,b] | 0.112 (0.584) | 0.056 (0.625) |
| Number of observations | 127325 | 161138 |
| Unique reflections | 20873 | 24419 |
| Completeness (%)[b] | 99.7 (100) | 97.4 (98.3) |
| I/σI[b] | 15 (3.2) | 23 (2.6) |
| Wilson B (Å$^2$) | 75 | 103 |
| Refinement | | |
| Resolution (Å) | 50 – 3.00 | 35 – 3.04 |
| Reflctns (F>0 σ(F)) | 19851 | 24340 |
| Final R[c], R$_{FREE}$ | 0.224, 0.295 | 0.207, 0.251 |
| Molecules/asymmetric unit | 1 | 1 |
| protein residues | 727 | 733 |
| solvent molecules | 0 | 0 |
| atoms[d] | 5804 | 5786 |
| Mean B-factor (Å$^2$)[e] | 65 | 94 |
| Rmsd bonds (Å) | 0.006 | 0.009 |
| Rmsd angles (°) | 1.1 | 1.2 |
| Number of TLS groups | 11 | 0 |
| Ramachandran (%) | 89/8/3 | 91/7/2 |

[a]Rsym = Σ||I|| − |<I>||/Σ |<I>|, where I is the intensity of a single observation and <I> the average intensity for symmetry equivalent observations.

[b]In parenthesis, for the highest resolution shell.

[c]R = Σ|Fo − Fc|/Σ |Fo|, where Fo and Fc are observed and calculated structure factor amplitudes, respectively. R$_{FREE}$ is calculated as R for reflections sequestered from refinement.

[d]In parenthesis, the number of atoms assigned less than unit occupancy.

[e]protein/ligand/solvent/all atoms

TABLE 7

Selected ZAPtide sequences and activation constants (AC$_{50}$). Cysteine (C) residues highlighted in grey represent intramolecular disulfides in the peptides.

| ZAPtide | SEQ ID NO: | Sequence | | | | | | | | | | | | | | AC$_{50}$ (μM) |
|---|---|---|---|---|---|---|---|---|---|---|---|---|---|---|---|---|
| ZAP.09 | 128 | I | V | G | G | D | Y | W | W | V | P | I | | | | 42 ± 8 |
| IVGG.14 | 38 | I | V | G | G | Y | P | W | W | M | D | V | | | | 21 ± 4 |
| GVGG.14 | 116 | G | V | G | G | Y | P | W | W | M | D | V | | | | NB[a] |
| ZAP.01 | 127 | I | V | G | G | D | P | Y | W | V | P | H | P | G | D | A | 5.7 ± 0.2 |
| ZAP.03 | 124 | I | I | G | G | C | P | Y | W | M | D | R | E | E | C | I | 0.3 ± 0.1 |
| ZAP.03S | 125 | I | I | G | G | S | P | Y | W | M | D | R | E | E | S | I | 58 ± 30 |
| ZAP.03G | 168 | G | I | G | G | C | P | Y | W | M | D | R | E | E | C | I | NB[a] |
| HGF β mimic[b] | 30 | V | V | N | G | I | P | T | R | | | | | | | | 2000 ± 100 |
| ZAP3.2[c] | 163 | I | I | G | G | C | P | L | D | D | G | V | A | R | C | L | 134 ± 21 |

[a] NB = no binding
[b] HGF β N-terminal peptide mimic previously characterized using activator assay (28)
[c] ZAPtide3 activator for zMSP β

TABLE 8

ZAPtide2 clones derived from activity-based sorting (consensus peptide disclosed as SEQ ID NO: 173).

| ZAPtide2 Library[a] | SEQ ID NO: | I | X' | G | G | X | P | X | W | X | X | X | X | X | X | X | #[b] |
|---|---|---|---|---|---|---|---|---|---|---|---|---|---|---|---|---|---|
| linear | | | | | | | | | | | | | | | | | |
| ZAP.13 | 174 | I | I | G | G | D | P | V | W | D | I | T | Y | T | Y | A | 28 |
| ZAP.04 | 154 | I | I | G | G | D | P | Y | W | Y | P | H | P | G | T | V | 22 |
| ZAP.01 | 127 | I | V | G | G | D | P | Y | W | V | P | H | P | G | D | A | 21 |
| ZAP.56 | 155 | I | I | G | G | E | P | A | W | V | W | Y | E | D | C | M | 3 |
| ZAP.30 | 156 | I | I | G | G | D | P | W | W | T | P | H | P | S | F | V | 2 |
| ZAP.86 | 157 | I | V | G | G | D | P | W | W | V | D | H | M | Y | L | T | 1 |
| ZAP.17 | 158 | I | V | G | G | E | P | V | W | V | P | W | C | V | Y | D | 1 |
| ZAP.46 | 159 | I | I | G | G | D | P | V | W | V | L | S | T | E | C | G | 1 |
| ZAP.96 | 160 | I | I | G | G | E | P | W | W | V | D | F | V | E | D | Y | 1 |
| cyclic | | | | | | | | | | | | | | | | | |
| ZAP.03 | 124 | I | I | G | G | C | P | Y | W | M | D | R | E | E | C | I | 7 |
| ZAP.11 | 161 | I | V | G | G | C | P | Y | W | M | D | R | E | E | C | L | 3 |

[a] Library was generated as a fusion to the N-terminus of gene VIII (see methods).
X' = NTT codon for hydrophobic amino acids and
X = NNK codon for any amino acid.
Positions in bold were fixed in the library.
[b] Number of copies recovered after sequencing 96 clones.

TABLE 9

ZAPtide3 clones derived from activity-based sorting against zMSP β
(consensus peptide disclosed as SEQ ID NO: 175).

| ZAPtide3 Library[a] | SEQ ID NO: | I | I | G | G | C | P | X | X | X | X | X | X | X | C | X | #[b] |
|---|---|---|---|---|---|---|---|---|---|---|---|---|---|---|---|---|---|
| ZAP3.56 | 162 | I | I | G | G | C | P | T | Y | C | M | S | T | G | C | A | 71 |
| ZAP3.2 | 163 | I | I | G | G | C | P | L | D | D | G | V | A | R | C | L | 18 |
| ZAP3.30 | 164 | I | I | G | G | C | P | I | D | G | R | V | W | A | C | G | 3 |
| ZAP3.1 | 165 | I | I | G | G | C | P | A | A | V | S | N | S | V | C | Y | 2 |
| ZAP3.13 | 166 | I | I | G | G | C | P | A | G | S | E | L | A | V | C | T | 1 |
| ZAP3.4 | 167 | I | I | G | G | C | P | L | Y | C | M | I | T | G | C | A | 1 |

[a]Library was generated as a fusion to the N-terminus of gene VIII (see methods).
X = NNK codon for any amino acid.
Positions in bold were fixed in the library.
[b]Number of copies recovered after sequencing 96 clones.

PARTIAL LIST OF REFERENCES

Adams, P. D. et al. (2010). Acta Crystallogr D Biol Crystallogr 66, 213-221.
Arakaki, N. et al. (1995). Hepatology 22: 1728-34.
Bevan, D. et al. (2004). J Pathol 203: 831-8.
Bode, W. et al. (1978). J Mol Biol 118: 99-112.
Bussolino, F. et al. (1992). J Cell Biol 119: 629-41.
Derman, M. P. et al. (1995). Am J Physiol 268: F1211-7.
Donate, L. E. et al. (1994). Protein Sci 3: 2378-94.
Emsley, P. et al. (2010). Acta Crystallogr D66, 486-501.
Finn, R. D. et al. (2010). Nucleic Acids Res 38: D211-22.
Grant, D. S. et al. (1993). Proc Natl Acad Sci USA 90: 1937-41.
Hartmann, G. et al. (1992). Proc Natl Acad Sci USA 89: 11574-8.
Hedstrom, L. (2002). Chem Rev 102: 4501-24.
Kaibori, M. et al. (2002). J Surg Res 106: 108-14.
Khan, A. R. and James, M. N. (1998). Protein Sci 7: 815-36.
Kirchhofer, D. et al. (2007). Proc Natl Acad Sci USA 104: 5306-11.
Kirchhofer, D. et al. (2004). J Biol Chem 279: 39915-24.
Landgraf, K. E. et al. (2010). J Biol Chem 285: 40362-72.
Lee, S. L. et al. (2000). J Biol Chem 275: 36720-5.
Lokker, N. A. et al. (1992). EMBO J 11: 2503-10.
Lowman, H. B. (1997). Annu Rev Biophys Biomol Struct 26: 401-24.
Lowman, H. B. et al. (1998). Biochemistry 37: 8870-8.
Marchand-Adam, S. et al. (2006). Am J Respir Crit Care Med 174: 58-66.
McCoy, A. J., Grosse-Kunstleve, R. W., Adams, P. D., Winn, M. D., Storoni, L. C., and Read, R. J. (2007). J Appl Crystallogr 40, 658-674.
Murshudov, G. N. et al. (1997). Acta Crystallogr D53, 240-255.
Nakamura, T. et al. (1989). Nature 342: 440-3.
Nakamura, T. et al. (2011). J Gastroenterol Hepatol 26 Suppl 1: 188-202.
Naldini, L. et al. (1992). EMBO J 11: 4825-33.
Peek, M. et al. (2002). J Biol Chem 277: 47804-9.
Phin, S. et al. (2010). Am J Respir Cell Mol Biol 42: 286-93.
Rawlings, N. D. et al. (2010). MEROPS: the peptidase database. Nucleic Acids Res 38: D227-33.
Shimomura, T. et al. (1995). Eur J Biochem 229: 257-61.
Sidhu, S. S. et al. (2000). Methods Enzymol 328: 333-63.
Stamos, J. et al. (2004). EMBO J 23: 2325-35.
Stoker, M. et al. (1987). Nature 327: 239-42.
Tonikian, R. et al. (2007). Nat Protoc 2: 1368-86.
Tordai, H. et al. (1999). FEBS Lett 461: 63-7.
Watanabe, S. et al. (1994). Biochem Biophys Res Commun 199: 1453-60.

The invention claimed is:

1. An isolated zymogen activating peptide (ZAP), wherein the ZAP consists of the amino acid sequence $X_1$-$X_2$-$X_3$-$X_4$-$B_n$ (SEQ ID NO:2), wherein $X_1$ is L, I, or V, $X_2$ is I or V, $X_3$ is G, D, or N, $X_4$ is G or A, B is any amino acid, and n is a number between 7-11, wherein when $X_1$ is V, $X_3$ is not N and wherein the ZAP is capable of binding a serine protease-like domain with a binding affinity of less than about 100 μM.

2. The isolated ZAP of claim 1, wherein $X_1$ is I (SEQ ID NO:7).

3. The isolated ZAP of claim 1, wherein the $X_1$-$X_2$-$X_3$-$X_4$ (SEQ ID NO:14) is IIGG (SEQ ID NO:18) or IVGG (SEQ ID NO:15).

4. The isolated ZAP of claim 1, wherein $X_3$ is G (SEQ ID NO:12).

5. The isolated ZAP of claim 1, wherein $X_4$ is G (SEQ ID NO:13).

6. The isolated ZAP of claim 1, wherein the $X_1$-$X_2$-$X_3$-$X_4$ (SEQ ID NO:14) is IVGG (SEQ ID NO:15), IVDG (SEQ ID NO:16), IIGG (SEQ ID NO:18), VVGG (SEQ ID NO:20), LIDG (SEQ ID NO:22), or IVNG (SEQ ID NO:25).

7. The isolated ZAP of claim 1, wherein the ZAP specifically binds a polypeptide comprising a serine protease domain or serine protease-like domain and activates the polypeptide comprising the serine protease zymogen domain or serine protease-like zymogen domain.

8. The isolated ZAP of claim 7, wherein the ZAP specifically binds to the β-chain domain of pro-HGF and activates HGF signaling through c-Met.

9. The isolated ZAP of claim 8, wherein the ZAP specifically binds to the activation pocket of the β-chain domain of pro-HGF.

10. The isolated ZAP of claim 7, wherein the ZAP allosterically activates the polypeptide comprising the serine protease zymogen domain or serine protease-like zymogen domain.

11. A ZAP fusion comprising the ZAP of claim 1 and a carrier, wherein the carrier is conjugated to the C-terminus of the ZAP.

12. The ZAP fusion of claim 11, wherein the carrier is a biodegradable polymer.

13. The ZAP fusion of claim 11, wherein conjugation of the ZAP to the carrier increases the half-life and/or bioavailability of the ZAP compared to the ZAP unconjugated to the carrier.

14. The ZAP fusion of claim 12, wherein the biodegradable polymer is polyethylene glycol, polylactide, polyglycolide, or co-polymers thereof.

15. The ZAP fusion of claim 12, wherein the biodegradable polymer is a polypeptide carrier and the polypeptide carrier is albumin or an antibody or fragment thereof.

16. The ZAP fusion of claim 12, wherein $B_n$ is $X_5$-$X_6$-$X_7$-$X_8$-$X_9$-$X_{10}$-$X_{11}$-$X_{12}$-$X_{13}$-$X_{14}$-$X_{15}$ (SEQ ID NO:122), wherein $X_5$ is any amino acid, $X_6$ is P, $X_7$ is any amino acid, $X_8$ is W, and $X_9$-$X_{15}$ is any amino acid.

17. The ZAP fusion of claim 16, wherein the $X_1$-$X_2$-$X_3$-$X_4$ (SEQ ID NO:14) is IIGG (SEQ ID NO:18) or IVGG (SEQ ID NO:15).

18. The ZAP fusion of claim 1, wherein $B_n$ is $X_5$-$X_6$-$X_7$-$X_8$-$X_9$-$X_{10}$-$X_{11}$-$X_{12}$-$X_{13}$-$X_{14}$-$X_{15}$ (SEQ ID NO:122), wherein $X_5$ is any amino acid, $X_6$ is P, $X_7$ is any amino acid, $X_8$ is W, and $X_9$-$X_{15}$ is any amino acid.

19. The isolated ZAP of claim 18, wherein the $X_1$-$X_2$-$X_3$-$X_4$ (SEQ ID NO:14) is IIGG (SEQ ID NO:18) or IVGG (SEQ ID NO:15).

* * * * *

SEQUENCE LISTING

```
<160> NUMBER OF SEQ ID NOS: 175

<210> SEQ ID NO 1
<211> LENGTH: 728
<212> TYPE: PRT
<213> ORGANISM: Homo sapiens

<400> SEQUENCE: 1

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60
```

```
Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480
```

```
Asp His Pro Val Ile Ser Cys Ala Lys Thr Lys Gln Leu Arg Val Val
            485                 490                 495

Asn Gly Ile Pro Thr Arg Thr Asn Ile Gly Trp Met Val Ser Leu Arg
        500                 505                 510

Tyr Arg Asn Lys His Ile Cys Gly Gly Ser Leu Ile Lys Glu Ser Trp
    515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 2
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: A large hydrophobic amino acid
<220> FEATURE:
<221> NAME/KEY: MOD_RES
<222> LOCATION: (2)..(2)
<223> OTHER INFORMATION: A large hydrophobic amino acid or aromatic
      amino acid
<220> FEATURE:
<221> NAME/KEY: MOD_RES
<222> LOCATION: (3)..(3)
<223> OTHER INFORMATION: Gly, Asp, Glu, Asn, Gln, D-Gly, D-Asp, D-Glu,
      D-Asn or D-Gln
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent
```

-continued

```
<400> SEQUENCE: 2

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 3
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: A large hydrophobic amino acid
<220> FEATURE:
<221> NAME/KEY: MOD_RES
<222> LOCATION: (2)..(2)
<223> OTHER INFORMATION: A large hydrophobic amino acid or aromatic
      amino acid
<220> FEATURE:
<221> NAME/KEY: MOD_RES
<222> LOCATION: (3)..(3)
<223> OTHER INFORMATION: Gly, Asp, Glu, Asn, Gln or any D-amino acid
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 3

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 4
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met, Leu, Ile, Val or NorLeucine
<220> FEATURE:
<221> NAME/KEY: MOD_RES
<222> LOCATION: (2)..(2)
<223> OTHER INFORMATION: A large hydrophobic amino acid or aromatic
      amino acid
<220> FEATURE:
<221> NAME/KEY: MOD_RES
<222> LOCATION: (3)..(3)
<223> OTHER INFORMATION: Gly, Asp, Glu, Asn, Gln, D-Gly, D-Asp, D-Glu,
```

-continued

```
      D-Asn or D-Gln
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 4

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 5
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Leu, Ile or Val
<220> FEATURE:
<221> NAME/KEY: MOD_RES
<222> LOCATION: (2)..(2)
<223> OTHER INFORMATION: A large hydrophobic amino acid or aromatic
      amino acid
<220> FEATURE:
<221> NAME/KEY: MOD_RES
<222> LOCATION: (3)..(3)
<223> OTHER INFORMATION: Gly, Asp, Glu, Asn, Gln, D-Gly, D-Asp, D-Glu,
      D-Asn or D-Gln
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 5

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 6
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (2)..(2)
<223> OTHER INFORMATION: A large hydrophobic amino acid or aromatic
      amino acid
<220> FEATURE:
<221> NAME/KEY: MOD_RES
<222> LOCATION: (3)..(3)
<223> OTHER INFORMATION: Gly, Asp, Glu, Asn, Gln, D-Gly, D-Asp, D-Glu,
      D-Asn or D-Gln
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 6

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 7
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: A large hydrophobic amino acid or aromatic
      amino acid
<220> FEATURE:
<221> NAME/KEY: MOD_RES
<222> LOCATION: (3)..(3)
<223> OTHER INFORMATION: Gly, Asp, Glu, Asn, Gln, D-Gly, D-Asp, D-Glu,
      D-Asn or D-Gln
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 7

Ile Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa
    50
```

```
<210> SEQ ID NO 8
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: A large hydrophobic amino acid
<220> FEATURE:
<221> NAME/KEY: MOD_RES
<222> LOCATION: (2)..(2)
<223> OTHER INFORMATION: Met, Leu, Ile, Val, NorLeucine, Phe or Tyr
<220> FEATURE:
<221> NAME/KEY: MOD_RES
<222> LOCATION: (3)..(3)
<223> OTHER INFORMATION: Gly, Asp, Glu, Asn, Gln, D-Gly, D-Asp, D-Glu,
      D-Asn or D-Gln
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 8

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 9
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: A large hydrophobic amino acid
<220> FEATURE:
<221> NAME/KEY: MOD_RES
<222> LOCATION: (2)..(2)
<223> OTHER INFORMATION: Ile, Val, Leu or Phe
<220> FEATURE:
<221> NAME/KEY: MOD_RES
<222> LOCATION: (3)..(3)
<223> OTHER INFORMATION: Gly, Asp, Glu, Asn, Gln, D-Gly, D-Asp, D-Glu,
      D-Asn or D-Gln
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 9

Xaa Xaa Xaa Xaa Xaa Xaa Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa Xaa Xaa Xaa Xaa
        20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 10
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: A large hydrophobic amino acid
<220> FEATURE:
<221> NAME/KEY: MOD_RES
<222> LOCATION: (2)..(2)
<223> OTHER INFORMATION: Ile or Val
<220> FEATURE:
<221> NAME/KEY: MOD_RES
<222> LOCATION: (3)..(3)
<223> OTHER INFORMATION: Gly, Asp, Glu, Asn, Gln, D-Gly, D-Asp, D-Glu,
      D-Asn or D-Gln
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 10

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
        20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 11
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: A large hydrophobic amino acid
<220> FEATURE:
<221> NAME/KEY: MOD_RES
<222> LOCATION: (2)..(2)
<223> OTHER INFORMATION: A large hydrophobic amino acid or aromatic
      amino acid
<220> FEATURE:
<221> NAME/KEY: MOD_RES
<222> LOCATION: (3)..(3)
<223> OTHER INFORMATION: Gly, Asp or Asn
<220> FEATURE:
<221> NAME/KEY: MOD_RES
<222> LOCATION: (4)..(4)
<223> OTHER INFORMATION: Gly or Ala
<220> FEATURE:
```

```
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 11

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 12
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: A large hydrophobic amino acid
<220> FEATURE:
<221> NAME/KEY: MOD_RES
<222> LOCATION: (2)..(2)
<223> OTHER INFORMATION: A large hydrophobic amino acid or aromatic
      amino acid
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 12

Xaa Xaa Gly Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 13
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: A large hydrophobic amino acid
<220> FEATURE:
<221> NAME/KEY: MOD_RES
<222> LOCATION: (2)..(2)
<223> OTHER INFORMATION: A large hydrophobic amino acid or aromatic
      amino acid
<220> FEATURE:
<221> NAME/KEY: MOD_RES
<222> LOCATION: (3)..(3)
```

```
<223> OTHER INFORMATION: Gly, Asp, Glu, Asn, Gln, D-Gly, D-Asp, D-Glu,
      D-Asn or D-Gln
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 13

Xaa Xaa Xaa Gly Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A large hydrophobic amino acid
<220> FEATURE:
<221> NAME/KEY: MOD_RES
<222> LOCATION: (2)..(2)
<223> OTHER INFORMATION: A large hydrophobic amino acid or aromatic
      amino acid
<220> FEATURE:
<221> NAME/KEY: MOD_RES
<222> LOCATION: (3)..(3)
<223> OTHER INFORMATION: Gly, Asp, Glu, Asn, Gln, D-Gly, D-Asp, D-Glu,
      D-Asn or D-Gln
<220> FEATURE:
<221> NAME/KEY: MOD_RES
<222> LOCATION: (4)..(4)
<223> OTHER INFORMATION: Gly or Ala

<400> SEQUENCE: 14

Xaa Xaa Xaa Xaa
1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ile Val Gly Gly
1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Val Asp Gly
```

```
<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Val Gly Gly
1

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Ile Gly Gly
1

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Val Asn Gly
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Val Gly Gly
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Val Gly Gly
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 22

Leu Ile Asp Gly
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Val Glu Gly
1

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Thr Gly Gly
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Val Asn Gly
1

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Phe Asn Gly
1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ile Tyr Gly Gly
1

<210> SEQ ID NO 28
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 28

Ile Leu Gly Gly
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Lys Gly Gly
1

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Val Val Asn Gly Ile Pro Thr Arg
1               5

<210> SEQ ID NO 31
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: A large hydrophobic amino acid
<220> FEATURE:
<221> NAME/KEY: MOD_RES
<222> LOCATION: (2)..(2)
<223> OTHER INFORMATION: A large hydrophobic amino acid or aromatic
      amino acid
<220> FEATURE:
<221> NAME/KEY: MOD_RES
<222> LOCATION: (3)..(3)
<223> OTHER INFORMATION: Gly, Asp, Glu, Asn or Gln
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 31

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45
```

```
Xaa Xaa
    50

<210> SEQ ID NO 32
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: A large hydrophobic amino acid or aromatic
      amino acid
<220> FEATURE:
<221> NAME/KEY: MOD_RES
<222> LOCATION: (3)..(3)
<223> OTHER INFORMATION: Gly, Asp, Glu or Gln
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 32

Val Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 33
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met, Leu, Ile, Val or NorLeucine
<220> FEATURE:
<221> NAME/KEY: MOD_RES
<222> LOCATION: (2)..(2)
<223> OTHER INFORMATION: Met, Leu, Ile, Val, NorLeucine, Phe or Tyr
<220> FEATURE:
<221> NAME/KEY: MOD_RES
<222> LOCATION: (3)..(3)
<223> OTHER INFORMATION: Gly, Asp, Glu, Asn or Gln
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 33

Xaa Xaa Xaa Xaa Xaa Xaa Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa
    50

<210> SEQ ID NO 34
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Leu, Ile or Val
<220> FEATURE:
<221> NAME/KEY: MOD_RES
<222> LOCATION: (2)..(2)
<223> OTHER INFORMATION: Leu, Ile, Val or Phe
<220> FEATURE:
<221> NAME/KEY: MOD_RES
<222> LOCATION: (3)..(3)
<223> OTHER INFORMATION: Gly, Asp or Asn
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 34

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa
    50

<210> SEQ ID NO 35
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Leu, Ile, Val or Phe
<220> FEATURE:
<221> NAME/KEY: MOD_RES
<222> LOCATION: (3)..(3)
<223> OTHER INFORMATION: Gly, Asp, Glu or Gln
<220> FEATURE:
<221> NAME/KEY: MOD_RES
<222> LOCATION: (4)..(4)
<223> OTHER INFORMATION: Gly or Ala
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 35
```

```
Val Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 36
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Ile or Val
<220> FEATURE:
<221> NAME/KEY: MOD_RES
<222> LOCATION: (5)..(50)
<223> OTHER INFORMATION: Any amino acid and this region may encompass 0
      to 46 residues wherein some residues may be absent

<400> SEQUENCE: 36

Ile Xaa Gly Gly Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa
    50

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr or Phe
<220> FEATURE:
<221> NAME/KEY: MOD_RES
<222> LOCATION: (5)..(5)
<223> OTHER INFORMATION: Met, Ile or Val
<220> FEATURE:
<221> NAME/KEY: MOD_RES
<222> LOCATION: (6)..(6)
<223> OTHER INFORMATION: Asp or Glu
<220> FEATURE:
<221> NAME/KEY: MOD_RES
<222> LOCATION: (7)..(7)
<223> OTHER INFORMATION: Val or Ala

<400> SEQUENCE: 37

Xaa Pro Trp Trp Xaa Xaa Xaa
1               5

<210> SEQ ID NO 38
<211> LENGTH: 11
<212> TYPE: PRT
<213> ORGANISM: Artificial Sequence
```

```
-continued

<220> FEATURE:
<223> OTHER INFORMATION: Description of Artificial Sequence: Synthetic
      peptide

<400> SEQUENCE: 38

Ile Val Gly Gly Tyr Pro Trp Trp Met Asp Val
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Val Asp Gly Tyr Pro Trp Trp Met Asp Val
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Hydroxyproline

<400> SEQUENCE: 40

Ile Val Gly Gly Tyr Pro Trp Trp Met Asp Val
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Hydroxyproline

<400> SEQUENCE: 41

Ile Ile Gly Gly Tyr Pro Trp Trp Met Asp Val
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Val Val Asn Gly Ile Pro Thr Arg Thr Asn Ile
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 43

Val Val Gly Gly His Pro Gly Asn Ser Pro Trp
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Val Gly Gly Lys Val Cys Pro Lys Gly Glu
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Val Val Gly Gly Glu Asp Ala Lys Pro Gly Gln
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Val Gly Gly Gln Glu Cys Lys Asp Gly Glu
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ile Val Gly Gly Thr Ala Ser Val Arg Gly Glu
1               5                   10

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Val Gly Gly Leu Val Ala Leu Arg Gly Ala
1               5                   10

<210> SEQ ID NO 49
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Val Val Gly Gly Cys Val Ala His Pro His Ser
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Val Gly Gly Cys Val Ala His Pro His Ser
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Leu Ile Asp Gly Lys Met Thr Arg Arg Gly Asp
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ile Val Glu Gly Ser Asp Ala Glu Ile Gly Met
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ile Val Gly Gly Thr Asn Ser Ser Trp Gly Glu
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Thr Gly Gly Ser Ser Ala Val Ala Gly Gln
1               5                   10
```

```
<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ile Val Gly Gly Ser Asn Ala Lys Glu Gly Ala
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Val Gly Gly Tyr Ile Cys Glu Glu Asn Ser
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ile Val Gly Gly Tyr Asn Cys Glu Glu Asn Ser
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ile Val Asn Gly Glu Asp Ala Val Pro Gly Ser
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ile Val Gly Gly Arg Asp Thr Ser Leu Gly Arg
1               5                   10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 60

Ile Ile Gly Gly Ser Ser Ser Leu Pro Gly Ser
1               5                   10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Val Val Gly Gly Thr Asp Ala Asp Glu Gly Glu
1               5                   10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ile Val Gly Gly Glu Asp Ala Glu Leu Gly Arg
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ile Val Gly Gly Gln Glu Ala Pro Arg Ser Lys
1               5                   10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Val Gly Gly Gln Glu Ala Pro Arg Ser Lys
1               5                   10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ile Val Gly Gly Gln Glu Ala Pro Arg Ser Lys
1               5                   10

<210> SEQ ID NO 66
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 66

Ile Val Gly Gly His Ala Ala Pro Ala Gly Ala
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ile Ile Gly Gly Lys Asn Ser Leu Arg Gly Gly
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Val Gly Gly Cys Val Ala His Pro His Ser
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ile Phe Asn Gly Arg Pro Ala Gln Lys Gly Thr
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Tyr Gly Gly Gln Lys Ala Lys Pro Gly Asp
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Val Gly Gly Trp Glu Cys Glu Lys His Ser
1               5                   10
```

```
<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Leu Gly Gly His Leu Asp Ala Lys Gly Ser
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ile Ile Gly Gly Gln Lys Ala Lys Met Gly Asn
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Ile Gly Gly Ser Asp Ala Asp Ile Lys Asn
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ile Ile Gly Gly Glu Phe Thr Thr Ile Glu Asn
1               5                   10

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ile Lys Gly Gly Leu Phe Ala Asp Ile Ala Ser
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77
```

Ile Leu Gly Gly Arg Glu Ala Glu Ala His Ala
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ile Val Asp Asp Tyr Pro Trp Trp Ile Glu Val
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ile Val Asp Gly Tyr Pro Trp Trp Ile Asp Val
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ile Val Gly Asp Tyr Pro Trp Trp Ile Glu Val
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ile Val Asp Gly Tyr Pro Trp Trp Val Asp Val
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ile Val Tyr Asp Val Pro Trp Trp Met Asp Val
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 83

Ile Val Glu Asp Tyr Pro Trp Trp Val Glu Val
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ile Val Asp Gly Tyr Pro Trp Trp Met Glu Val
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ile Val Asp Asp Tyr Pro Trp Trp Ile Asp Val
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ile Val Gly Asp Tyr Pro Trp Trp Met Asp Val
1               5                   10

<210> SEQ ID NO 87
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ile Val Gly Glu Tyr Pro Trp Trp Met Asp Ala
1               5                   10

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ile Val Asp Gly Tyr Pro Trp Trp Met Asp Val
1               5                   10

<210> SEQ ID NO 89
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ile Val Ala Asp Tyr Pro Trp Trp Val Asp Val
1               5                   10

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ile Val Gly Asp Tyr Pro Trp Trp Val Asp Val
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ile Val Glu Asp Phe Pro Trp Trp Met Glu Ala
1               5                   10

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ile Val Gly Gly Phe Pro Trp Trp Ile Glu Ala
1               5                   10

<210> SEQ ID NO 93
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ile Val Glu Asp Tyr Pro Trp Trp Leu Asp Val
1               5                   10

<210> SEQ ID NO 94
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ile Val Asp Asp Tyr Pro Trp Trp Met His Ala
1               5                   10
```

-continued

```
<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Ile Val Asp Asp Tyr Pro Trp Trp Val Asp Val
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ile Pro Gly Asp Tyr Pro Trp Trp Ile Asp Val
1               5                   10

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ile Val Gly Glu Tyr Pro Trp Trp Val Asp Val
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ile Ser Asp Gly Tyr Pro Trp Trp Ile Asp Ala
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ile Val Asp Asp Tyr Pro Trp Trp Ile Glu Val
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 100

Ile Val Asp Gly Tyr Pro Trp Trp Met Asp Val
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ile Ile Gly Gly Glu Pro Trp Trp Met Asp Val
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ile Val Glu Asp Tyr Pro Trp Trp Met Tyr Val
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ile Val Asp Gly Tyr Pro Trp Trp Met Asp Val
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ile Val Asp Glu Tyr Pro Trp Trp Ile Gly Val
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ile Val Asp Asp Trp Pro Trp Trp Met Glu Val
1               5                   10

<210> SEQ ID NO 106
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 106

Ile Val Asp Asp Tyr Pro Trp Trp Met Asp Val
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ile Val Asp Gly Tyr Pro Trp Trp Leu Glu Val
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ile Val Gly Gly Tyr Pro Trp Trp Met Glu Val
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ile Val Gly Gly Tyr Pro Trp Trp Met Glu Ala
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ile Val Asp Gly Tyr Pro Trp Trp Ile Asp Val
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ile Ile Asp Asp Tyr Pro Trp Trp Met Glu Val
1               5                   10
```

```
<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ile Val Asp Asp Tyr Pro Trp Trp Met Asn Val
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ile Val Gly Gly Tyr Pro Trp Trp Met Asp Val
1               5                   10

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (3)..(4)
<223> OTHER INFORMATION: Asp or Gly
<220> FEATURE:
<221> NAME/KEY: MOD_RES
<222> LOCATION: (9)..(9)
<223> OTHER INFORMATION: Met, Ile or Val
<220> FEATURE:
<221> NAME/KEY: MOD_RES
<222> LOCATION: (10)..(10)
<223> OTHER INFORMATION: Asp or Glu
<220> FEATURE:
<221> NAME/KEY: MOD_RES
<222> LOCATION: (11)..(11)
<223> OTHER INFORMATION: Val or Ala

<400> SEQUENCE: 114

Ile Xaa Xaa Xaa Tyr Pro Trp Trp Xaa Xaa Xaa
1               5                   10

<210> SEQ ID NO 115
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Val Val Asn Gly Ile Pro
1               5

<210> SEQ ID NO 116
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 116

Gly Val Gly Gly Tyr Pro Trp Trp Met Asp Val
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Met, Ile or Val
<220> FEATURE:
<221> NAME/KEY: MOD_RES
<222> LOCATION: (10)..(10)
<223> OTHER INFORMATION: Asp or Glu
<220> FEATURE:
<221> NAME/KEY: MOD_RES
<222> LOCATION: (11)..(11)
<223> OTHER INFORMATION: Val or Ala

<400> SEQUENCE: 117

Ile Val Gly Gly Tyr Pro Trp Trp Xaa Xaa Xaa
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ile, Val or Leu
<220> FEATURE:
<221> NAME/KEY: MOD_RES
<222> LOCATION: (2)..(2)
<223> OTHER INFORMATION: Ile, Val, Leu, Tyr or Phe
<220> FEATURE:
<221> NAME/KEY: MOD_RES
<222> LOCATION: (3)..(3)
<223> OTHER INFORMATION: Gly, Asn, Asp or Glu
<220> FEATURE:
<221> NAME/KEY: MOD_RES
<222> LOCATION: (5)..(5)
<223> OTHER INFORMATION: Tyr or Phe
<220> FEATURE:
<221> NAME/KEY: MOD_RES
<222> LOCATION: (9)..(9)
<223> OTHER INFORMATION: Met, Ile or Val
<220> FEATURE:
<221> NAME/KEY: MOD_RES
<222> LOCATION: (10)..(10)
<223> OTHER INFORMATION: Asp or Glu
<220> FEATURE:
<221> NAME/KEY: MOD_RES
<222> LOCATION: (11)..(11)
<223> OTHER INFORMATION: Val or Ala

<400> SEQUENCE: 118

Xaa Xaa Xaa Gly Xaa Pro Trp Trp Xaa Xaa Xaa
1               5                   10

<210> SEQ ID NO 119
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr, Cys, Asp or Phe
<220> FEATURE:
<221> NAME/KEY: MOD_RES
<222> LOCATION: (2)..(2)
<223> OTHER INFORMATION: Tyr or Pro
<220> FEATURE:
<221> NAME/KEY: MOD_RES
<222> LOCATION: (3)..(3)
<223> OTHER INFORMATION: Trp or Tyr
<220> FEATURE:
<221> NAME/KEY: MOD_RES
<222> LOCATION: (4)..(4)
<223> OTHER INFORMATION: Trp or Asp
<220> FEATURE:
<221> NAME/KEY: MOD_RES
<222> LOCATION: (5)..(5)
<223> OTHER INFORMATION: Met, Ile or Val
<220> FEATURE:
<221> NAME/KEY: MOD_RES
<222> LOCATION: (6)..(6)
<223> OTHER INFORMATION: Asp, Pro or Glu
<220> FEATURE:
<221> NAME/KEY: MOD_RES
<222> LOCATION: (7)..(7)
<223> OTHER INFORMATION: Val, His, Arg, Ile or Ala

<400> SEQUENCE: 119

Xaa Xaa Xaa Xaa Xaa Xaa Xaa
1               5

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr, Cys, Asp or Ser
<220> FEATURE:
<221> NAME/KEY: MOD_RES
<222> LOCATION: (3)..(3)
<223> OTHER INFORMATION: Trp or Tyr
<220> FEATURE:
<221> NAME/KEY: MOD_RES
<222> LOCATION: (5)..(5)
<223> OTHER INFORMATION: Met, Ile or Val
<220> FEATURE:
<221> NAME/KEY: MOD_RES
<222> LOCATION: (6)..(6)
<223> OTHER INFORMATION: Pro, Asp or Glu
<220> FEATURE:
<221> NAME/KEY: MOD_RES
<222> LOCATION: (7)..(7)
<223> OTHER INFORMATION: His, Arg, Val or Ala
<220> FEATURE:
<221> NAME/KEY: MOD_RES
<222> LOCATION: (8)..(8)
<223> OTHER INFORMATION: Pro, Glu or absent
<220> FEATURE:
<221> NAME/KEY: MOD_RES
<222> LOCATION: (9)..(9)
<223> OTHER INFORMATION: Gly or Glu
<220> FEATURE:
<221> NAME/KEY: MOD_RES
<222> LOCATION: (10)..(10)
<223> OTHER INFORMATION: Asp, Cys or Ser
<220> FEATURE:
```

```
<221> NAME/KEY: MOD_RES
<222> LOCATION: (11)..(11)
<223> OTHER INFORMATION: Ala or Ile

<400> SEQUENCE: 120

Xaa Pro Xaa Trp Xaa Xaa Xaa Xaa Xaa Xaa Xaa
1               5                   10

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(7)
<223> OTHER INFORMATION: Any amino acid
<220> FEATURE:
<223> OTHER INFORMATION: see specification as filed for detailed
      description of substitutions and preferred embodiments

<400> SEQUENCE: 121

Xaa Pro Xaa Trp Xaa Xaa Xaa
1               5

<210> SEQ ID NO 122
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(4)
<223> OTHER INFORMATION: Any amino acid
<220> FEATURE:
<223> OTHER INFORMATION: see specification as filed for detailed
      description of substitutions and preferred embodiments

<400> SEQUENCE: 122

Xaa Xaa Xaa Xaa
1

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ile Ile Gly Gly Asp Pro Tyr Trp Val Pro His Pro Gly Asp Ala
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 124

Ile Ile Gly Gly Cys Pro Tyr Trp Met Asp Arg Glu Glu Cys Ile
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ile Ile Gly Gly Ser Pro Tyr Trp Met Asp Arg Glu Glu Ser Ile
1               5                   10                  15

<210> SEQ ID NO 126
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ile Val Gly Gly Cys Tyr Trp Trp Val Pro Ile
1               5                   10

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ile Val Gly Gly Asp Pro Tyr Trp Val Pro His Pro Gly Asp Ala
1               5                   10                  15

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ile Val Gly Gly Asp Tyr Trp Trp Val Pro Ile
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ile Val Gly Gly Asp Phe Tyr Ser Ser Tyr Trp
1               5                   10

<210> SEQ ID NO 130
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Ile Val Gly Gly Asp Gly Met Pro Trp Trp Ile
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Ile Val Gly Gly Asp Pro Val Tyr Val Leu Tyr
1               5                   10

<210> SEQ ID NO 132
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ile Val Gly Gly Tyr Pro Trp Trp Ile Thr Gly
1               5                   10

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ile Val Gly Gly Tyr Pro Trp Trp Val Asp Val
1               5                   10

<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ile Val Gly Gly Tyr Pro Ala Trp Met Glu Tyr
1               5                   10

<210> SEQ ID NO 135
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ile Val Gly Gly Ser Asp Phe Pro Trp Trp Val
1               5                   10
```

<210> SEQ ID NO 136
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ile Val Gly Gly Leu Trp Glu Met Trp Val Thr
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ile Val Gly Gly Glu Pro Ala Tyr Trp Tyr Trp
1               5                   10

<210> SEQ ID NO 138
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ile Val Gly Gly His Pro Met Ser Pro Phe Ser
1               5                   10

<210> SEQ ID NO 139
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Ile Val Gly Gly Asp Pro Trp Trp Phe Val Ser
1               5                   10

<210> SEQ ID NO 140
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ile Val Gly Gly Pro His Lys Ala Phe Leu Leu
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 141

Ile Val Gly Gly Glu Pro Val Trp Tyr Val Trp
1               5                   10

<210> SEQ ID NO 142
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ile Val Gly Gly Tyr Pro Val Tyr Phe Leu Asn
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Ile Val Gly Gly Glu Pro Val Tyr Tyr Val Thr
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Ile Val Gly Gly Cys Lys Arg Ser Tyr Trp Glu
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ile Val Gly Gly Thr Arg Cys Asn Asp Trp Ile
1               5                   10

<210> SEQ ID NO 146
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Ile Val Gly Gly Ser Ala Cys Leu Ile Ala Met
1               5                   10

<210> SEQ ID NO 147
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 147

Ile Val Gly Gly Val Arg Cys Trp Val Ser Asn
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ile Val Gly Gly Leu Asp Val Glu Tyr Glu Leu
1               5                   10

<210> SEQ ID NO 149
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ile Val Gly Gly Met Arg Leu Cys Gly Tyr Ile
1               5                   10

<210> SEQ ID NO 150
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ile Val Gly Gly Asn Lys Ile Trp Ser Val Ser
1               5                   10

<210> SEQ ID NO 151
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ile Val Gly Gly Asp Tyr Tyr Trp Val Val Gln
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ile Val Gly Gly Lys Trp Gln Arg Lys Arg Val
1               5                   10
```

```
<210> SEQ ID NO 153
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ile Val Gly Gly Phe Val Phe Trp Cys Asp Gln
1               5                   10

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ile Ile Gly Gly Asp Pro Tyr Trp Tyr Pro His Pro Gly Thr Val
1               5                   10                  15

<210> SEQ ID NO 155
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ile Ile Gly Gly Glu Pro Ala Trp Val Trp Tyr Glu Asp Cys Met
1               5                   10                  15

<210> SEQ ID NO 156
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ile Ile Gly Gly Asp Pro Trp Trp Thr Pro His Pro Ser Phe Val
1               5                   10                  15

<210> SEQ ID NO 157
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ile Val Gly Gly Asp Pro Trp Trp Val Asp His Met Tyr Leu Thr
1               5                   10                  15

<210> SEQ ID NO 158
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158
```

```
Ile Val Gly Gly Glu Pro Val Trp Val Pro Trp Cys Val Tyr Asp
1               5                   10                  15

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ile Ile Gly Gly Asp Pro Val Trp Val Leu Ser Thr Glu Cys Gly
1               5                   10                  15

<210> SEQ ID NO 160
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ile Ile Gly Gly Glu Pro Trp Trp Val Asp Phe Val Glu Asp Tyr
1               5                   10                  15

<210> SEQ ID NO 161
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Ile Val Gly Gly Cys Pro Tyr Trp Met Asp Arg Glu Glu Cys Leu
1               5                   10                  15

<210> SEQ ID NO 162
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ile Ile Gly Gly Cys Pro Thr Tyr Cys Met Ser Thr Gly Cys Ala
1               5                   10                  15

<210> SEQ ID NO 163
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ile Ile Gly Gly Cys Pro Leu Asp Asp Gly Val Ala Arg Cys Leu
1               5                   10                  15

<210> SEQ ID NO 164
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
                            -continued peptide

<400> SEQUENCE: 164

Ile Ile Gly Gly Cys Pro Ile Asp Gly Arg Val Trp Ala Cys Gly
1               5                   10                  15

<210> SEQ ID NO 165
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Ile Ile Gly Gly Cys Pro Ala Ala Val Ser Asn Ser Val Cys Tyr
1               5                   10                  15

<210> SEQ ID NO 166
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ile Ile Gly Gly Cys Pro Ala Gly Ser Glu Leu Ala Val Cys Thr
1               5                   10                  15

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ile Ile Gly Gly Cys Pro Leu Tyr Cys Met Ile Thr Gly Cys Ala
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gly Ile Gly Gly Cys Pro Tyr Trp Met Asp Arg Glu Glu Cys Ile
1               5                   10                  15

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(11)
<223> OTHER INFORMATION: Any amino acid

<400> SEQUENCE: 169

Ile Val Gly Gly Xaa Xaa Xaa Xaa Xaa Xaa Xaa
1               5                   10
```

-continued

```
<210> SEQ ID NO 170
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Pro Trp Trp Met
1

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Tyr Pro Trp Trp Met
1               5

<210> SEQ ID NO 172
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ile Val Gly Gly Tyr Pro Ala Trp Met Asp Val
1               5                   10

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (9)..(15)
<223> OTHER INFORMATION: Any amino acid

<400> SEQUENCE: 173

Ile Xaa Gly Gly Xaa Pro Xaa Trp Xaa Xaa Xaa Xaa Xaa Xaa Xaa
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
```

```
      peptide

<400> SEQUENCE: 174

Ile Ile Gly Gly Asp Pro Val Trp Asp Ile Thr Tyr Thr Tyr Ala
1               5                   10                  15

<210> SEQ ID NO 175
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(13)
<223> OTHER INFORMATION: Any amino acid
<220> FEATURE:
<221> NAME/KEY: MOD_RES
<222> LOCATION: (15)..(15)
<223> OTHER INFORMATION: Any amino acid

<400> SEQUENCE: 175

Ile Ile Gly Gly Cys Pro Xaa Xaa Xaa Xaa Xaa Xaa Xaa Cys Xaa
1               5                   10                  15
```